US006780890B2

(12) United States Patent
Bassler et al.

(10) Patent No.: US 6,780,890 B2
(45) Date of Patent: Aug. 24, 2004

(54) COMPOUNDS AND METHODS FOR REGULATING BACTERIAL GROWTH AND PATHOGENESIS

(75) Inventors: Bonnie L. Bassler, Princeton, NJ (US); Carol Dammel, Escondido, CA (US); Stephan Schauder, Princeton, NJ (US); Kevan Shokat, San Francisco, CA (US); Jeffrey Stein, San Diego, CA (US); Michael G. Surette, Calgary (CA)

(73) Assignees: University Technologies International, Inc. (CA); Quorex Pharmaceuticals, Inc., Carlsbad, CA (US); Princeton University, Princeton, NJ (US)

( * ) Notice: Subject to any disclaimer, the term of this patent is extended or adjusted under 35 U.S.C. 154(b) by 62 days.

(21) Appl. No.: 10/300,818

(22) Filed: Nov. 19, 2002

(65) Prior Publication Data

US 2004/0097402 A1 May 20, 2004

Related U.S. Application Data

(62) Division of application No. 09/853,832, filed on May 10, 2001, now Pat. No. 6,559,176.
(60) Provisional application No. 60/254,398, filed on Dec. 7, 2000, provisional application No. 60/203,000, filed on May 10, 2000, and provisional application No. 60/202,999, filed on May 10, 2000.

(51) Int. Cl.$^7$ .............................................. A61K 31/195
(52) U.S. Cl. ...................................................... 514/562
(58) Field of Search ......................................... 514/562

(56) References Cited

U.S. PATENT DOCUMENTS

| | | | |
|---|---|---|---|
| 4,107,121 A | 8/1978 | Stoy .......................... 263/29.6 |
| 4,692,417 A | 9/1987 | Webster ....................... 436/518 |
| 4,861,709 A | 8/1989 | Ulitzur et al. .................. 435/6 |
| 4,895,566 A | 1/1990 | Lee ............................. 604/266 |
| 4,917,686 A | 4/1990 | Bayston et al. ............. 604/265 |
| 4,952,419 A | 8/1990 | De Leon et al. ................. 427/2 |
| 5,013,306 A | 5/1991 | Solomon et al. ............. 604/265 |
| 5,196,318 A | 3/1993 | Baldwin et al. ........... 435/69.1 |
| 5,593,827 A | 1/1997 | Bycroft et al. .................. 435/6 |
| 5,612,184 A | 3/1997 | Rosson ........................... 435/6 |
| 5,637,113 A | 6/1997 | Tartaglia et al. ................ 623/1 |
| 5,658,748 A | 8/1997 | Mäyrä-Mäkinen et ....... 435/29 |
| 5,759,798 A | 6/1998 | Dunlap ......................... 435/29 |
| 5,788,979 A | 8/1998 | Alt et al. ..................... 424/426 |
| 5,902,283 A | 5/1999 | Darouiche et al. .......... 604/265 |
| 5,925,552 A | 7/1999 | Keogh et al. ............... 435/174 |
| 6,017,722 A | 1/2000 | Becvar et al. .................. 435/8 |
| 6,020,121 A | 2/2000 | Bao et al. ....................... 435/4 |
| 6,057,288 A | 5/2000 | Pearson et al. ................ 514/2 |
| 6,117,485 A | 9/2000 | Woodhall et al. ........... 427/156 |
| 6,197,591 B1 | 3/2001 | Stutzman-Engwall et al. ......................... 435/486 |
| 6,559,176 B1 * | 5/2003 | Bassler et al. .............. 514/408 |

FOREIGN PATENT DOCUMENTS

| | | |
|---|---|---|
| WO | WO 98/13328 | 4/1998 |
| WO | WO 98/40346 | 9/1998 |
| WO | WO 98/58075 | 12/1998 |
| WO | WO 99/00349 | 1/1999 |
| WO | WO 99/01119 | 1/1999 |
| WO | WO 99/29647 | 6/1999 |
| WO | WO 99/47545 | 9/1999 |
| WO | WO 00/11021 | 3/2000 |
| WO | WO 00/32152 | 6/2000 |
| WO | WO 01/85664 A2 | 11/2001 |

OTHER PUBLICATIONS

Adams et al., "The expression of hybrid HIV: Ty virus–like particles in yeast" *Nature*, vol. 329, pp. 68–70 (Sep. 3, 1987).

Ahmer et al., "*Salmonella typhimurium* Encodes an SdiA Homolog, a Putative Quorum Sensor of the LuxR Family, That Regulates Genes on the Virulence Plasmid" *Journal of Bacteriology*, pp. 1185–1193 (Mar. 1998).

Allart et al., "The catalytic mechanism of adenosylhomocysteine/methylthioadenosine nucleosidase from *Escherichia coli*: Chemical evidence for a transition state with a substantial oxocarbenium character" *Eur. J. Biochem.*, 256, pp. 155–162 (1998).

Baines et al., "Purification of Immunoglobulin G (IgG)" *Methods in Molecular Biology*, vol. 10: Immunochemical Protocols, Ed: M. Manson (1992).

Bassler et al. "Intercellular signaling in *Vibrio harveyi*: sequence and function of genes regulating expression of luminescence" *Molecular Microbiology*, 9(4) 773–786 (1993).

Bassler et al., "Multiple signaling systems controlling expression of luminescence in *Vibrio harveyi*: sequence and function of genes encoding a second sensory pathway" *Molecular Microbiology*, 13(2), pp. 273–286 (1994).

Bassler et al. "Intercellular Communication in Marine Vibrio Species: Density–Dependent Regulation of the Expression of Bioluminescence" *Two–Component Signal Transduction*, pp. 431–445 (1995).

Bassler et al., "Cross–Species Induction of Luminescence in the Qurorum–Sensing Bacterium *Vibrio harveyi*", *Journal of Bacteriology*, vol. 179, No. 12, pp. 4043–4045 (Jun. 1997).

Bassler, "How bacteria talk to each other: regulation of gene expression by quorum sensing" *Current Opinion in Microbiology*, 2:582–587 (1999).

Bassler et al., "A Multichannel Two–Component Signaling Relay Controls Quorum Sensing in *Vibrio harveyi*" *Cell–Cell Signaling in Bacteria*, pp. 259–273 (1999).

(List continued on next page.)

Primary Examiner—Kevin E. Weddington
(74) Attorney, Agent, or Firm—Knobbe Martens Olson & Bear LLP

(57) ABSTRACT

The invention provides autoinducer-2 analogs that regulate the activity of autoinducer-2 and methods of using such analogs for regulating bacterial growth and pathogenesis.

8 Claims, 38 Drawing Sheets

OTHER PUBLICATIONS

Bitter, "Heterologous Gene Expression in Yeast" *Methods in Enzymology*, vol. 152, pp. 673–684 (1987).

Bitter et al. "Expression and Secretion Vectors for Yeast" *Methods in Enzymology*, vol. 153, pp. 516–544 (1987).

Blattner et al. "The Complete Genome Sequence of *Escherichia coli* K–12" *Science*, vol. 277, pp. 1453–1462 (1997).

Brückner et al. "Regulation of the Inducible chloramphenicol acetyltransferase gene of the *Staphylococcus aureus* plasmid pUB112" *The EMBO Journal*, vol. 4 No. 9, pp. 2295–2300 (1985).

Caetano–Annollés, "Amplifying DNA with Arbitrary Oligonucleotide Primers" *PCR Methods and Applications*, 3:85–94 (1993).

Cheung et al. "Diminished Virulence of a sarlagr Mutant of *Staphylooccus aureus* in the Rabbit Model of Endocarditis" *The Journal of Clinical Investigation, Inc.*, vol. 94, pp. 1815–1822 (1994).

Conner et al. "Detection of sickle cell $\beta^s$–globin allele by hybridization with synthetic oligonucleotides" *Proc. Natl. Acad. Sci. USA*, vol. 80, pp. 278–282 (Jan. 1983).

Cornell et al., "Characterization of Recombinant *Eschericha coli* 5'–Methylthioadenosine/S–Adenosylhomocysteine Nucleosidase: Analysis of Enzymatic Activity and Substrate Specificity" *Biochemical and Biophysical Research Communications*, 228, pp. 724–732, Acticle No. 1723 (1996).

Cornell and Riscoe, "Cloning and expression of *Escherichia coli* 5'–methylthioadenosine/S–adenosylhomocysteine nucleosidase Identification of the pfs gene product" *Biochemica et Biophysica Acta* 1396, pp. 8–14 (1998).

Devereux et al. "A comprehensive set of sequence analysis programs for the VAX" *Nucleic Acids Research*, vol. 12, No. 1, pp. 387–395 (1984).

Dodd et al. "Improved detection of helix–turn–helix DNA–binding motifs in protein sequences" *Nucleic Acids Research*, vol. 18, No. 17, pp. 5019–5026 (1990).

Duerre, "A Hydrolytic Nucleosidase Acting on S–Adenosylhomocysteine and 5'–Methylthioadenosine" *The Journal of Biological Chemistry*, vol. 237, No. 12 pp. 3737–3741 (Dec. 1962).

Duerre and Miller, "Cleavage of S–Rebosyl–L–Homocysteine by Extracts from *Escherichia coli*" *Journal of Bacteriology*, vol. 91, No. 3, pp. 1210–1217 (1966).

Eberhard et al., "Structural Identification of Autoinducer of *Photobacterium fischeri* Luciferase" *Biochemistry*, vol. 20, No. 9, pp. 2444–2449 (1981).

Eberhard et al. "Analogs of the autoinducer of bioluminescence in *Vibrio fischeri*" *Arch Microbiol*, 146:35–40 (1986).

Engebrecht et al. "Bacterial Bioluminescence: Isolation and Genetic Analysis of Functions from *Vibrio fischeri*" *Cell*, vol. 32, pp. 773–781 (1983).

Erion et al., "Purine Nucleoside Phosphorylase. 1. Structure–Function Studies" *Biochemistry*, 36, pp. 11725–11734 (1997).

Freeman and Bassler, "A genetic analysis of the function of LuxO, a two–component response regulator involved in quorum sensing in *Vibrio harveyi*", *Molecular Microbiology*, 31(2), pp. 665–677 (1999).

Freeman and Bassler, "Sequence and Function of LuxU: a Two Component Phosphorelay Protein That Regulates Quorum Sensing in *Vibrio harveyi*", *Journal of Bacteriology*, vol. 181, No. 3, pp. 899–906 (Feb 1999).

Fuqua et al. "Quorum Sensing in Bacteria: the LuxR–Luxl Family of Cell Density–Responsive Transcriptional Regulators" *Journal of Bacteriology*, pp. 269–275 (Jan. 1994).

Garcia–Lara et al. "An Extracellular Factor Regulates Expression of sdiA, a Transcriptional Activator of Cell Division Genes in *Escherichia coli*" *Journal of Bacteriology*, pp. 2742–2748 (May 1996).

Gilson et al. "AlnS and a New Family of Autoinducer Synthesis Proteins" *Journal of Bacteriology*, pp. 6948–6951 (Dec. 1995).

*Goodman and Gilman's The Pharmacological Basis of Therapeutics* $7^{th}$ Ed., Macmillan Publishing Company (1985).

*Goodman & Gilman's The Pharmacological Basis of Therapeutics*, $9^{th}$ Ed., "Chemotherapy of Microbial Diseases", Section IX, pp. 1027–1223 (1996).

Green and Manson, "Production of Polyclonal Antisera" *Methods in Molecular Biology*, vol. 10: Immunochemical Protocols Ed.: M. Manson, Ch. 1, pp. 1–5 (1992).

Greenberg et al. "Induction of Luciferase Synthesis in *Beneckea harveyi* by Other Marine Bacteria" *Arch Microbiol*, 120, pp. 87–91 (1979).

Harlow and Lane, *Antibodies: A Laboratory Manual*, Cold Spring Harbor Laboratory (1988).

Hu et al., "Crystal Structure of S–Adenosylhomocysteine Hydrolase from Rat Liver" *Biochemistry*, 38, pp. 8323–8333 (1999).

Huisman and Kolter, "Sensing Starvation: A Homoserine Lactone–Dependent Signaling Pathway in *Escherichia coli*" *Science*, vol. 265, pp. 537–539 (Jul. 22, 1994).

Jones et al., "Molecular analysis of the operon which encodes the RNA polymerase sigma factor $\delta^{54}$ of *Escherichia coli*" *Microbiology*, 140, pp. 1035–1043 (1994).

Kaplan et al. "Synthesis of N-[3–OXO–(4,5–$^3$H2)–Hexanoyl] Homoserice Lactone: Biologically Active Tritium–Labelled *Vibrio fischeri* Autoinducer" *Journal of Labelled Compounds and Radiopharmaceuticals*–vol. XXII, No. 4, pp. 387–395 (1985).

Keen, "Plants and Microorganisms–listening in on the conversation" *Nature Biotechnology*, vol. 17, pp. 958–959 (Oct. 1999).

Klose and Mekalanos, "Distinct roles of an alternative sigma factor during both free–swimming and colonizing phases of the *Vibrio cholerae* pathogenic cycle" *Molecular Microbiology*, 28(3), pp. 501–520 (1998).

Koellner et al., "Crystal Structure of the Ternary Complex of *E. coli* Purine Nucleoside Phosphorylase with Formycin B, a Structural Analogue of the Substrate Inosine, and Phosphate (Sulphate) at 2.1 A Resolution" *J. Mol. Biol.*, 280, pp. 153–166, Article No. mb981799 (1998).

Köhler and Milstein "Continuous cultures of fused cells secreting antibody of predefined specificity" *Nature*, vol. 256, pp. 495–497 (Aug. 7, 1975).

Landergreen et al. "A Ligase–Mediated Gene Detection Technique" *Science*, vol. 241, pp. 1077–1080 (Aug. 26, 1988).

Landergreen et al. "DNA Diagnostics–Molecular Techniques and Automation" *Science*, vol. 242, pp. 229–237 (Oct. 14, 1998).

Langer, "New Methods of Drug Delivery" *Science*, vol. 249, pp. 1527–1533 (Sep. 28, 1990).

Lee and Nathans, "Proliferin Secreted by Cultures Cells Binds to Mannose 6–Phosphate Receptors" *The Journal of Biological Chemistry*, vol. 283, No. 7, pp. 3521–3527 (Mar. 5, 1988).

Maloy et al., *Genetic Analysis of Pathogenic Bacteria: A Laboratory Manual*, Cold Spring Harbor Laboratory Press (1996).

Mancini et al., "Cloning and Expression of the *Photobacterium phosphoreum* Luminescence System Demonstrates a Unique lux Gene Organization" *Journal of Biological Chemistry*, vol. 64, No. 28, pp. 14308–14314 (1988).

Manefield et al., "Evidence that halogenated furanones from *Delisea pulchra* inhibit acylated homoserine lactone (AHL)–mediated gene expression by displacing the AHL signal from its receptor protein" *Microbiology*, 145, pp. 283–291, (1999).

Manefield et al., "Inhibition of Luminescence of Virulence in the Black Tiger Prawn (*Penaeus monodon*) Pathogen *Vibrio harveyi* by Intercellular Signal Antagonists" *Applied and Environmental Microbiology*, vol. 66, No. 5, pp. 2079–2084 (May 2000).

Mao et al., "The crystal structure of *Escherichia coli* purine nucleoside phosporylase: a comparison with the human enzyme reveals a conserved topology" *Structure*, Research Article, vol. 5, No. 10, pp. 1373–1383 (1997).

Marmur, "A Procedure for the Isolation of Deoxyribonucleic Acid from Micro–organisms" *J. Mol. Biol.*, 3, pp. 208–218 (1961).

Martin et al., "Identification of a Locus Cotrolling Expression of Luminescence Genes in *Vibrio harvey*" *Journal of Bacteriology*, vol. 171, No. 5, pp. 2406–2414 (May 1989).

Miller and Duerre, "S–Ribosylhomocysteine Cleavage Enzyme from *Escherichia coli*" *The Journal of Biological Chemistry*, vol. 243, No. 1, pp. 92–97 (1968).

Miller, *A Short Course in Bacterial Genetics: A Laboratory Manual and Handbook for Escherichia coli and Related Bacteria*, Cold Spring Harbor Laboratory Press (1992).

Nealson and Hastings, "Bacterial Bioluminescence: Its Control and Ecological Significance" *Microbiological Reviews*, pp. 496–518 (Dec. 1979).

Otto et al., "Structure of the pheromone peptide of the *Staphylococcus epidermis* agr system" *FEBS Letters*, 424, pp. 89–94 (1998).

Otto et al., "Inhibition of virulence factor expression in *Staphylococcus aureus* by *Staphylococcus epidermis* agr pheromone and derivatives" *FEBS Letters*, 450, pp. 257–262 (1999).

Payne, "Detection, Isolation, and Characterization of Siderophores" *Methods in Enzymology*, vol. 235, pp. 329–344 (1994).

Plunkett and Ellman, "Combinatorial Chemistry and New Drugs" *Scientific American*, pp. 69–73, (Apr. 1997).

Poustka and Lehrach, "Genetic approaches to the cloning modification and characterization of cosmid clones and clone libraries" *Choice and use of cosmid vectors*, Ch. 3, pp. 57.

*Remington's Pharmaceutical Sciences*, $15^{th}$ Ed. Easton, Mack Publishing Co., pp. 1461–1487 (1975).

Rosenberg et al., "Vectors for selective expression of cloned DNAs by T7 RNA polymerase" *Gene*, 56, pp. 125–135 (1987).

Saiki et al., "A Novel Method for the Detection of Polymorphic Restriction Sites by Cleavage of Oligonucleotide Probes: Application to Sickle–Cell Anemia" *Bio/Technology*, 3:1008–1012 (1985).

Sambrook et al., *Molecular Cloning: A Laboratory Manual $2^{nd}$ Ed.*, Cold Spring Harbor Laboratory Press (1989).

Schägger and von Jagow, "Tricine–Sodium Dodecyl Sulfate–Polyacrylamide Gel Electrophoresis for the Separation of Proteins in the Range from 1 to 100 kDa" *Analytical Biochemistry*, 166, pp. 368–379 (1987).

Schwyn and Neilands, "Universal Chemical Assay for the Detection and Determination of Siderophores" *Analytical Biochemistry*, 160, pp. 47–56 (1987).

Showalter et al., "Cloning and Nucleotide Sequence of luxR, a Regulatory Gene Controlling Bioluminescence in *Vibrio harveyi*" *Journal of Bacteriology*, vol. 172, No. 6, pp. 2946–2954 (Jun. 1990).

Sitnikov et al, "Control of cell division in *Escherichia voli*: Regulation of transcription of flsQA involves bothn rpoS and SdiA–mediated autoinduction" *Proc. Natl. Acad. Sci. USA*, vol. 93, pp. 336–341 Microbiology (1996).

Sizemore et al., "Organization, promoter analysis and transcriptional regulation of the *Staphylococcus xylosus* xylose utilization operon" *Mol Gen Genet*, 227, pp. 337–384 (1991).

Strathem et al., *The Molecular Biology of the Yeast Saccharomyces*, Cold Spring Harbor Laboratory Press (1982).

Surette and Bassler, "Quorum sensing in *Escherichia coli* and *Salmonella typhimurium*" *Proc. Natl. Acad. Sci. USA*, vol. 95, pp. 7046–7050 (1998).

Surette and Bassler, "Regulation of autoinducer production in *Salmonella typhimurium*" *Molecular Microbiology*, 31(2), pp. 585–595 (1999).

Surette et al., "Quorum sensing in *Escherichia coli*, *Salmonella typhimurium*, and *Vibrio harveyi*: A new family of genes responsible for autoinducer production" *Proc. Natl. Acad. Sci. USA*, vol. 96, pp. 1639–1644 (Feb. 1999).

Walker and Duerre, "S–Adenosylhomocysteine Metabolism in Various Species" *Can. J. Biochem*, vol. 53, pp. 312–319 (1975).

Wang et al., "A factor that positively regulates cell division by activating transcription of the major cluster of essential cell division genes of *Escherichia coli*" *The EMBO Journal*, vol. 10, No. 11, pp. 3363–3372 (1991).

Yin et al., "Substrate Binding Stabilizes S–Adenosylhomocysteine Hydrolase in a Closed Conformation" *Biochemistry*, 39, pp. 9811–9818 (2000).

Becker et al. (1997) "Evidence for Interspecies Communication and its Potential Role in Pathogen Suppression in a Naturally Occuring Disease Suppressive Soil", *Canadian Journal of Microbiology*, 43:985–990.

Manefield et al. (2001) "Halogenated Furanones from the Red Alga, *Delisea pulchra*, Inhibit Carbapenem Antibiotic Synthesis and Exoenzyme Virulence Factor Production in the Phytopathogen *Erwinia carotovora*", *Federation of European Microbiological Societies—Microbiology Letters*, 205: 131–138.

Schaefer et al. (1996) "Quorum Sensing in *Vibrio fischeri*: Probing Autoinducer–LuxR Interactions with Autoinducer Analogs", *Journal of Bacteriology*, 178(10):2897–2901.

Sofer et al. (1999) "Subinhibitory Erythromycin Represses Production of *Pseudomonas aeruginosa* Lectins, Autoinducer and Virulence Factors", *Chemotherapy Microbiology*, 45:335–341.

Lilley et al. (2000) "Regulation of Quorum Sensing in *Vibrio harveyi* by LuxO and Sigma–54", *Molecular Microbiology*, 6(4):940–954, Blackwell Science Ltd.

Klose et al. (1998) "Identification of Multiple $\sigma^{54}$–Dependent Transcriptional Activators in *Vibrio chlorae*" *Journal of Bacteriology*, 180(19):5256–5259, American Society for Microbiology.

Swartzman et al. (1992) "*Vibrio harveyi* RNA Polymerase: Purification and Resolution from Gyrase A" *Biochemistry Cell Biology*, 70:698–702.

O'Toole et al. (1997) "RpoN of the Fish Pathogen *Vibrio* (*Listonella*) *anguillarum* is Essential for Flagellum Production and Virulence by the Water–Borne but not Intraperitoneal Route of Inoculation" *Microbiology*, 143:3849–3859.

Ikegami et al. (2000) "Cloning and Characterization of the Gene Encoding RNA Polymerase Sigma Factor $\sigma^{54}$ of Deep–Sea Piezophilic *Shewanella violacea*" *Biochimica et Biophysica Acta*, 1491:315–320.

Kawagishi et al. (1997) "Cloning of *Vibrio alginolyticus* rpoN Gene that is Required for Polar Flagellar Formation" *Journal of Bacteriology*, 179(21):6851–6854, American Society for Microbiology.

Fuqua, Clay et al., Annual Review of Microbiology, vol. 50, pp. 727–751, 1996 (full text, dialog print out).

Genbank Accession No. Ae000353, dated Nov. 1, 1997, Autoinducer–2 production protein LuxS.

Gilson, L. et al., Journal of Bacteriology, vol. 177(23), pp. 6946–6951, Dec. 1995.

Jones, S. et al., The EMBO Journal, vol. 12(6), pp. 2477–2482, 1993.

Kuo et al., "Modulation of Luminescence Operon Expression by N–Octanoyl–L–Homoserine Lactone in ainS Mutants of *Vibrio fischerii*," *Journal of Bacteriology*, vol. 178, No. 4, Feb. 1996, pp. 971–976.

Lin, J. et al., Biochemical and Biophysical Research Communication, pp. 938–947, May 24, 1995, vol. 210(3).

Lin, J. et al., Biochemical and Biophysical Research Communications, vol. 219, pp. 868–875, 1996.

Pesci, E.C. et al. Journal of Bacteriology, vol. 179(10), pp. 3127–3132, May 1997.

Salmond, G.P.C. et al., Molecular Biology, vol. 16(4), pp. 615–624, 1995.

Sun, T.S.C. et al., Journal of AOAC International, vol. 76(4), pp. 893–898, 1993.

Swift, S. et al., Molecular Biology, vol. 10(3), pp. 511–520, 1993.

\* cited by examiner

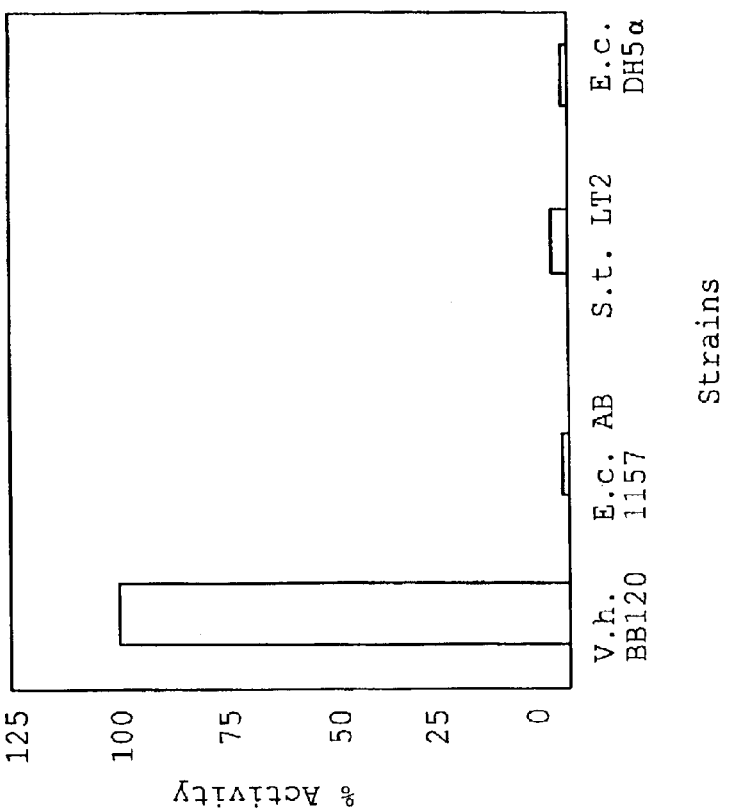
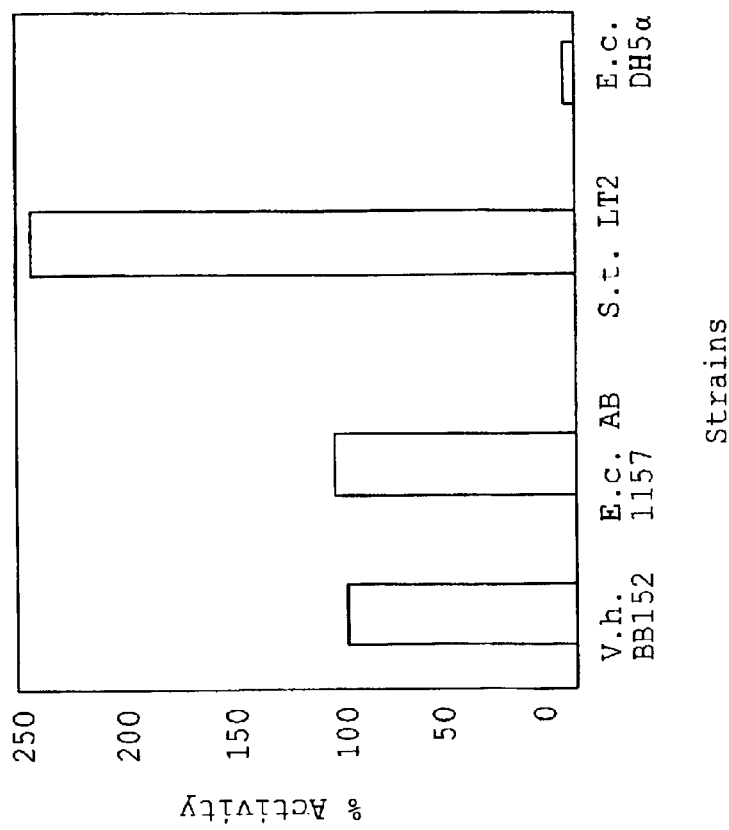
FIG. 1A
FIG. 1B

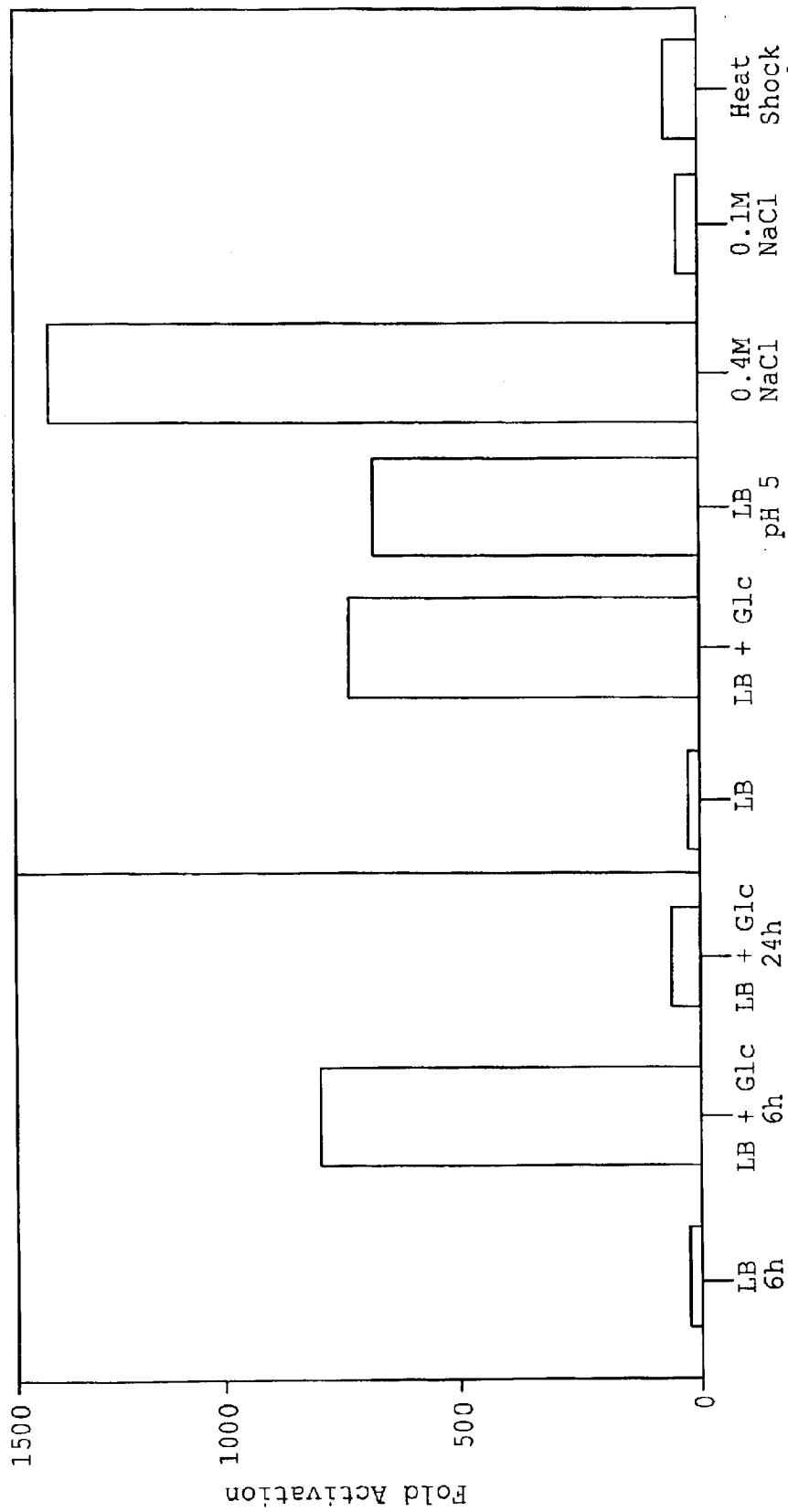

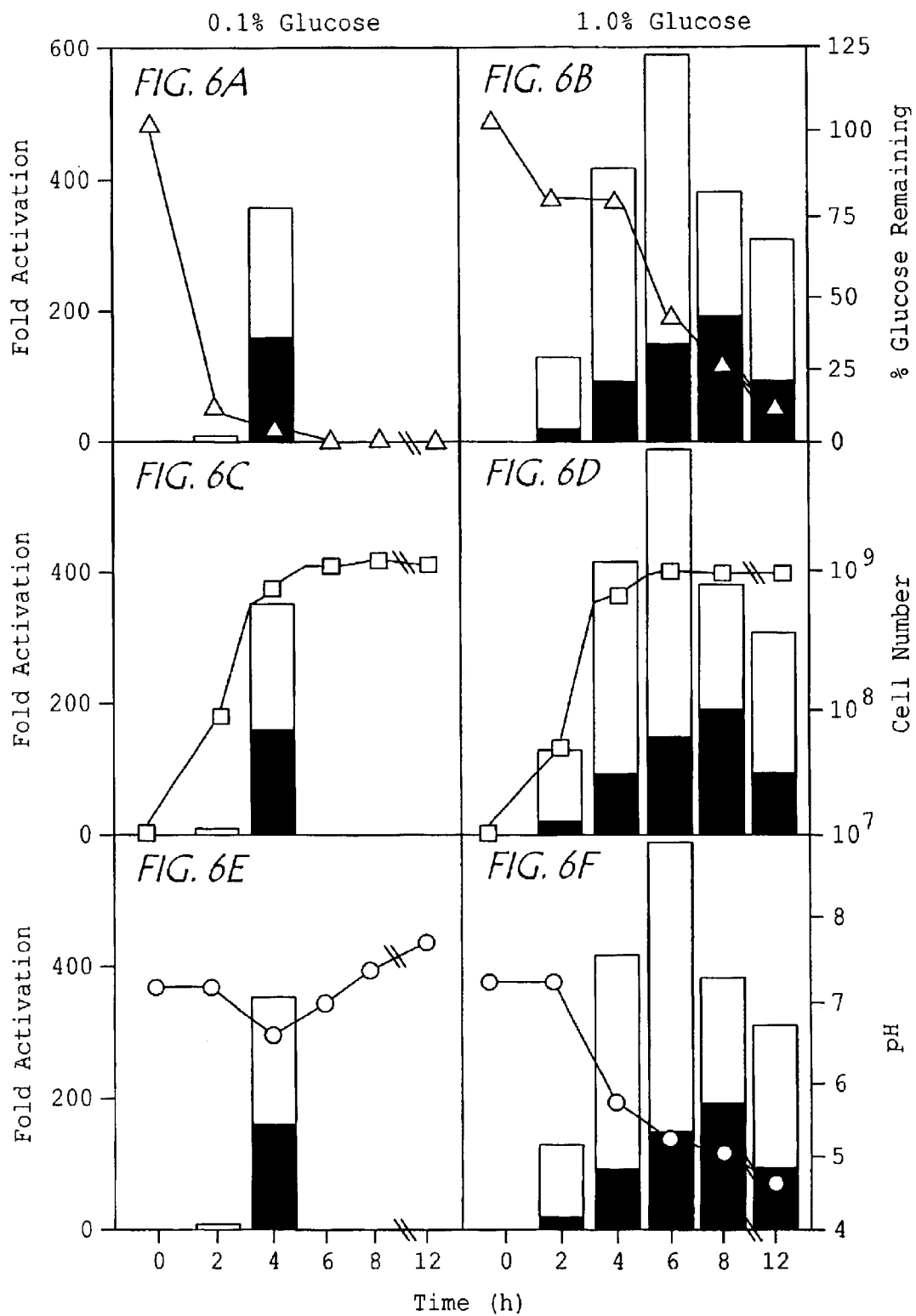

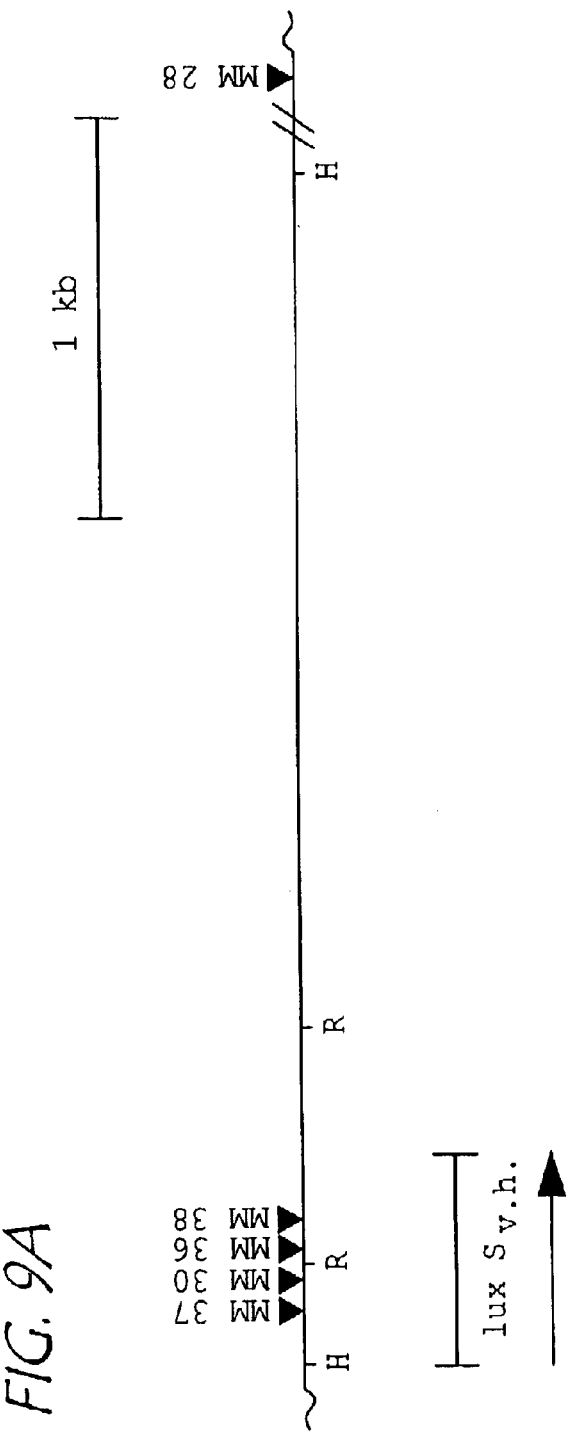

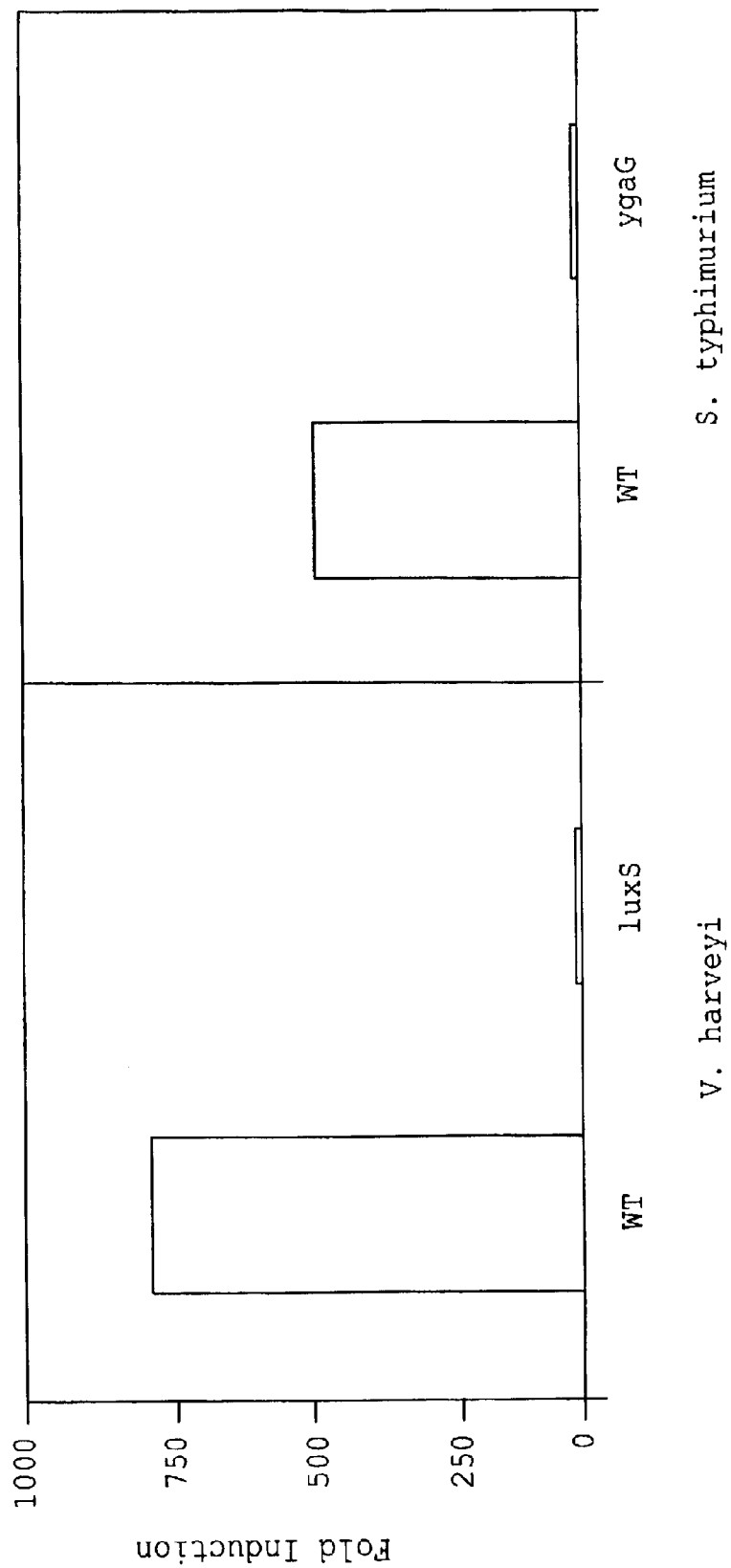

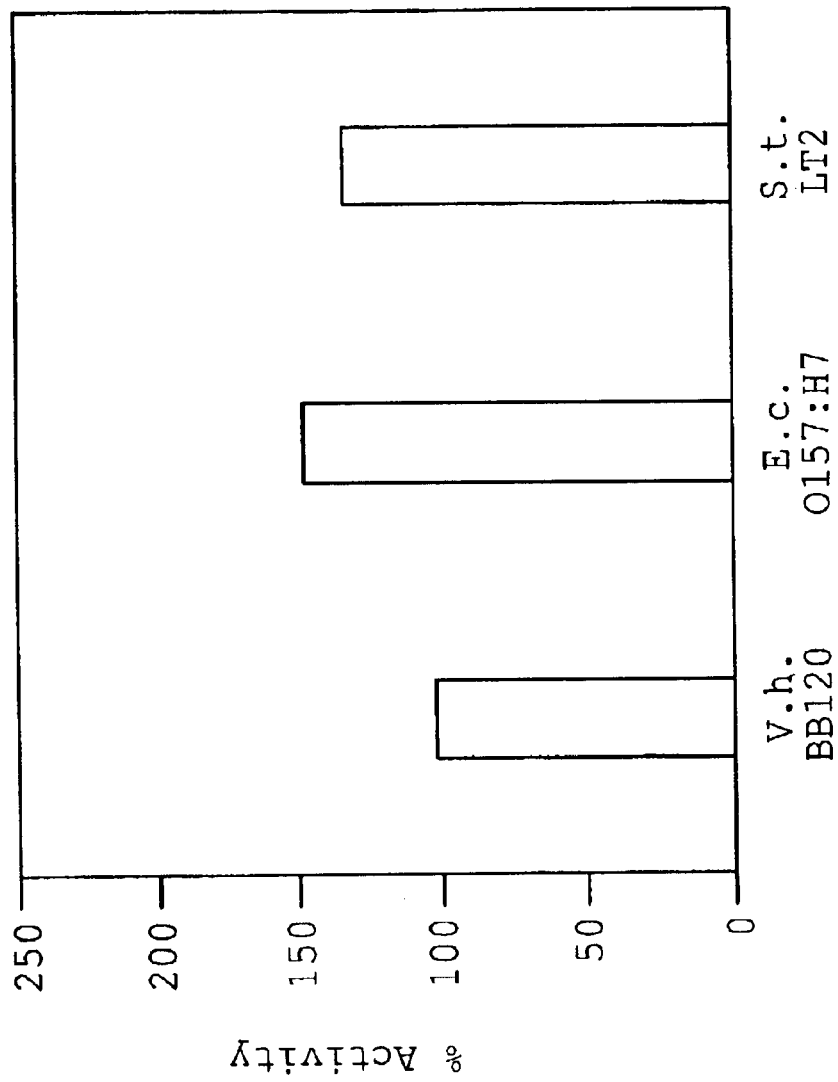

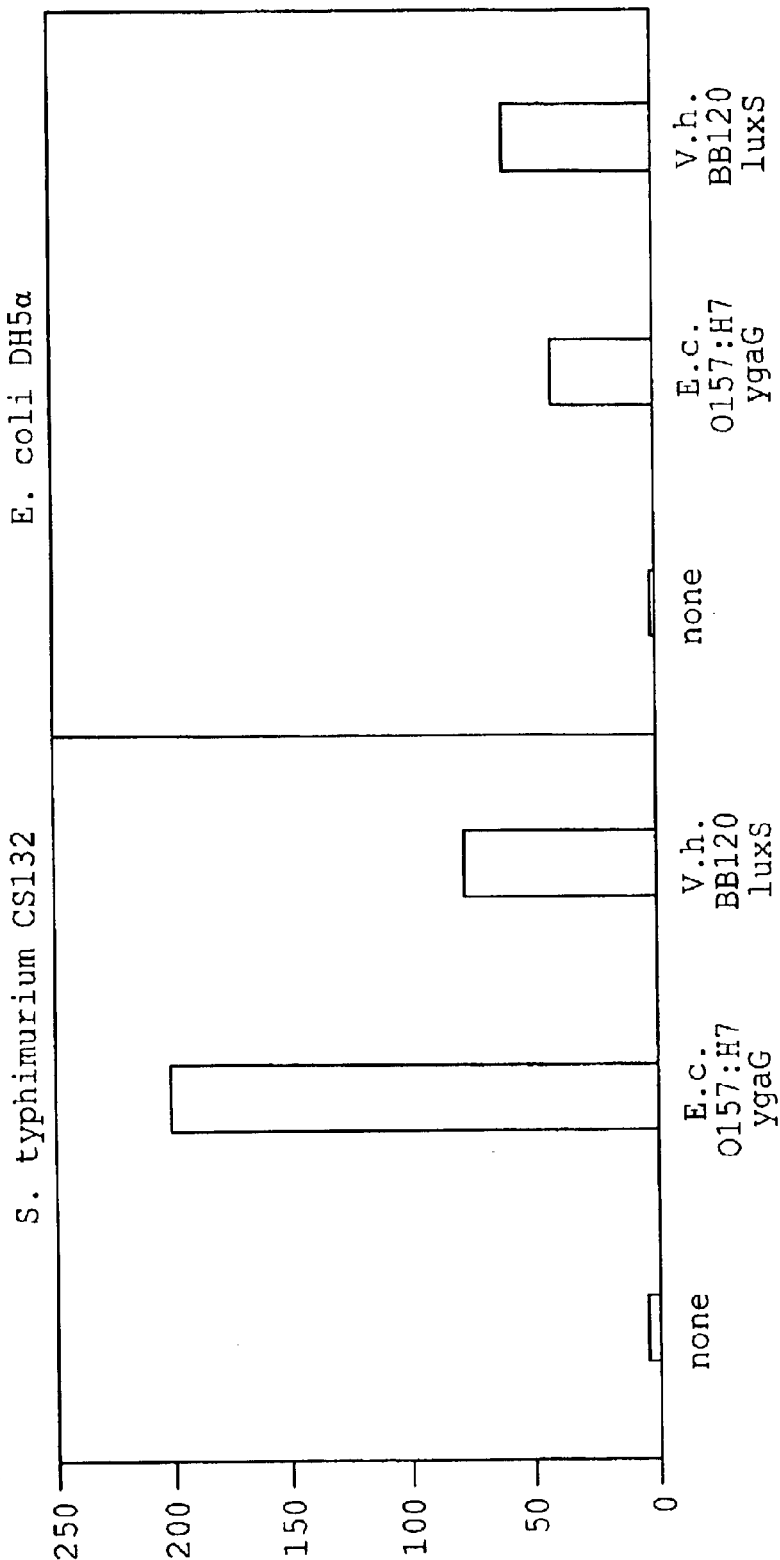

FIG. 12

```
V.h. BB120   1 MPLLDSFTVDHTRMMAPAVRVAKTMQTPRGDTITVFDLRFTAPNKDILSEKGIHTLEHLYAGFMRNHLNGDSVIIDISPMGCRTG
E.c. MG1655  1 MPLLDSFTVDHTRMEAPAVRVAKTMQTPMGDAITVFDLRFCVPNLEVMPERGIHTLEHLFAGFMRNHLNGNGVEIIDISPMGCRTG
E.c. O157:H7 1 MPLLDSFTVDHTRMEAPAVRVAKTMQTPMGDAITVFDLRFCVPNLEVMPERGIHTLEHLFAGFMRNHLNGNGVEIIDISPMGCRTG
S.t. LT2    1       NSDHTRMQAPAVRVAKTMQTPMGDAITVFDLRFCIPNKEVMPEKGIHTLEHLFAGFMRDHLNGNGVEIIDISPMGCRTG
E.c. DH5α    1 MPLLDSFTVDHTRMEAPAVRVAKTMQTPMGDAITVFDLRFCVPNLEVMPERGIHTLEHLFAGFMRNHLNGNGVEIIDISPMGCRTG

V.h. BB120   87 FYMSLIGTPSKQQVADAWIAAMEDVLKVENQNKIPELNEYQCGTAAMHSLDEAKQIAKNILEVGVAVNKNDELALPESMLREIRID
E.c. MG1655  87 FYMSLIGTPDKQRVADAWKAAMEDVLKVQDQNQIPELNVYQCGTYQMHSLQEAQDIARSILERDVRINSNEELALPKEKLQELHI
E.c. O157:H7 87 FYMSLIGTPDKQRVADAWKAAMEDVLKVQDQNQIPELNVYQCGTYQMHSLQEAQDIARSILERDVRINSNEELALPKEKLQELHI
S.t. LT2    87 FYMSLIGTPDKQRVADVWKAAMEDVLKVQDQNQIPELNVYQCGTYQMHSLQEAQDIARSILERDVRVNSNKELALPKEKLQELHI
E.c. DH5α   87 FYMSLIGTPDKQRVADAWKAAMADVLKVQDQNQIPELNVYQCGTYQMHSLSEAQDIARHILERDVRVNSNKELALPKEKLQELHI

E.c. DH5α   87 FYMSILVRQMSSVLLMPKGKRQWKTC
```

| Compund # | Compound Name | Conc. (Fold inhibition) | Active? | Structure |
|---|---|---|---|---|
| 15 | Cis-jasmone | 6ug/ml(52x) | y | 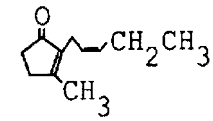 |
| 18 | 2-pentyl-2-cyclopenten-1-one | 6ug/ml(20x) | y | 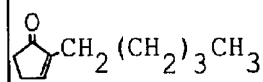 |
| 20 | 2-acetylcyclopentenone | 25ug/ml(6x) | y | 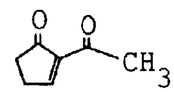 |
| 12 | Croconic Acid | 25ug/ml(29x) | y | 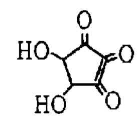 |
| 31 | B006 | 0.4ug/ml(9x) | y | 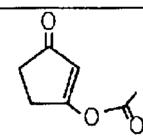 |
| 28 | 2-ethoxytetrahydrofuran | 100ug/ml(87x) | y | 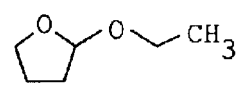 |
| 2 | 3-methyl-1,2-cyclopentanedione (2) | >=100ug/ml | y? | 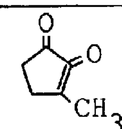 |
| 8 | 2,3,4,5 tetramethyl-2-cyclopentenone (8) | >=100ug/ml | y? | 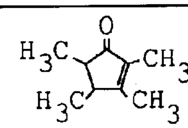 |
| 10 | 3-methyl-2-cyclopenten-1-one (10) | >=100ug/ml | y? | 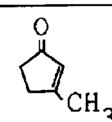 |
| 19 | 2-methyltetrahydrofuran-3-one (19) | >100ug/ml | n | 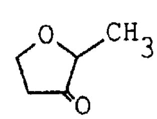 |
| 5 | 3-methoxy-2-cyclopenten-1-one (5) | >100ug/ml | n | 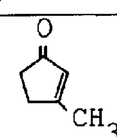 |

FIG. 19A

| | | | | |
|---|---|---|---|---|
| 6 | 3-ethyl-2-hydroxy-cyclopenten-1-one (6) | >100ug/ml | n | 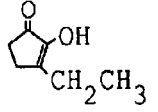 |
| 9 | 2,3-dimethyl-cyclopenten-1-one (9) | >100ug/ml | n | 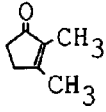 |
| 11 | 2-methyl-cyclopenten-1-one (11) | >100ug/ml | n | 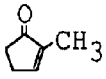 |
| 17 | alpha-hydroxy-gamma-butyrolactone (17) | >100ug/ml | n |  |
| 1 | 4,4-dimethyl-cyclopenten-1-one (1) | >100ug/ml | n | 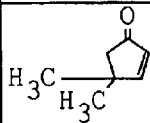 |
| 13 | D-erythronic gamma-lactone (13) | >100ug/ml | n | 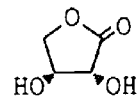 |
| 25 | (s)(+)dihydro-5-hydroxymethyl 2(3H)furanone (25) | >100ug/ml | n | 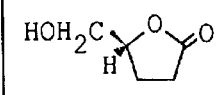 |
| 27 | methyltetrahydrofurfurylether (27) | >100ug/ml | n | 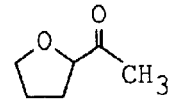 |
| 26 | R-(-)gamma-ethoxycarbonyl-gamma-butyrolactone | >100ug/ml | n | 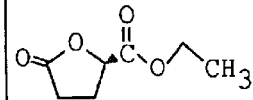 |
| 32C | 3-acetyl-4-cyclopenten-1-hydroxy | >100ug/ml | n | 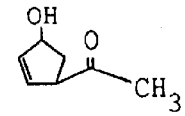 |
| 29 | 2,5-diethoxytetrahydrofuran | >100ug/ml | n |  |

FIG. 19B

| | | | | |
|---|---|---|---|---|
| 3 | 1,4 anhydroerythritol (3) | >100ug/ml | n | 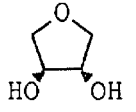 |
| 4 | 3-hydroxytetrahydrofuran (4) | >100ug/ml | n | 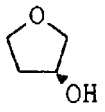 |
| 7 | (s)-(+)-3 hydroxytetrahydrofuran (7) | >100ug/ml | n | 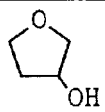 |
| 14 | 3-methyl 2,4-pentanedione (14) | >100ug/ml | n | 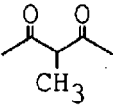 |
| 16 | 3-ethyl 2,4-pentanedione (16) | >100ug/ml | n | 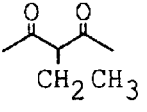 |
| 21 | 2 methyl-1,3 cyclopentanedione (21) | >100ug/ml | n | 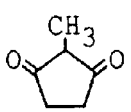 |
| 22 | (3AS)(7AS)-+-hexahydro-3Ahydroxy-7 Amethyl 1,5 indiandione (22) | >100ug/ml | n | 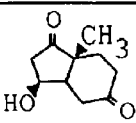 |
| 23 | 4-hydroxy-5-methyl-4-cyclopentene 1,3 dione monohydrate (23) | >100ug/ml | n | 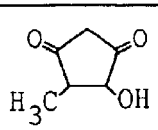 |
| 24 | 1,3 cyclopentanedione (24) | >100ug/ml | n | 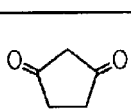 |
FIG. 19C

Group A Strep. Protease

SEQUENCE LISTING

<160> NUMBER OF SEQ ID NOS: 27

<210> SEQ ID NO 1
<211> LENGTH: 519
<212> TYPE: DNA
<213> ORGANISM: Vibrio harveyi

<400> SEQUENCE: 1

| | | | | | |
|---|---|---|---|---|---|
| atgcctttat | tagacagctt | taccgtagac | cacacgcgta | tgaatgcacc | agcggttcgt | 60 |
| gtggctaaaa | cgatgcaaac | tccaaaagga | gacaccatca | cggtattcga | cctacgtttc | 120 |
| actgctccaa | acaaagacat | cctttctgag | aaaggaattc | atacattaga | gcatttgtac | 180 |
| gcaggctttta | tgcgtaatca | cctaaatggt | gatagcgttg | agatcattga | tatctcacca | 240 |
| atggggtgcc | gtactggttt | ctacatgagc | ttgattggta | cgccttcaga | gcagcaagtg | 300 |
| gctgacgctt | ggattgccgc | gatggaagac | gtactaaaag | tagaaaacca | aaacaagatc | 360 |
| cctgagttga | acgaatacca | atgtggtaca | gcagcgatgc | actctctgga | tgaagcgaag | 420 |
| caaatcgcga | agaacattct | agaagtgggt | gtggcggtga | ataagaatga | tgaattggca | 480 |
| ctgccagagt | caatgctgag | agagctacgc | atcgactaa | | | 519 |

<210> SEQ ID NO 2
<211> LENGTH: 516
<212> TYPE: DNA
<213> ORGANISM: Escherichia coli

<400> SEQUENCE: 2

```
atgccgttgt tagatagctt cacagtcgat catacccgga tggaagcgcc tgcagttcgg      60
gtggcgaaaa caatgaacac cccgcatggc gacgcaatca ccgtgttcga tctgcgcttc     120
tgcgtgccga acaaagaagt gatgccagaa agagggatcc ataccctgga gcacctgttt     180
gctggtttta tgcgtaacca tcttaacggt aatggtgtag agattatcga tatctcgcca     240
atgggctgcc gcaccggttt ttatatgagt ctgattggta cgccagatga gcagcgtgtt     300
gctgatgcct ggaaagcggc aatggaagac gtgctgaaag tgcaggatca gaatcagatc     360
ccggaactga acgtctacca gtgtggcact taccagatgc actcgttgca ggaagcgcag     420
gatattgcgc gtagcattct ggaacgtgac gtacgcatca acagcaacga gaactggca     480
ctgccgaaag agaagttgca ggaactgcac atctag                               516
```

<210> SEQ ID NO 3
<211> LENGTH: 110
<212> TYPE: DNA
<213> ORGANISM: Salmonella typhimurium
<220> FEATURE:
<221> NAME/KEY: misc_feature
<222> LOCATION: (1)...(110)
<223> OTHER INFORMATION: sequence from MudJ

<400> SEQUENCE: 3

```
gatgtgctga aagtgcagga tcaaaaccag atcccggagc tgaacgttta ccagtgcggt      60
acgtatcaga tgcactcgct cagtgaagcg caggacattg cccgtcatat                110
```

<210> SEQ ID NO 4
<211> LENGTH: 492
<212> TYPE: DNA
<213> ORGANISM: Salmonella typhimurium

<400> SEQUENCE: 4

```
aattcggatc ataccggatg caagcgccgg cggtccgggt tgcaaaaacg atgaacaccc      60
cgcatggcga cgcaatcacg tgtttgatct gcgttttgc attccgaaca agaagtgat      120
gccggaaaaa gggattcata cgcttgagca tctgtttgct ggctttatgc gcgaccacct     180
caacggtaac ggcgttgaga ttatcgatat ctcgccgatg gctgccgca ccggctttta     240
catgagcctg attggcacgc cggacgagca gcgtgttgcc gacgcctgga aagcggcgat     300
ggcggatgtg ctgaaagtgc aggatcaaaa ccagatcccg gagctgaacg tttaccagtg     360
cggtacgtat cagatgcact cgctcagtga agcgcaggac attgcccgtc atattctgga     420
gcgtgatgtg cgcgtgaaca gcaataaaga gctggcgctg ccgaaagaaa aactgcagga     480
actgatattt ag                                                         492
```

<210> SEQ ID NO 5
<211> LENGTH: 504
<212> TYPE: DNA
<213> ORGANISM: Haemophilus influenzae

<400> SEQUENCE: 5

```
atgccattac ttgatagttt taaagtggat cacacaaaaa tgaacgcacc tgcagtacgc      60
```

-continued

```
attgcaaaaa cgatgctcac gccaaaaggc gataatatta ctgttttttga tttacgtttt      120 tgtattccaa acaaagaaat tctttcccca aaaggcattc atacacttga acatttattt      180
gctggattta tgcgcgatca tttaaatggc gatagcatag aaattattga tatttctccg      240
atgggatgtc gcacgggatt ttatatgtct ttgattggca caccaaatga acagaaagtg      300
tctgaggctt ggttagcttc aatgcaagat gttttaggtg tacaagatca agcttctatt      360
cctgaattaa atatctatca atgcggaagc tatacgaaac attccttaga agatgcacac      420
gaaattgcca aaaatgttat cgcacgcggt ataggtgtaa ataaaaatga agatttgtca      480
ctcgataatt ccttattaaa atag                                             504
```

<210> SEQ ID NO 6
<211> LENGTH: 468
<212> TYPE: DNA
<213> ORGANISM: Helicobacter pylori

<400> SEQUENCE: 6

```
atgaaaacac caaaaatgaa tgtagagagt tttaatttgg atcacaccaa agtcaaagcc       60
ccttatgtgc gtgtcgctga tcgcaaaaag ggcgttaatg gggatttgat tgtcaaatac      120
gatgtgcgct tcaagcagcc caaccaagat cacatggaca tgcctagcct acattcttta      180
gagcatttag tcgctgaaat tatccgcaac catgccagtt atgtcgtgga ttggtcgcct      240
atgggttgcc aaacgggatt ttatctcaca gtgttaaacc atgacaatta cacagagatt      300
ttagaggttt tagaaaagac catgcaagat gtgttaaagg ctacagaagt gcctgccagc      360
aatgaaaagc aatgcggttg gcggctaac cacactttag agggtgctaa ggatttagcg      420
cgcgcttttt tagacaaacg cgctgagtgg tctgaagtgg gggtttga                  468
```

<210> SEQ ID NO 7
<211> LENGTH: 482
<212> TYPE: DNA
<213> ORGANISM: Bacillus subtilis

<400> SEQUENCE: 7

```
atgccttcag tagaaagttt tgagcttgat cataatgcgg ttgttgctcc atatgtaaga       60
cattgcggcg tgcataaagt gggaacagac ggcgttgtaa ataaatttga cattcgtttt      120
tgccagccaa ataaacaggc gatgaagcct gacaccattc acacactcga gcatttgctc      180
gcgtttacga ttcgttctca cgctgagaaa tacgatcatt ttgatatcat tgatatttct      240
ccaatgggct gccagacagg ctattatcta gttgtgagcg gagagccgac atcagcggaa      300
atcgttgatc tgcttgaaga cacaatgaag gaagcggtag agattacaga aatacctgct      360
gcgaatgaaa agcagtgcgg ccaagcgaag cttcatgatc tggaaggcgc taaacgttta      420
atgcgtttct ggctttcaca ggataaagaa gaattgctaa aagtatttgg ctaaaataga      480
aa                                                                     482
```

<210> SEQ ID NO 8
<211> LENGTH: 537
<212> TYPE: DNA
<213> ORGANISM: Borrelia burdorferi

<400> SEQUENCE: 8

```
atgaatttga atgggaaaaa ttagatttg taaaaaaaat acaaacagcg ctaaaaaaat        60
gaaaaaaata acaagcttta caatagatca tacaaaactc aaccctggca tatatgtctc      120
aagaaaagat acctttgaaa atgtaatatt tactacaata gacattagaa tcaaagctcc      180
```

-continued

```
caacatcgaa ccaataattg aaaacgcagc aatacataca atagagcaca taggagctac    240
tttacttaga aataatgaag tttggaccga aaaatagta tattttggcc ctatgggatg    300
cagaactggt tttacttaa taattttttgg agactatgaa agtaaagatc ttgttgactt    360
agtctcatgg cttttttccg aaatcgtaaa ttttttcagaa cctatcccag gcgcaagtga    420
taaggaatgc ggaaattaca agaacataa ccttgatatg ctaaatatg aatcttctaa    480 atacttacaa atattaaaca atattaaaga agaaaattta aaatatcctt agctcat     537
```

<210> SEQ ID NO 9
<211> LENGTH: 519
<212> TYPE: DNA
<213> ORGANISM: Vibrio cholerae

<400> SEQUENCE: 9

```
atgccattat tagacagttt taccgtcgat catactcgta tgaatgcacc ggcggtgcgt     60
gttgccaaaa ccatgcaaac cccaaaaggg gatacgatta ccgtatttga tttgcgtttt    120
actatgccaa acaaagatat cttgtctgag cgcggtatcc atactctaga gcatctctac    180 gcgggctta tgcgcaatca ccttaacggc agccaagtgg agatcatcga tatttcacca    240
atgggttgcc gtacaggttt ctacatgagc ttgattggtg cgccgacaga acagcaagtg    300
gcacaagcat ggctagccgc aatgcaagat gtgttgaaag ttgaaagcca agagcaaatt    360
cctgagctga atgagtacca gtgcggcact gcggcgatgc actcgctcga gaagccaaa    420 gcgattgcga aaacgtgat gcggcaggc atctcggtta accgtaacga tgagttggcg    480
ctgcccgaat ctatgctcaa tgagctgaag gttcactaa                          519
```

<210> SEQ ID NO 10
<211> LENGTH: 172
<212> TYPE: PRT
<213> ORGANISM: Vibrio harveyi

<400> SEQUENCE: 10

```
Met Pro Leu Leu Asp Ser Phe Thr Val Asp His Thr Arg Met Asn Ala
 1               5                   10                  15

Pro Ala Val Arg Val Ala Lys Thr Met Gln Thr Pro Lys Gly Asp Thr
            20                  25                  30

Ile Thr Val Phe Asp Leu Arg Phe Thr Ala Pro Asn Lys Asp Ile Leu
        35                  40                  45

Ser Glu Lys Gly Ile His Thr Leu Glu His Leu Tyr Ala Gly Phe Met
    50                  55                  60

Arg Asn His Leu Asn Gly Asp Ser Val Glu Ile Ile Asp Ile Ser Pro
65                  70                  75                  80

Met Gly Cys Arg Thr Gly Phe Tyr Met Ser Leu Ile Gly Thr Pro Ser
                85                  90                  95

Glu Gln Gln Val Ala Asp Ala Trp Ile Ala Met Glu Asp Val Leu
            100                 105                 110

Lys Val Glu Asn Gln Asn Lys Ile Pro Glu Leu Asn Glu Tyr Gln Cys
        115                 120                 125

Gly Thr Ala Ala Met His Ser Leu Asp Glu Ala Lys Gln Ile Ala Lys
    130                 135                 140

Asn Ile Leu Glu Val Gly Val Ala Val Asn Lys Asn Asp Glu Leu Ala
145                 150                 155                 160

Leu Pro Glu Ser Met Leu Arg Glu Leu Arg Ile Asp
                165                 170
```

<210> SEQ ID NO 11
<211> LENGTH: 171
<212> TYPE: PRT
<213> ORGANISM: Escherichia coli

<400> SEQUENCE: 11

```
Met Pro Leu Leu Asp Ser Phe Thr Val Asp His Thr Arg Met Glu Ala
 1               5                  10                  15

Pro Ala Val Arg Val Ala Lys Thr Met Asn Thr Pro His Gly Asp Ala
             20                  25                  30

Ile Thr Val Phe Asp Leu Arg Phe Cys Val Pro Asn Lys Glu Val Met
         35                  40                  45

Pro Glu Arg Gly Ile His Thr Leu Glu His Leu Phe Ala Gly Phe Met
 50                  55                  60

Arg Asn His Leu Asn Gly Asn Gly Val Glu Ile Ile Asp Ile Ser Pro
65                  70                  75                  80

Met Gly Cys Arg Thr Gly Phe Tyr Met Ser Leu Ile Gly Thr Pro Asp
                 85                  90                  95

Glu Gln Arg Val Ala Asp Ala Trp Lys Ala Ala Met Glu Asp Val Leu
            100                 105                 110

Lys Val Gln Asp Gln Asn Gln Ile Pro Glu Leu Asn Val Tyr Gln Cys
        115                 120                 125

Gly Thr Tyr Gln Met His Ser Leu Gln Glu Ala Gln Asp Ile Ala Arg
    130                 135                 140

Ser Ile Leu Glu Arg Asp Val Arg Ile Asn Ser Asn Glu Glu Leu Ala
145                 150                 155                 160

Leu Pro Lys Glu Lys Leu Gln Glu Leu His Ile
                165                 170
```

<210> SEQ ID NO 12
<211> LENGTH: 164
<212> TYPE: PRT
<213> ORGANISM: Salmonella typhimurium

<400> SEQUENCE: 12

```
Asn Ser Asp His Thr Arg Met Gln Ala Pro Ala Val Arg Val Ala Lys
 1               5                  10                  15

Thr Met Asn Thr Pro His Gly Asp Ala Ile Thr Val Phe Asp Leu Arg
             20                  25                  30

Phe Cys Ile Pro Asn Lys Glu Val Met Pro Glu Lys Gly Ile His Thr
         35                  40                  45

Leu Glu His Leu Phe Ala Gly Phe Met Arg Asp His Leu Asn Gly Asn
 50                  55                  60

Gly Val Glu Ile Ile Asp Ile Ser Pro Met Gly Cys Arg Thr Gly Phe
65                  70                  75                  80

Tyr Met Ser Leu Ile Gly Thr Pro Asp Glu Gln Arg Val Ala Asp Ala
                 85                  90                  95

Trp Lys Ala Ala Met Ala Asp Val Leu Lys Val Gln Asp Gln Asn Gln
            100                 105                 110

Ile Pro Glu Leu Asn Val Tyr Gln Cys Gly Thr Tyr Gln Met His Ser
        115                 120                 125

Leu Ser Glu Ala Gln Asp Ile Ala Arg His Ile Leu Glu Arg Asp Val
    130                 135                 140

Arg Val Asn Ser Asn Lys Glu Leu Ala Leu Pro Lys Glu Lys Leu Gln
145                 150                 155                 160
```

Glu Thr Asp Ile

<210> SEQ ID NO 13
<211> LENGTH: 167
<212> TYPE: PRT
<213> ORGANISM: Haemophilus influenzae

<400> SEQUENCE: 13

Met Pro Leu Leu Asp Ser Phe Lys Val Asp His Thr Lys Met Asn Ala
1               5                   10                  15

Pro Ala Val Arg Ile Ala Lys Thr Met Leu Thr Pro Lys Gly Asp Asn
            20                  25                  30

Ile Thr Val Phe Asp Leu Arg Phe Cys Ile Pro Asn Lys Glu Ile Leu
        35                  40                  45

Ser Pro Lys Gly Ile His Thr Leu Glu His Leu Phe Ala Gly Phe Met
    50                  55                  60

Arg Asp His Leu Asn Gly Asp Ser Ile Glu Ile Asp Ile Ser Pro
65                  70                  75                  80

Met Gly Cys Arg Thr Gly Phe Tyr Met Ser Leu Ile Gly Thr Pro Asn
                85                  90                  95

Glu Gln Lys Val Ser Glu Ala Trp Leu Ala Ser Met Gln Asp Val Leu
            100                 105                 110

Gly Val Gln Asp Gln Ala Ser Ile Pro Glu Leu Asn Ile Tyr Gln Cys
        115                 120                 125

Gly Ser Tyr Thr Glu His Ser Leu Glu Asp Ala His Glu Ile Ala Lys
    130                 135                 140

Asn Val Ile Ala Arg Gly Ile Gly Val Asn Lys Asn Glu Asp Leu Ser
145                 150                 155                 160

Leu Asp Asn Ser Leu Leu Lys
                165

<210> SEQ ID NO 14
<211> LENGTH: 155
<212> TYPE: PRT
<213> ORGANISM: Helicobacter pylori

<400> SEQUENCE: 14

Met Lys Thr Pro Lys Met Asn Val Glu Ser Phe Asn Leu Asp His Thr
1               5                   10                  15

Lys Val Lys Ala Pro Tyr Val Arg Val Ala Asp Arg Lys Lys Gly Val
            20                  25                  30

Asn Gly Asp Leu Ile Val Lys Tyr Asp Val Arg Phe Lys Gln Pro Asn
        35                  40                  45

Gln Asp His Met Asp Met Pro Ser Leu His Ser Leu Glu His Leu Val
    50                  55                  60

Ala Glu Ile Ile Arg Asn His Ala Ser Tyr Val Val Asp Trp Ser Pro
65                  70                  75                  80

Met Gly Cys Gln Thr Gly Phe Tyr Leu Thr Val Leu Asn His Asp Asn
                85                  90                  95

Tyr Thr Glu Ile Leu Glu Val Leu Glu Lys Thr Met Gln Asp Val Leu
            100                 105                 110

Lys Ala Thr Glu Val Pro Ala Ser Asn Glu Lys Gln Cys Gly Trp Ala
        115                 120                 125

Ala Asn His Thr Leu Glu Gly Ala Lys Asp Leu Ala Arg Ala Phe Leu
    130                 135                 140

```
Asp Lys Arg Ala Glu Trp Ser Glu Val Gly Val
145                 150                 155

<210> SEQ ID NO 15
<211> LENGTH: 157
<212> TYPE: PRT
<213> ORGANISM: Bacillus subtilis

<400> SEQUENCE: 15

Met Pro Ser Val Glu Ser Phe Glu Leu Asp His Asn Ala Val Val Ala
1               5                   10                  15

Pro Tyr Val Arg His Cys Gly Val His Lys Val Gly Thr Asp Gly Val
            20                  25                  30

Val Asn Lys Phe Asp Ile Arg Phe Cys Gln Pro Asn Lys Gln Ala Met
        35                  40                  45

Lys Pro Asp Thr Ile His Thr Leu Glu His Leu Leu Ala Phe Thr Ile
    50                  55                  60

Arg Ser His Ala Glu Lys Tyr Asp His Phe Asp Ile Ile Asp Ile Ser
65                  70                  75                  80

Pro Met Gly Cys Gln Thr Gly Tyr Tyr Leu Val Val Ser Gly Glu Pro
                85                  90                  95

Thr Ser Ala Glu Ile Val Asp Leu Leu Glu Asp Thr Met Lys Glu Ala
            100                 105                 110

Val Glu Ile Thr Glu Ile Pro Ala Ala Asn Glu Lys Gln Cys Gly Gln
        115                 120                 125

Ala Lys Leu His Asp Leu Glu Gly Ala Lys Arg Leu Met Arg Phe Trp
    130                 135                 140

Leu Ser Gln Asp Lys Glu Glu Leu Leu Lys Val Phe Gly
145                 150                 155

<210> SEQ ID NO 16
<211> LENGTH: 173
<212> TYPE: PRT
<213> ORGANISM: Borrelia burgdorferi

<400> SEQUENCE: 16

Met Gly Lys Ile Arg Phe Cys Lys Lys Asn Thr Asn Ser Ala Lys Lys
1               5                   10                  15

Met Lys Lys Ile Thr Ser Phe Thr Ile Asp His Thr Lys Leu Asn Pro
            20                  25                  30

Gly Ile Tyr Val Ser Arg Lys Asp Thr Phe Glu Asn Val Ile Phe Thr
        35                  40                  45

Thr Ile Asp Ile Arg Ile Lys Ala Pro Asn Ile Glu Pro Ile Ile Glu
    50                  55                  60

Asn Ala Ala Ile His Thr Ile Glu His Ile Gly Ala Thr Leu Leu Arg
65                  70                  75                  80

Asn Asn Glu Val Trp Thr Glu Lys Ile Val Tyr Phe Gly Pro Met Gly
                85                  90                  95

Cys Arg Thr Gly Phe Tyr Leu Ile Ile Phe Gly Asp Tyr Glu Ser Lys
            100                 105                 110

Asp Leu Val Asp Leu Val Ser Trp Leu Phe Ser Glu Ile Val Asn Phe
        115                 120                 125

Ser Glu Pro Ile Pro Gly Ala Ser Asp Lys Glu Cys Gly Asn Tyr Lys
    130                 135                 140

Glu His Asn Leu Asp Met Ala Lys Tyr Glu Ser Ser Lys Tyr Leu Gln
145                 150                 155                 160
```

```
Ile Leu Asn Asn Ile Lys Glu Glu Asn Leu Lys Tyr Pro
            165                 170
```

<210> SEQ ID NO 17
<211> LENGTH: 172
<212> TYPE: PRT
<213> ORGANISM: Vibrio cholerae

<400> SEQUENCE: 17

```
Met Pro Leu Leu Asp Ser Phe Thr Val Asp His Thr Arg Met Asn Ala
 1               5                  10                  15

Pro Ala Val Arg Val Ala Lys Thr Met Gln Thr Pro Lys Gly Asp Thr
            20                  25                  30

Ile Thr Val Phe Asp Leu Arg Phe Thr Met Pro Asn Lys Asp Ile Leu
        35                  40                  45

Ser Glu Arg Gly Ile His Thr Leu Glu His Leu Tyr Ala Gly Phe Met
    50                  55                  60

Arg Asn His Leu Asn Gly Ser Gln Val Glu Ile Ile Asp Ile Ser Pro
65                  70                  75                  80

Met Gly Cys Arg Thr Gly Phe Tyr Met Ser Leu Ile Gly Ala Pro Thr
                85                  90                  95

Glu Gln Gln Val Ala Gln Ala Trp Leu Ala Ala Met Gln Asp Val Leu
            100                 105                 110

Lys Val Glu Ser Gln Glu Gln Ile Pro Glu Leu Asn Glu Tyr Gln Cys
        115                 120                 125

Gly Thr Ala Ala Met His Ser Leu Glu Glu Ala Lys Ala Ile Ala Lys
    130                 135                 140

Asn Val Ile Ala Ala Gly Ile Ser Val Asn Arg Asn Asp Glu Leu Ala
145                 150                 155                 160

Leu Pro Glu Ser Met Leu Asn Glu Leu Lys Val His
                165                 170
```

<210> SEQ ID NO 18
<211> LENGTH: 32
<212> TYPE: DNA
<213> ORGANISM: Artificial Sequence
<220> FEATURE:
<223> OTHER INFORMATION: oligonucleotide primer for fts Q1P promoter

<400> SEQUENCE: 18
cggagatctg cgctttcaat ggataaacta cg                           32

<210> SEQ ID NO 19
<211> LENGTH: 30
<212> TYPE: DNA
<213> ORGANISM: Artificial Sequence
<220> FEATURE:
<223> OTHER INFORMATION: oligonucleotide primer for fts Q2P promoter

<400> SEQUENCE: 19
cgcggatcct cttcttcgct gtttcgcgtg                              30

<210> SEQ ID NO 20
<211> LENGTH: 36
<212> TYPE: DNA
<213> ORGANISM: Artificial Sequence
<220> FEATURE:
<223> OTHER INFORMATION: oligonucleotide primer
<220> FEATURE:
<221> NAME/KEY: misc_feature
<222> LOCATION: (1)...(36)
<223> OTHER INFORMATION: n = A,T,C or G

```
<400> SEQUENCE: 20
ggccacgcgt cgactagtac nnnnnnnnnn acgccc                                    36

<210> SEQ ID NO 21
<211> LENGTH: 21
<212> TYPE: DNA
<213> ORGANISM: Artificial Sequence
<220> FEATURE:
<223> OTHER INFORMATION: MudJ specific oligonucleotide primer

<400> SEQUENCE: 21
gcactacagg cttgcaagcc c                                                    21

<210> SEQ ID NO 22
<211> LENGTH: 20
<212> TYPE: DNA
<213> ORGANISM: Artificial Sequence
<220> FEATURE:
<223> OTHER INFORMATION: arbitrary oligonucleotide primer

<400> SEQUENCE: 22
ggccacgcgt cgactagtca                                                      20

<210> SEQ ID NO 23
<211> LENGTH: 20
<212> TYPE: DNA
<213> ORGANISM: Artificial Sequence
<220> FEATURE:
<223> OTHER INFORMATION: MudJ specific oligonucleotide primer

<400> SEQUENCE: 23
tctaatccca tcagatcccg                                                      20

<210> SEQ ID NO 24
<211> LENGTH: 25
<212> TYPE: DNA
<213> ORGANISM: Artificial Sequence
<220> FEATURE:
<223> OTHER INFORMATION: oligonucleotide primer

<400> SEQUENCE: 24
gtgaagcttg tttactgact agatc                                                25

<210> SEQ ID NO 25
<211> LENGTH: 25
<212> TYPE: DNA
<213> ORGANISM: Artificial Sequence
<220> FEATURE:
<223> OTHER INFORMATION: oligonucleotide primer

<400> SEQUENCE: 25
gtgtctagaa aaacacgcct gacag                                                25

<210> SEQ ID NO 26
<211> LENGTH: 171
<212> TYPE: PRT
<213> ORGANISM: Escherichia coli

<400> SEQUENCE: 26
```

Met Pro Leu Leu Asp Ser Phe Thr Val Asp His Thr Arg Met Glu Ala
 1               5                  10                  15

Pro Ala Val Arg Val Ala Lys Thr Met Asn Thr Pro His Gly Asp Ala
            20                  25                  30

-continued

```
Ile Thr Val Phe Asp Leu Arg Phe Cys Val Pro Asn Lys Glu Val Met
        35                  40                  45

Pro Glu Arg Gly Ile His Thr Leu Glu His Leu Phe Ala Gly Phe Met
    50                  55                  60

Arg Asn His Leu Asn Gly Asn Gly Val Glu Ile Ile Asp Ile Ser Pro
65                  70                  75                  80

Met Gly Cys Arg Thr Gly Phe Tyr Met Ser Leu Ile Gly Thr Pro Asp
                85                  90                  95

Glu Gln Arg Val Ala Asp Ala Trp Lys Ala Ala Met Glu Asp Val Leu
                100                 105                 110

Lys Val Gln Asp Gln Asn Gln Ile Pro Glu Leu Asn Val Tyr Gln Cys
            115                 120                 125

Gly Thr Tyr Gln Met His Ser Leu Gln Glu Ala Gln Asp Ile Ala Arg
            130                 135                 140

Ser Ile Leu Glu Arg Asp Val Arg Ile Asn Ser Asn Glu Glu Leu Ala
145                 150                 155                 160

Leu Pro Lys Glu Lys Leu Gln Glu Leu His Ile
                165                 170
```

<210> SEQ ID NO 27
<211> LENGTH: 111
<212> TYPE: PRT
<213> ORGANISM: Escherichia coli

<400> SEQUENCE: 27

```
Met Pro Leu Leu Asp Ser Phe Thr Val Asp His Thr Arg Met Glu Ala
1               5                   10                  15

Pro Ala Val Arg Val Ala Lys Thr Met Asn Thr Pro His Gly Asp Ala
                20                  25                  30

Ile Thr Val Phe Asp Leu Arg Phe Cys Val Pro Asn Lys Glu Val Met
        35                  40                  45

Pro Glu Arg Gly Ile His Thr Leu Glu His Leu Phe Ala Gly Phe Met
    50                  55                  60

Arg Asn His Leu Asn Gly Asn Gly Val Glu Ile Ile Asp Ile Ser Pro
65                  70                  75                  80

Met Gly Cys Arg Thr Gly Phe Tyr Met Ser Leu Leu Val Arg Gln Met
                85                  90                  95

Ser Ser Val Leu Leu Met Pro Gly Lys Arg Gln Trp Lys Thr Cys
            100                 105                 110
```

COMPOUNDS AND METHODS FOR REGULATING BACTERIAL GROWTH AND PATHOGENESIS

RELATED APPLICATION INFORMATION

This application is a divisional of U.S. patent application Ser. No. 09/853,832, filed May 10, 2001, now U.S. Pat. No. 6,559,176, which claims priority to U.S. Provisional Application No. 60/203,000, filed May 10, 2000 and U.S. Provisional Application No. 60/254,398, filed Dec. 7, 2000, and U.S. Provisional Application No. 60/202,999, filed May 10, 2000, all of which are herein incorporated by reference.

STATEMENT OF GOVERNMENT INTEREST

The U.S. Government has certain rights in this invention, which was made in part with funds from the National Science Foundation, Grant No. MCB-9506033.

BACKGROUND OF THE INVENTION

1. Field of the Invention

This invention relates to bacterial diseases of humans and other mammals. In particular, the invention provides a novel signaling factor involved in regulating bacterial growth and pathogenesis, analogs and derivatives of the signaling factor, and methods for controlling bacterial growth and pathogenesis through use of such analogs and derivatives.

2. Background of the Invention

Intercellular cooperation confers a considerable advantage on multicellular organisms that was thought to be unavailable to unicellular organisms such as prokaryotes. Research in the last twenty years has revealed, however, that prokaryotes can communicate with each other in a way that modulates gene expression, and thereby can reap benefits that would otherwise be exclusive to eukaryotes. This ability was discovered in luminous marine bacteria such as *Vibrio fischeri* and *Vibrio harveyi*, which activate the expression of genes involved in light production only when their population density exceeds a critical value. This phenomenon, known as quorum-sensing, is now recognized as a general mechanism for gene regulation in many Gram-negative bacteria, and it allows them to perform in unison such activities as bioluminescence, swarming, biofilm formation, production of proteolytic enzymes, synthesis of antibiotics, development of genetic competence, plasmid conjugal transfer, and sporulation.

Quorum-sensing bacteria fall into two classes, depending on how many density-sensing systems they have. Both classes synthesize, release, and respond to signaling molecules called autoinducers to control gene expression as a function of cell density. Bacteria in the larger class use acyl-homoserine lactone signals in a single density-sensing system, with one gene that encodes an autoinducer synthase, and another that encodes a transcriptional activator protein that mediates response to the autoinducer. These genes are homologous to luxI and luxR of *V. fischeri*, respectively (Bassler and Silverman, in *Two component Signal Transduction*, Hoch et al., eds, Am. Soc. Microbiol. Washington D.C., pp 431–435, 1995).

Many bacteria that use the autoinducer-1 signaling factor associate with higher organisms, i.e., plants and animals, at some point during their lifecycles. For example, *Pseudomonas aeruginosa*, an opportunistic pathogen in humans with cystic fibrosis, regulates various virulence determinants with autoinducer-1. Other examples of autoinducer-1-producing bacteria include *Erwinia carotovora, Pseudomonas aureofaciens, Yersinia enterocolitica, Vibrio harveyi*, and *Agrobacterium tumefaciens*. *E. carotovora* infects certain plants and creates enzymes that degrade the plant's cell walls, resulting in what is called "soft rot disease." *Yersinia enterocolitica* causes gastrointestinal disease in humans and reportedly produces an autoinducer. *P. aureofaciens* synthesizes antibiotics under autoinducer control that block fungus growth in the roots.

Bacteria of the other class, exemplified by *V. harveyi*, have not one but two independent density-sensing systems. *V. harveyi* apparently uses the more species-specific Signaling System 1 for intra-species communication, and the less species-selective Signaling System 2 for inter-species communication (Bassler et al., J. Bacteriol. 179: 4043–4045, 1997). Each system comprises a sensor-autoinducer pair; Signaling System 1 uses Sensor 1 and autoinducer-1 (AI-1), while Signaling System 2 uses Sensor 2 and autoinducer-2 (AI-2) (Bassler et al., Mol. Microbiol. 13: 273–286, 1994). While autoinducer-1 is N-(3-hydroxy butanoyl)-L-homoserine lactone (HSL) (see Bassler et al., Mol. Microbiol. 9: 773–786, 1993), the structure of autoinducer-2 has not been established, nor have the gene(s) involved in its biosynthesis been identified.

Recent research indicates that quorum-sensing takes place not only among luminous marine bacteria, but also among pathogenic bacteria, where it regulates the production of virulence factors that are critical factors in bacterial pathogenesis. Thus, it would be an advance in the art to identify and characterize compounds with autoinducer-2 activity and the genes encoding the proteins required for production of the naturally-occurring autoinducer-2. Such an advance would provide a way to identify compounds useful for controlling pathogenic bacteria, a way to augment traditional antibiotic treatments, and a new target for the development of new antimicrobial agents.

SUMMARY OF THE INVENTION

The applicants have now discovered that many bacteria, including some non-luminous pathogens, secrete a signaling molecule that mimics *V. harveyi* autoinducer-2 in its function and physical properties. Bacteria that produce the AI-2 signaling factor of the invention include *Vibrio harveyi, Vibrio cholerae, Vibrio parahaemolyticus, Vibrio alginolyticus, Pseudomonas phosphoreum, Yersinia enterocolitica, Escherichia coli, Salmonella typhimurium, Haemophilus influenzae, Helicobacter pylor, Bacillus subtilis, Borrelia burgfdorferi, Neisseria meningitidis, Neisseria gonorrhoeae, Yersinia pestis, Campylobacter jejuni, Deinococcus radiodurans, Mycobacterium tuberculosis, Enterococcus faecalis, Streptococcus pneumoniae, Streptococcus pyogenes* and *Staphylococcus aureus*.

Free-living bacteria produce this novel signaling molecule only upon shifting to a colonizing, and therefore potentially pathogenic, existence in a host organism. Thus, in addition to stimulating luminescence genes in *V. harveyi*, the signaling molecule is expected to stimulate genes related to pathogenesis in bacteria that produce it. In addition to a purified molecule with autoinducer-2 signaling activity, the invention provides a synthetic form of the molecule and derivatives of it that regulate bacterial growth and pathogenesis.

In another aspect, there is provided a method for regulating the activity of an autoinducer-2 receptor comprising contacting an autoinducer-2 receptor with an AI-2 agonist or antagonist compound.

In another aspect, the invention provides a method of regulating autoinducer-2 activity by contacting a bacterial cell comprising autoinducer-2, or extract thereof, with a compound of structure I, II, III or IV.

In yet another aspect, the invention provides a method for regulating autoinducer-2 receptor activity by contacting an autoinducer-2 receptor with a compound of structure I, II, III or IV.

In another aspect, the invention provides a method for controlling bacterial growth or virulence by identifying a subject infected with an autoinducer-2-producing bacterium and administering to the subject a compound of structure I, II, III or IV.

In yet another aspect, the invention provides a method for inhibiting bacterial growth or virulence in a subject, by identifying a subject in which bacteria are producing autoinducer-2 and administering to the subject an inhibitor of an autoinducer-2 of the present invention.

In another aspect, the invention provides a method for identifying a compound that regulates the activity of autoinducer-2 by comparing the activity of autoinducer-2 obtained in the presence of the compound to that obtained in its absence.

In another aspect, the invention provides a method for identifying an autoinducer analog by contacting a cell, or cell extract, that produces a detectable amount of light in response to an autoinducer with the autoinducer analog and comparing the amount of light produced in the presence and the absence of the autoinducer analog.

In another aspect, the invention provides a method for identifying a compound that regulates the production or activity of autoinducer-2 by contacting with the compound a cell that produces autoinducer-2, and determining whether autoinducer-2 activity is present in the cell.

In another aspect, the invention provides a method for identifying a compound that affects binding of autoinducer-2 to an autoinducer-2 receptor by: (a) contacting autoinducer-2 and the autoinducer-2 receptor with the compound; (b) contacting (a) with a cell, or cell extract, that produces light in response to autoinducer-2 binding to the autoinducer-2 receptor; and (c) measuring the effect of the compound on light production.

In yet another aspect, the invention provides a method for identifying a compound that affects autoinducer-2 binding to an autoinducer-2 receptor by: (a) contacting with the compound a complex formed between autoinducer-2 and the autoinducer-2 receptor to allow dissociation of the complex; (b) contacting (a) with a cell, or cell extract thereof, that produces light in response to binding of autoinducer-2 to the autoinducer-2 receptor; and (c) measuring the effect of the compound on light production.

In yet another aspect, the invention provides a method for regulating expression of a siderophore in a bacterial cell by contacting a cell capable of producing the siderophore with a compound of structure I, II, III or IV.

In another aspect, the invention provides a method for regulating exopolysaccharide production in a cell by contacting a cell capable of producing an exopolysaccharide with a compound of structure I, II, III or IV.

In another aspect, the invention provides a method for regulating bacterial colony morphology by contacting a bacterial colony with a compound of structure I, II, III or IV.

In another aspect, the invention provides a method for regulating bacterial biofilm formation by contacting a bacterium capable of biofilm formation with any combination of compounds set forth in structures I–IV.

In another aspect, the invention provides a method for producing autoinducer-2 by contacting S-adenosylhomocysteine (SAH) with a LuxS protein.

In another aspect, the invention further provides a method for producing autoinducer-2 by; a) contacting S-adenosylhomocysteine (SAH) with a 5'-methylthioadenosine/S-adenosylhomocysteine nucleosidase (pfs) protein to form S-ribosylhomocysteine; b) contacting the S-ribosylhomocysteine from a) with a LuxS protein to promote the conversion of S-ribosylhomocysteine to autoinducer-2.

In yet another aspect, the invention further provides a method for detecting an autoinducer-associated biomarker by: (a) contacting at least one cell with an autoinducer to promote induction of a biomarker; and (b) detecting the biomarker.

In another aspect, the invention provides a method for regulating bacterial cell growth or expression of a virulence factor comprising contacting a bacterial cell with an isolated autoinducer-2 analog comprising the structure:

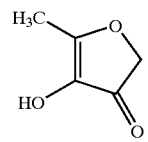

The invention further provides a synergistic antibiotic composition comprising an antibiotic and an inhibitor of the quorum-sensing pathway of a microorganism.

The invention further provides a medical device comprising a synergistic antibiotic composition comprising an antibiotic and an inhibitor of the quorum-sensing pathway of a microorganism, as well as a method of treating infections in a warm-blooded animal caused by microorganisms possessing a quorum-sensing mechanism, comprising administering to the animal a therapeutically effective amount of the synergistic antibiotic composition.

The invention further provides a pharmaceutical composition comprising a synergistic antibiotic composition comprising an antibiotic and an inhibitor of a quorum-sensing pathway of a microorganism or a pharmaceutically acceptable salt thereof and one or more pharmaceutically acceptable carriers, adjuvants or vehicles.

The invention also provides a method of treating infections in a warm-blooded animal caused by microorganisms possessing a quorum-sensing mechanism that comprises administering to the animal a therapeutically effective amount of the synergistic antibiotic composition comprising an antibiotic and an inhibitor of the quorum-sensing pathway of a microorganism.

The invention further provides a method for inhibiting biofilm formation by contacting a bacterium capable of biofilm formation with a compound having the structure set forth in structure III or structure IV.

The invention further provides a medical device comprising at least one antimicrobial compound having the structure set forth in structure III or structure IV, where the device is supplemented with the compound and the compound is present in a concentration sufficient to provide a localized antimicrobial effect.

The invention further provides a medical device comprising at least one synergistic antibiotic composition of an antibiotic and an inhibitor of the quorum-sensing pathway of a microorganism, where the composition is present in a concentration sufficient to provide a localized antimicrobial effect.

The invention further provides a medical device comprising at least one pharmaceutical composition comprising a synergistic antibiotic composition comprising an antibiotic and an inhibitor of a quorum-sensing pathway of a microorganism or a pharmaceutically-acceptable salt thereof and one or more pharmaceutically acceptable carriers, adjuvants or vehicles, wherein the composition is present in a concentration sufficient to provide a localized anti-microbial effect.

Additional features and advantages of the present invention will be better understood by reference to the drawings, detailed description and examples that follow.

BRIEF DESCRIPTION OF THE DRAWINGS

FIG. 1. Signaling substance from E. coli AB1157 and S. typhimurium LT2 cell-free culture fluids that induces luminescence in V. harveyi. The responses of V. harveyi reporter strains BB170 (Sensor 1⁻, Sensor 2⁺) (FIG. 1A), and BB886 (Sensor 1⁺, Sensor 2⁻) (FIG. 1B) to signaling substances present in cell-free culture fluids from E. coli, S. typhimurium and V. harveyi strains are shown. A bright culture of each reporter strain was diluted 1:5000 into fresh medium, and the light production per cell was then measured during the growth of the diluted culture. Cell-free culture fluids or sterile growth medium were added at a final concentration of 10% (v/v) at the start of the experiment. The data for the 5-hour time point are shown and are presented as the percent of the activity obtained when V. harveyi cell-free spent culture fluids are added. Abbreviations used for the different strains are: V.h; *Vibrio harveyi*, S.t; *Salmonella typhimurium*, and E.c; *Escherichia coli*.

FIG. 5. Conditions affecting autoinducer production in S. typhimurium. S. typhimurium LT2 was subjected to a variety of treatments after which cell-free culture fluids or osmotic shock fluids were prepared. These preparations were added to a diluted culture of the V. harveyi AI-2 reporter strain BB170 at 10% (v/v) and light output was measured thereafter. Fold activation is the level of light produced by the reporter following addition of the specified S. typhimurium preparation divided by the light output of the reporter when growth medium alone was added. The bars in FIG. 5A represent cell-free fluids prepared from S. typhimurium after the following treatments: LB 6 h; 6 h growth in LB at 30° C., LB+Glc 6 h; 6 h growth in LB+0.5% glucose at 30° C., LB+Glc 24 h; 24 h growth in LB+0.5% glucose at 30° C. In all the experiments presented in FIG. 5B, the S. typhimurium were pre-grown at 30° C. for 6 h in LB containing 0.5% glucose, then pelleted and resuspended for 2 h under the following conditions: LB; in LB at 30° C., LB+Glc; in LB+0.5% glucose at 30° C., LB pH 5; in LB at pH 5.0 at 30° C., 0.4 M NaCl; in 0.4 M NaCl at 30° C., 0.1M NaCl; in 0.1M NaCl at 30° C., and Heat Shock 43°; in LB+0.5% glucose at 43° C. After these two-hour treatments, cell-free fluids were prepared from each sample and assayed.

FIG. 6. S. typhimurium signaling activity in limiting and non-limiting concentrations of glucose. S. typhimurium LT2 was grown in LB in the presence of limiting (0.1%) and non-limiting (1.0%) concentrations of glucose. The activity present in the cell-free culture fluids (black bars) was assayed at the times indicated and normalized to that produced by 1×10⁹ cells. The increase in signaling activity measured in the 0.4 M NaCl osmotic shock fluids prepared from the same cells is shown as the white bars on top of the black bars. These data are also normalized for 1×10⁹ cells. The signaling activity for limiting glucose is shown in FIGS. 6A, 6C, and 6E, and that for non-limiting glucose is shown in FIGS. 6B, 6D, and 6F. FIGS. 6A and 6B also show the percent glucose remaining (triangles), FIGS. 6C and 6D show the cell number (squares), and Panels E and F show the pH (circles) at each time point.

FIG. 9. The luxS and ygaG genes from *V. harveyi* and *E. coli* MG1655. FIG. 9A shows a restriction map of the *V. harveyi* luxS$_{V.h.}$ chromosomal region which was defined by Tn5 insertion. The sites of Tn5 insertions that disrupted the AI-2 production function and one control Tn5 insertion outside of the luxS$_{V.h.}$ locus are shown (triangles). FIG. 9B depicts the ygaG region in the *E. coli* MG1655 chromosome. This ORF is flanked by the emrB and gshA genes. The direction of transcription of each gene is indicated by the horizontal arrows. The corresponding position of the MudJ insertion that eliminated AI-2 production in *S. typhimurium* LT2 is shown by a vertical arrow. H, R, P, and B denote HindIII, EcoRI, PstI and BamHI restriction sites, respectively.

FIG. 10 shows autoinducer production phenotypes of *V. harveyi* and *S. typhimurium* strains. Cell-free culture fluids from *V. harveyi* and *S. typhimurium* strains were prepared and tested for AI-2 activity in the *V. harveyi* BB170 bioassay. FIG. 10A: AI-2 production phenotypes of the wild type *V. harveyi* strain MM28 which contains a Tn5 insertion outside of luxS$_{V.h.}$ (denoted WT) and the luxS$_{V.h.}$::TnS mutant strain MM30 (denoted luxS⁻). FIG. 10B: A1-2 production phenotypes of wild type *S. typhimurium* LT2 (denoted WT) and the ygaG::MudJ insertion mutant strain CS132 (denoted ygaG⁻). Activity is reported as fold-induction of luminescence expression of the *V. harveyi* BB170 reporter strain over that when sterile medium was added.

FIG. 11 is a graph showing complementation of AI-2 production in *S. typhimurium* CS132 and *E. coli* DH5α. Cell-free culture fluids from *E. coli* and *S. typhimurium* strains were tested for AI-2 activity in the bioassay. The activity present in these fluids was compared to that produced by wild type *V. harveyi* BB120. In the figure, the level of BB120 activity was normalized to 100%. FIG. 11A: AI-2 activity in cell-free fluids from wild type *V. harveyi* BB120, *E. coli* O157:H7, and *S. typhimurium* LT2. FIG. 11B: Complementation of *S. typhimurium* CS132 vgaG::MudJ) and FIG. 11C: Complementation of *E. coli* DH5α. In Panel B and C, the in trans AI-2 production genes are the following: vector control (denoted: none), *E. coli* O157:H7 ygaG; and *V. harveyi* BB120 luxS$_{V.h.}$ *E. coli* and *V. harveyi* are abbreviated $_{E.c.}$ and $_{V.h.}$, respectively.

FIG. 12 shows the alignment of LuxS and YgaG protein sequences. The translated protein sequences for the AI-2 production family of proteins are shown. We determined the sequences for the luxS$_{V.h.}$ gene from *V. harveyi* BB120 (SEQ ID NO:10), and the ygaG genes (re-named herein as luxS$_{E.c.}$ from *E. coli* MG1655 (SEQ ID NO:25), *E. coli* 0157.H7 (SEQ ID NO:11), and *E. coli* DH5α (SEQ ID NO:26). The *S. typhimurium* LT2 ygaG (re-named herein luxS$_{S.t.}$ partial sequence came from the *S. typhimurium* database. Amino acid residues that are not identical to the LuxS$_{V.h.}$ protein are underlined and not in bold font. The site of the frame shift mutation in the *E. coli* DH5α DNA sequence is denoted by an "*." The 20 altered amino acid residues that are translated following the frame shift are enclosed by the box.

FIG. 16 panels A and B show the results of a 6 hour assay using compounds 6, 9, 15 and 18 (panel A) and compounds 3, 4, 7 and 13 (panel B) on test strain BB170. FIG. 16 panels C and D show the effect of the same compounds on control strain JAF78.

FIG. 19 shows a list of compounds and their effect on AI-2 activity in the *V. harveyi* luminescence assay.

As shown in FIG. 23, the entire plate clears due to *S. pyogenes* proteolytic activity except for the zone surrounding the QXP031 containing disc where proteolysis was inhibited.

DETAILED DESCRIPTION OF THE INVENTION

Definitions

Figure 2:
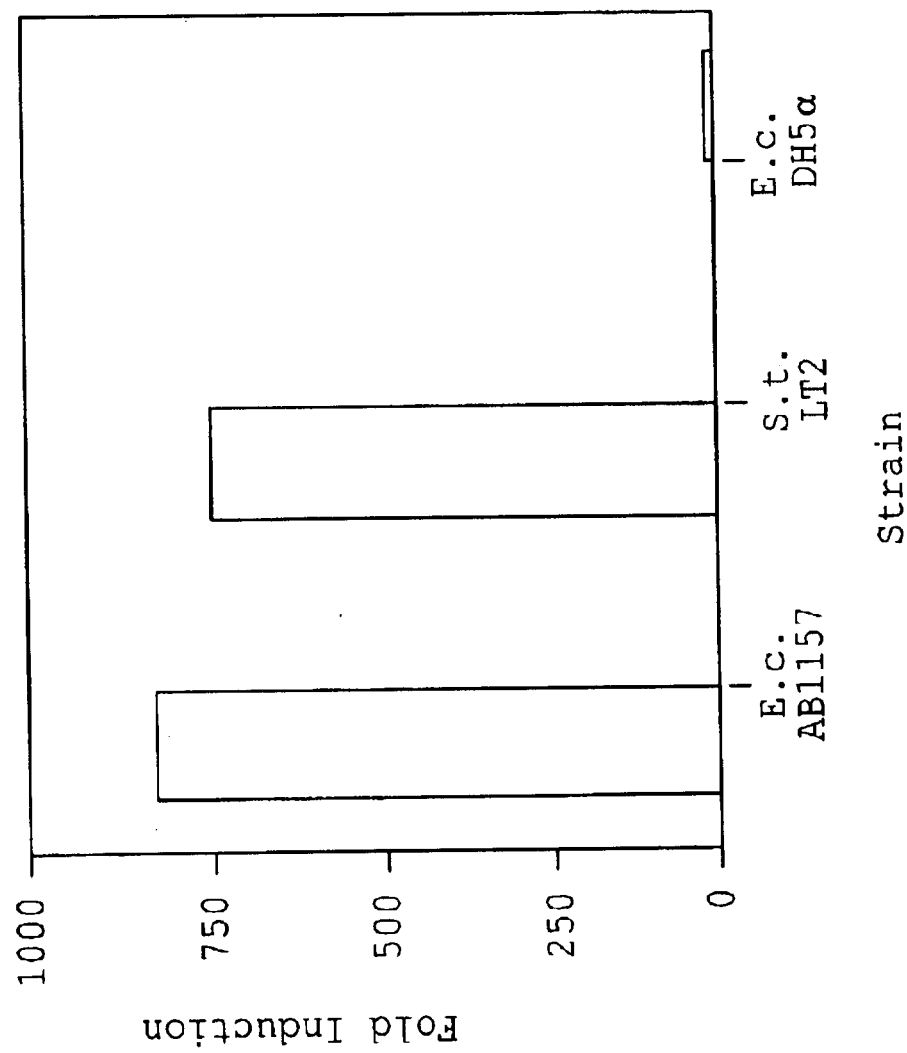
FIG. 2. Secretion of the autoinducer-2 signaling molecule by viable E. coli and S. typhimurium. The response of the V. harveyi reporter strain BB170 (Sensor 1⁻, Sensor 2⁺) to a signaling substance produced and secreted by E. coli AB1157 and S. typhimurium LT2 but not E. coli DH5α is shown. V. harveyi reporter strain BB170 was diluted 1:5000 in AB medium and light output per cell was monitored during growth. At the start of the experiment, either 1×10⁶ E. coli AB1157, S. typhimurium LT2 or E. coli DH5α washed and resuspended viable cells (left-hand, white bars) or UV-killed cells (right-hand, black bars) was added. The data are presented as the fold-activation above the endogenous level of luminescence expressed by V. harveyi BB170 at the 5-hour time point. Abbreviations used for the different strains are: S.t; *Salmonella typhimurium*, and E.c; *Escherichia coli*.

"Lower alkyl" refers to alkyl groups have from one to about ten carbon atoms.

"Isomer" means stereoisomers, and includes enantiomers and diastereomers.

"Purified from a native source" includes autoinducer-2 analogs that have been manufactured by an organism, and includes isolating an autoinducer-2 analog from the culture medium or cytoplasm of bacteria such as *S. typhimurium* through use of conventional purification techniques.

"Inhibiting infectivity" includes methods of affecting the ability of a pathogenic organism to initially infect or further infect a subject that would benefit from such treatment.

"Biomarker" refers to any bacterial cell component that is identifiable by known microscopic, histological, or molecular biological techniques. Such a biomarker can be, for example, a molecule present on a cell surface, a protein, a nucleic acid, a phosphorylation event, or any molecular or morphological characteristic of a bacterial cell that changes when the bacterium is in the presence of an autoinducer.

"probe" can be a nucleic acid, protein, small molecule, or antibody useful for detecting a bacterial biomarker present in a sample.

As used herein, the term "medical device" means a device having surfaces that contact tissue, blood, or other bodily fluids in the course of their operation. This definition includes within its scope, for example, surgical implants, surgical sutures, wound dressings, extracorporeal devices for use in surgery such as blood oxygenators, blood pumps, blood sensors, tubing used to carry blood and the like which contact blood which is then returned to the subject. The definition includes within its scope endoprostheses implanted in blood contact in a human or animal body such as vascular grafts, stents, pacemaker leads, heart valves, and the like that are implanted in blood vessels or in the heart. The definition also includes within its scope devices for temporary intravascular use such as catheters, guide wires, and the like which are placed into the blood vessels or the heart for purposes of monitoring or repair.

A "compound" can be any agent, composition, or molecule that affects the activity of AI-2 or affects the activity of a protein that binds with AI-2. For example, a compound of the invention can be a nucleic acid, a protein, an analog of AI-2 or small molecule. A "compound" includes molecules that regulate the autoinducer-2 receptors, such as LuxP or LuxQ. For example, a compound of Structure I, II, III or IV can regulate the activity of a LuxP protein, a LuxQ protein, a LuxP-LuxQ complex, a LuxP-AI-2 complex, or a LuxP-LuxQ-AI-2 complex, such that bacterial growth or the expression of an extracellular virulence factor is regulated. Such compounds include inhibitors that interact directly with AI-2 such that AI-2 is prevented from acting as a sensor for quorum-sensing Signaling System-2. For example, a compound of the invention could interact directly with 4,5-dihydroxy-2-cyclopenten-1-one or 4-hydroxy-5-methyl-2h-furan-3-one.

AI-2 "inhibitor" refers to molecules that interfere with the ability of the autoinducer to act as a signal for luminescence, bacterial growth or pathogenesis, and includes molecules that degrade or bind to AI-2. Inhibitors also include those compounds that regulate AI-2 activity by interacting with those proteins normally associated with bacterial growth.

The "activity" of AI-2 encompasses any aspect of AI-2's ability to act as a signaling factor in bacterial quorum sensing, growth regulation, and pathogenesis.

"Autoinducer-2 analog" means any compound with at least 10% of the autoinducer-2 activity of any stereoisomer of 4-hydroxy-5-methyl-2H-furan-3-one, and includes the naturally-occurring autoinducer-2.

"Signaling factor," "signaling molecule," "autoinducer," and more specifically, "autoinducer-2," or "AI-2" all refer to the novel signaling factor of the present invention. The terms "autoinducer-2" and "AI-2" refer specifically to the signaling factor involved in quorum sensing system 2. The terms "signaling factor" or "signaling molecule," "autoinducer" or "AI-2-like molecule" refer generally to the signaling factors of the present invention, of which AI-2 is an example.

"Isolated nucleic acid", when applied to DNA, refers to a DNA molecule that is separated from sequences with which it is immediately contiguous (in the 5' and 3' directions) in the naturally occurring genome of the organism from which it was derived. For example, the "isolated nucleic acid" may comprise a DNA molecule inserted into a vector, such as a plasmid or virus vector, or integrated into the genomic DNA of a procaryote or eucaryote. An "isolated nucleic acid molecule" may also comprise a cDNA molecule.

"Isolated nucleic acid" primarily refers to an RNA molecule encoded by an isolated DNA molecule as defined above. Alternatively, the term may refer to an RNA molecule that has been sufficiently separated from RNA molecules with which it would be associated in its natural state (i.e., in cells or tissues), such that it exists in a "substantially pure" form (term "substantially pure" is defined below).

"Isolated protein" or "isolated and purified protein" refers primarily to a protein produce by expression of an isolated nucleic acid molecule of the invention. Alternatively, this term may refer to a protein that has been sufficiently separated from other proteins with which it would naturally be associated, to exist in "substantially pure" form.

"Substantially pure" refers to a preparation comprising at least 50–60% by weight the factor of interest (e.g., pathogenesis signaling factor, nucleic acid, oligonucleotide, or protein). More preferably, the preparation comprises at least 75% by weight, and most preferably 90–99% by weight, the factor of interest. Purity is measured by methods appropriate for the factor of interest (e.g., chromatographic methods, agarose or polyacrylimide gel electrophoresis, HPLC analysis, and the like).

"Immunologically specific" refers to antibodies that bind to one or more epitopes of a protein of interest, but that do not substantially recognize and bind other molecules in a sample containing a mixed population of antigenic biological molecules.

"Specifically hybridizing" refers to the association between two single-stranded nucleotide molecules of sufficiently complementary sequence to permit such hybridization under pre-determined conditions generally used in the art (sometimes termed "substantially complementary"). In particular, the term refers to hybridization of an oligonucleotide with a substantially complementary sequence contained within a single-stranded DNA or RNA molecule of the invention, to the substantial exclusion of hybridization of the oligonucleotide with single-stranded nucleic acids of non-complementary sequence.

"Promoter region" refers to the transcriptional regulatory regions of a gene, which may be found at the 5' or 3' side of the coding region, or within the coding region, or within introns.

"Selectable marker gene" refers to a gene encoding a product that, when expressed, confers a selectable phenotype such as antibiotic resistance on a transformed cell.

"Reporter gene" refers to a gene that encodes a product that is easily detectable by standard methods, either directly or indirectly.

"Operably linked" means that the regulatory sequences necessary for expression of the coding sequence are placed in the DNA molecule in the appropriate positions relative to the coding sequence to enable expression of the coding sequence. This same definition is sometimes applied to the arrangement of transcription units and other regulatory elements (e.g., enhancers or translation regulatory sequences) in an expression vector.

"Autoinducer-associated bacterial biomarker" refers to any bacterial cell component that an autoinducer regulates, modifies, enhances, inhibits, or induces.

The term "regulate" has its usual meaning, but also encompasses the meanings of the words enhance, inhibit, and mimic. In addition, as used herein, the term "expression" when used in connection with a gene such as LuxP, LuxQ or a gene encoding a virulence factor, has its usual meaning, but also encompasses the transcription of the gene, the longevity of functional mRNA transcribed from the gene, the translation of that mRNA, and the activity of the gene product. "Regulating" encompasses inhibition or activation of the autoinducer-2 signaling pathway.

"Antibody" includes intact molecules of polyclonal or monoclonal antibodies, as well as fragments thereof, such as Fab and F(ab')2. For example, monoclonal antibodies are made from antigen containing fragments of a protein by methods well known to those skilled in the art (Kohler et al., Nature, 256:495, 1975).

"Substantially the same" refers to, nucleic acid or amino acid sequences having sequence variation that do not materially affect the nature of the protein (i.e., the structural characteristics and/or biological activity of the protein). With particular reference to nucleic acid sequences, the term "substantially the same" refers to the coding region and to conserved sequences governing expression, and refers primarily to degenerate codons encoding the same amino acid, or alternate codons encoding conservative substitute amino acids in the encoded polypeptide. With reference to amino acid sequences, the term "substantially the same" refers generally to conservative substitutions and/or variations in regions of the polypeptide not involved in determination of structure or function. The terms "percent identity" and "percent similarity" are also used herein in comparisons among amino acid sequences. These terms are defined as in the UWGCG sequence analysis program (Devereaux et al., Nucl. Acids Res. 12: 387–397, 1984), available from the University of Wisconsin, and the parameters used by that program are the parameters to be used herein to compare sequence identity and similarity.

"Antibiotic" includes bactericidal, as well as bacteristatic agents, and includes sulfonamides, anti-urinary tract agents, β-lactam antibiotics, cephalosporins, clavulanic acid derivatives, aminoglycosides, tetracylines and related antibacterial agents, macrolides, anti-tuberculosis drugs, anti-Mycobacterium avium agents, anti-leprosy agents, antifungal agents and antiviral agents.

"Sulfonamides" includes sulfanilamide, sulfamethoxazole, sulfacetamide, sulfadiazine, sulfisoxazole, para-aminobenzoic acid and the like, as well as trimethoprim-sulfamethoxazole.

"Quinolones" means nalidixic acid, cinoxacin, norfloxacin, ciprofloxacin, ofloxacin, sparfloxacin, lomefloxacin, fleroxacin, pefloxacin, amifloxacin and the like.

"Anti-urinary tract infectives" means methenamine, nitrofurantoin and the like.

By "β-lactam antibiotics" we mean penicillins, cephalosporins and the like. By penicillins, examples are penicillin G, penicillin V, methicillin, oxacillin, cloxacillin, dicloxacillin, nafcillin, ampicillin, amoxicillin, carbenicillin, carbenicillin indanyl, ticarcillin, mezlocillin, piperacillin, bacampicillin and the like.

"Cephalosporins" means compounds such as cephalothin, cefazolin, cephalexin, cefadroxil, cefamandole, cefoxitin, cefaclor, cefuroxime, cefuroxime axetil, loracarbef, cefonicid, cefotetan, ceforanide, cefotaxime, cefpodoxime proxetil, ceftizoxime, ceftriaxone, cefoperazone, ceftazidime, cefepime, moxalactam and the like. By carbapenems we mean beta-lactam antibiotics such as imipenem, meropenem, aztreonam (imipenem-cilastatin).

"Clavulanic acid derivatives" means combinations of amoxicillin and clavulanic acid and ticarcillin and clavulanic acid.

"Aminoglycosides" means streptomycin, gentamicin, tobramycin, amikacin, netilmicin, kanamycin, neomycin and the like.

"Tetracylines" means chlortetracycline, oxytetracycline, demeclocycline, methacycline, doxycycline, minocycline and the like.

"Related antibacterial agents" means chloramphenicol, clindamycin, spectinomycin, polymyxin B, colistin, vancomycin, bacitracin, RP 59500, glycylcyclines and the like.

"Macrolides" means erythromycin, clarithromycin, azithromycin and the like.

"Anti-tuberculosis drugs" means isoniazid, rifampin, ethambutol, streptomycin, pyrazinamide, ethionamide, aminosalicylic acid, cycloserine, capreomycin and the like.

By drugs for the "anti-Mycobacterium avium agents" we mean rifabutin, macrolides, quinolones, clofazimine, amikacin and the like.

"Anti-leprosy agents" means sulfones such as dapsone and sulfoxone sodium, rifampin, clofazimine, thalidomide and ethionamide.

"Antifungal agents" means systemic antifungal agents such as amphotericin B, flucytosine, imidazoles and triazoles, ketoconazole, miconazole, itraconzole, fluconazole and the like. This category also includes griseoftilvin. We also mean topical antifungal agents such as clotrimazole, econazole, miconazole, terconazole, butoconazole, ciclopirox olamine, haloprogin, tolnaftate, naftifine, terbinafine as well as nystatin, amphotericin B, undecylenic acid, benzoic acid, salicyclic acid, propionic acid, caprylic acid and potassium iodide.

"Antiviral agents" means anti-herpes virus agents such as acyclovir, famciclovir, foscarnet, ganciclovir, idoxuridine, sorivudine, trifluridine, valacyclovir, vidarabine, penciclovir as well as newer agents such as anti HIV-1 such as lamivudine, FTC, adefovir (PMEA), nevirapine, delavirdine, loviride, saquinavir, indinavir, and the like; anti-hepatitis B virus agents such as lamivudine, famciclovir and fialuridine; anti-herpes viruses such as cidofovir (HPMPC) and lobucavir, anti papillomavirus agents such as afovirsen; anti rhinovirus agents such as sICAM-1, pirodavir, and the like; anti-influenza virus drugs such as GG167; anti-retroviral agents such as didanosine, stavudine, zalcitabine, zidovudine and the like as well as other antiviral agents such amantadine, interferon alpha, ribavirin and rimantadine.

In accordance with the present invention, the applicants have identified an analog of an extracellular signaling factor produced by several strains of pathogenic bacteria, including *Salmonella typhimurium* and *Escherichia coli*, that affects the pathogenesis or virulence of these bacteria They have also identified and cloned genes involved in the biosynthesis of the naturally-occurring signaling factor. The identification of an autoinducer-2 analog and the cloning the genes that encode proteins involved in biosynthesis of the naturally-occurring autoinducer-2 open a new avenue for drug design aimed at affecting quorum sensing in bacteria. Drugs designed to interfere with quorum sensing constitute a new class of antibiotics. The invention further provides methods for detecting an autoinducer and methods for producing in vitro compounds with autoinducer-2 activity.

Preparation of the Factor with AI-2 Signaling Activity

Initial strategies for purifying the signaling molecule of the invention resulted in a partially purified preparation comprising the molecule with a specific signaling activity estimated at about 0.1–1.0 mg of the partially purified material stimulating a 1,000-fold increase in luminescence, as measured in the *V. harveyi* bioassay. The signaling activity does not extract quantitatively into organic solvents and it does not bind to either a cation or an anion exchange column. The molecule is a small (less than 1,000 kDa), polar but uncharged organic factor. The activity is acid stable and base labile, and it is heat resistant to 80° C. but not 100° C. These features of the signaling molecule make it clear that the molecule is different from any previously described autoinducer.

The signaling factor of the present invention may be purified from its natural sources, i.e., the bacteria that produce it. Alterations in the culture medium, e.g., by addition of glucose or another sugar, an increase in the osmolarity, and/or decreases in pH, can increase production of the signaling molecule in Salmonella and other enteric bacteria and have enabled purification of the signaling molecule to near-homogeneity. Thus, the molecule has now been highly purified from culture fluids of enteric bacteria (e.g., *E. coli, S. typhimurium*) through use of the following protocol:

Grow a culture of the signal producing enteric bacterium overnight in LB containing 0.5% glucose or another sugar (37° C., with aeration). Inoculate fresh LB containing glucose or another sugar at 0.5% with the overnight culture, at a 1:100 dilution. Grow the diluted culture to mid-exponential phase (3.5 h, 37° C., with aeration).

Pellet the cells (10,000 rpm, 10 min, 4° C.). Discard the culture medium. Resuspend the cells and wash in 1/10th the original volume of low osmolarity NaCl solution (0.1M NaCl in water).

Pellet the cells again (10,000 rpm, 10 min, 4° C.). Discard the low osmolarity culture fluid. Resuspend the cells in 1/10th the original volume of high osmolarity NaCl solution (0.4 M NaCl in water). Incubate the suspension at 37° C. for 2 h with aeration. During this time, increased production and secretion of the signaling molecule occurs.

Pellet the cells (10,000 rpm, 10 min, 4° C.). Collect the supernatant containing the secreted signaling molecule, and filter the supernatant through a 0.2 M bacterial filter to remove any remaining cells.

Evaporate the aqueous filtrate using a rotary evaporator at 30° C. Extract the dried filtrate in 1/10th the original volume of chloroform:methanol (70:30).

Evaporate the organic extract using a rotary evaporator at room temperature. Re-dissolve the dried extract in methanol at 1/100th of the original volume.

Subject the partially purified signal to high performance liquid chromatography (HPLC), using a preparative reverse phase C18 column. Elute the molecule with a linear gradient of 0–100% acetonitrile in water at 5 mL per minute. Collect 30 fractions, 5 mL each.

Assay the HPLC fractions in the *V. harveyi* BB170 AI-2 assay, and pool the active fractions.

The product from the $C_{18}$ column contains the signaling molecule and a small number of other organic molecules. This purified preparation of the signaling molecule has activity 50–100 times greater than that of the partially purified material described above (the preparation of which did not include the high osmoticum step or the final HPLC step), i.e., 1–10 μg material stimulates a 1,000-fold increase in luminescence in the *V. harveyi* bioassay.

Subsequent strategies for purifying the AI-2 analog have led to the identification of a novel in vitro system for producing AI-2. Thus, in addition to providing a cloned, overexpressed and purified *S. typhimurium* LuxS protein, the present invention also provides a method for producing AI-2 in vitro. The present invention provides a mechanism for generating large quantities of pure AI-2 useful for mass spectral and NMR analysis, and for screening compounds that regulate the activity of AI-2. Moreover, the present invention provides a method for determining the in vivo biosynthetic pathway for AI-2 synthesis. The in vitro method for AI-2 analog production is described below in Example 5 and FIG. 15. The method provides a novel means for efficiently producing autoinducer molecules for further study. The method also provides a means for producing substantial quantities of AI-2 analogs for use in commercial applications. Such applications include, but are not limited to, adding AI-2 analogs to a growth medium to increase bacterial growth. Such a method is particularly useful in the in the production of antibiotics from cultured bacteria. Preferably, the AI-2 analog is produced by the in vitro method set forth in Example 5 of the disclosure.

Uses of AI-2 Analogs

The autoinducer-2 analogs described here are useful for influencing quorum sensing in bacteria. Such analogs may be identified by large-scale screening of a variety of test compounds through use of the *V. harveyi* bioassay. Reduction in signaling activity in the presence of a test compound indicates the ability of that compound to, for example, block bacterial pathogenesis by affecting the expression of one or more virulence factors.

For example, naturally produced compounds can be screened for their effect on the interaction between autoinducer-2 and receptors for it, such as LuxP and LuxP-LuxQ.

Now that components of the quorum sensing pathway have been identified in *E. coli*, inhibition of one or more of those components can be used to screen potential signaling molecule inhibitors or analogs. The inventors have prepared a ler-lacZ reporter fusion construct to be used in testing for reduction of expression of the Type III secretion gene in *E. coli* O157:H7 (pathogenic strain) directly. Furthermore, a similar locus exists in *S. typhimurium*.

Thus, the invention provides a method for selecting autoinducer-2 analogs such as 4-hydroxy-5-methyl-2h-furan-3-one by measuring the activity of a selected gene by the naturally-occurring autoinducer-2 in the presence and absence of a suspected inhibitor or synergist. In this manner, compounds that regulate bacterial pathogenesis can be rapidly screened.

Compounds identified in the method of the invention can be further evaluated, detected, cloned, sequenced, and the like, either in solution or after binding to a solid support, by any method usually applied to the detection of a specific DNA sequence such as PCR, oligomer restriction (Saiki et al., Bio/Technology, 3:1008–1012, 1985), allele-specific oligonucleotide (ASO) probe analysis (Conner et al., Proc. Natl. Acad. Sci. USA, 80:278, 1983), oligonucleotide ligation assays (OLAs) (Landegren et al., Science, 241:1077, 1988), and the like. Molecular techniques for DNA analysis have been reviewed (Landegren et al., Science, 242:229–237, 1988). Also included in the screening method of the invention are combinatorial chemistry methods for identifying chemical compounds that bind to LuxP or LuxQ. See, for example, Plunkett and Ellman, "Combinatorial Chemistry and New Drugs," Scientific American, April, p.69 (1997).

Naturally-occurring autoinducer-2 can be purified from the native source using conventional purification techniques, derived synthetically by chemical means, or preferably, produced by the in vitro method of the invention described below.

One of the instant methods entails regulating the activity of an autoinducer-2 receptor comprising contacting an autoinducer-2 receptor with an AM-2 agonist or antagonist. A further embodiment of this method employs a compound of Formulas I, II, III, or IV of any combination thereof. A further embodiment of either of these embodiments entails when the autoinduced-2 receptor is selected from the group consisting of Lux P and Lux Q. Further embodiments of any of the foregoing embodiments occur when the AI-2 receptor is found on a bacterial cell, and in turn when the bacterial cell is found in a warm-blooded host.

The activity regulated in any of the foregoing embodiments can be, for example, bacterial cell growth, bacterial virulence, siderophore expression, exopolysaccharide production in bacterial cells, bacteria colony morphology (including smooth colony morphology, such as that exhibited by a pathogenic bacterial cell), biofilm formation, and the like. These embodiments can be practiced with compounds from Formulas I, II, III, and IV, or any combination thereof, and especially so with 4-hydroxy-5-methyl-3(2H) furanone. One embodiment of any of the foregoing embodiments can be practiced wherein AI-2 receptor is part of a bacterial cell selected from the group consisting of *Vibrio harveyi, Vibrio cholerae, Vibrio parahaemolyticus, Vibrio alginolyticus, Pseudomonas phosphoreum, Yersinia enterocolitica, Escherichia coli, Salmonella typhimurium, Haemophilus influenzae, Helicobacter pylori, Bacillus subtilis, Borrelia burgdorferi, Neisseria meningitidis, Neisseria gonorrhoeae, Yersinia pestis, Campylobacter jejuni, Deinococcus radiodurans, Mycobacterium tuberculosis, Enterococcus faecalis, Streptococcus pneumoniae, Streptococcus pyogenes* and *Staphylococcus aureus*.

The invention further provides methods of inhibiting the infectivity of a pathogenic organism as well as therapeutic compositions containing an AI-2 analog or AI-2 inhibitor of the invention. The methods comprise administering to a subject a therapeutically effective amount of a pharmaceutical composition that inhibits the activity of naturally-occurring AI-2.

A pharmaceutical composition of the invention can include a compound as set forth in Structure I, II, III or IV. A composition including such a compound can, for example, prevent the transcriptional activation of extracellular virulence factors such as accessory cholera enterotoxin, adenylate cyclase toxin, adhesin, aerolysin toxin, aggregation substance, i.e., asa373, Agr A,B,C,D, SigB etc., alkaline protease, alpha toxin, alpha-haemolysin, alveolysin, anthrax toxin, APX toxin, beta toxin, botulinum toxin, bundle forming pilus structural subunit, C2 toxin, C3 toxin, C5A peptidase, cardiotoxin, chemotaxis, cholera toxin, ciliotoxin, clostridial cytotoxin, clostridial neutotoxin, collagen adhesion gene, crystal endotoxin, cyaA toxin, cytolysin, delta toxin, delta toxin, delta-lysin, diphtheria toxin, emetic toxin, endotoxin, staphylococcal enterotoxins A, B, C1, C2, C3, D, E, G , enterotoxin, exfoliative toxin, exotoxin, exotoxin A, exotoxin B, exotoxin C, extracellular elastase, fibrinogen, fibronectin binding protein, i.e., fnbA, filamentous hemagglutinin, fimbriae, gamma hemolysin, gelatinase, i.e., gelE, haemolysin, hemolysin B, hemagglutinin, histolyticolysin, IGG binding protein A, i.e., spaI, intimin, invasin, iron siderophores, ivanolysin, ivanolysin O, lantibiotic modifying enzyme, lantibiotic structural protein, lecithinase, ler (positive regulator of LEE genes), leukotoxin, lipoprotein signal peptidase, listeriolysin O, M protein, motility, neurotoxin, nonfimbrial adhesins, oedema factor, perfringolysin O, pennease, pertussis toxin, phospholipase, pili, plasmid encoded regulator per, pneumolysin, poly-D-glutamic acid capsule, pore-forming toxin, proline permease, RNAIII, RTX toxin, serine protease, shiga toxin, siderophoretiron acquisition protein, SigA proteases, Spe A, Spe B, Spe C, Sta toxin, Stb toxin, streptolysin O, streptolysin S, superantigen, superoxide dismutase, TCP, tetanus toxin, thiol-activated cytolysin, tracheal cytotoxin, TSST toxin (TSST-1), urease and zona occludens toxin.

The invention provides autoinducer-2 analogs that influence bacterial cell growth or the expression of a bacterial virulence factor by regulating the activity of pathways activated by naturally-occurring autoinducer-2. Such pathways include, for example, the production of siderophores and the regulation of bacterial colony morphology. An autoinducer-2 analog of the present invention can be used to increase bacterial growth by acting in concert with, or as a replacement for, AI-2. Alternatively, an autoinducer-2 analog can inhibit AI-2 by competing with naturally-occurring AI-2 for binding to autoinducer-2 receptors including LuxP or LuxQ.

In addition, autoinducer-2 receptors such as LuxP or LuxQ provide a common target for the development of a vaccine. Antibodies raised to autoinducer-2 receptors, such as LuxP or LuxQ, for example, can inhibit the activation of bacterial pathways associated with virulence. Autoinducer-2 receptors provide common antigenic determinants that can be used to immunize a subject against multiple pathogen-associated disease states. Challenging a subject with a polypeptide derived from an autoinducer-2 receptor, or an antigenic fragment thereof, isolated from a particular organism may confer protective immunity to other disease states associated with a different organism. For example, a vaccine developed to the LuxP protein isolated from *V. cholerae* may be capable of cross-reacting with a LuxP homologue expressed by a different organism. Thus methods of the present invention can be used to treat pathogen-associated disease states.

The invention further provides a method for promoting production of a bacterial product, such as an antibiotic or virulence factor, by adding an autoinducer-2 analog to a culture of bacteria at a concentration effective to promote cellular metabolism, growth or recovery. For example, antibiotic-producing bacteria typically only produce an antibiotic near the peak of log phase growth. Addition of autoinducer-2 analogs to a culture of such bacteria provides a method for inducing antibiotic production at an earlier phase of growth, and/or for increasing the amount of antibiotic produced.

The invention further provides a method for identifying factors that degrade or inhibit synthesis autoinducer-2. The concentration of naturally-occurring autoinducer-2 reaches a maximum in early log phase of bacterial cell growth and subsequently decreases in late log phase and stationary phase. These data indicate that a mechanism exists for the degradation of autoinducer-2 at a specific point in bacterial growth. The invention enables identification of the mechanism that controls levels of naturally-occurring autoinducer-2. For example, partially purified bacterial extracts can be assayed against isolated autoinducer-2 to identify those fractions that degrade autoinducer-2.

Autoinducer-2 analogs can also be used in screens for other targets that they regulate. Cloned promoter-fusion libraries can be prepared from any species of bacteria and these libraries can be used to identify genes that are affected by the signaling factor, simply by screening for differences in reporter activity in the presence and absence of an autoinducer-2 analog.

Description of Nucleic Acids Encoding Proteins Involved in Signaling Factor Biosynthesis The applicants have cloned and characterized the genes that encode a novel family of proteins responsible for autoinducer production in *V. harveyi, S. typhimurium* and *E. coli*. Members of this family of autoinducer production genes are designated as luxS, specifically luxS$_{V.h.}$, luxS$_{S.t.}$, and luxS$_{E.c.}$, for *E. coli, V. harveyi, S. typhimurium* and *E. coli.*, respectively, and their sequences appear as SEQ ID NO:1, SEQ ID NO:2 and SEQ ID NOS:3 and 4, respectively (the sequences read in the 5' to 3' direction). Corresponding amino acid sequences appear as SEQ ID NO:10, SEQ ID NO:11 and SEQ ID NO:12, respectively (and in FIG. 12). It is believed that SEQ ID NOS:1 and 2 constitute full-length clones, whereas SEQ ID NO:3 and SEQ ID NO:4 do not.

This invention encompasses luxS genes and their encoded enzymes from any bacterial species, having the sequence, structural and functional properties of the luxS-encoded proteins described herein. As mentioned in Example 3, homologous nucleic acid sequences have been identified in a variety of bacterial species, but their identity as luxS genes heretofore had not been appreciated. luxS nucleotide and deduced amino acid sequences from other bacterial species appear as SEQ ID NOS:5–9 and 13–17, respectively, and include sequences from *Haemophilus influenzae, Helicobacter pylon, Bacillus subtilis, Borrelia burgdorferi* and *Vibrio cholerae*.

Variants and natural mutants of SEQ ID NOS:1–9 are likely to exist within different species or strains of Vibrio, Escherichia and Salmonella (indeed, *E. coli* strain DH5α possesses a non-functional mutant form of the gene). Because such variants are expected to differ in nucleotide and amino acid sequence, this invention provides an isolated luxS nucleic acid and encoded protein having at least about 50–60% (preferably 60–80%, most preferably over 80%) sequence homology in the coding region with the nucleotide sequences set forth as SEQ ID NOS:1–9, respectively (and, preferably, specifically comprising the coding regions of SEQ ID NOS:1–9), and the amino acid sequence of SEQ ID NOS:10–17. Because of the natural sequence variation likely to exist among these proteins and nucleic acids encoding them, one skilled in the art would expect to find up to about 4050% sequence variation, while still maintaining the unique properties of the LuxS-encoded proteins of the present invention. Such an expectation is due in part to the degeneracy of the genetic code, as well as to the known evolutionary success of conservative amino acid sequence variations, which do not appreciably alter the nature of the protein. Accordingly, such variants are considered substantially the same as one another and are included within the scope of the present invention.

The luxS genes identified here bear no homology to other genes known to be involved in production of acyl-homoserine lactone autoinducers (luxI-like (Fuqua et al., J.

Bacteriol. 176, 269–275, 1994), luxLM-ainS-like (Bassler et al., 1993, supra; Gilson et al., J. Bacteriol. 177, 6946–6951, 1995). Database analysis of bacterial genomes reveals that many other species of bacteria possess a gene homologous to luxS from *V. harveyi, S. typhimurium* and *E. coli*, as shown in Table 1.

TABLE 1

| Bacterium | Percent homology to LuxS of V. harveyi | Percent identity to LuxS of V. harveyi |
|---|---|---|
| Haemophilus influenza | 88 | 72 |
| Helicobacter pylori | 62 | 40 |
| Bacillus subtilis | 58 | 38 |
| Borrelia burgfdorferi | 52 | 32 |
| Neisseria meningitidis | 89 | 80 |
| Neisseria gonorrhoeae | 89 | 80 |
| Yersinia pestis | 85 | 77 |
| Campylobacter jejuni | 85 | 74 |
| Vibrio cholerae | 95 | 90 |
| Deinococcus radiodurans | 65 | 45 |
| Mycobacterium tuberculosis | 59 | 41 |
| Enterococcus faecalis | 60 | 44 |
| Streptococcus pneumoniae | 57 | 36 |
| Streptococcus pyogenes | 57 | 36. |

Mutagenesis of luxS in *V. harveyi, S. typhimurium* and *E. coli* eliminates production of the signaling molecule in all three species of bacteria. *S. typhimurium* could be complemented to full production of the molecule by the introduction of either the *E. coli* O157:H7 $luxS_{E.c.}$ gene or the *V. harveyi* BB120 $luxS_{V.h.}$ gene. These results indicate that both the *E. coli* and *V. harveyi* LuxS proteins can function with *S. typhimurium* cellular components to produce the signaling molecule. Introduction of either the *E. coli* O157:H7 $luxS_{E.c.}$ or the *V. harveyi* BB120 $luxS_{V.h.}$ gene partially complemented *E. coli* DH5α to produce naturally-occurring autoinducer-2.

Pathogenicity is connected with quorum sensing. Pathogenic and non-pathogenic strains differ in their production of naturally-occurring autoinducer-2. For example, *E. coli* O157:H7 strains produce naturally-occurring autoinducer-2 with or without glucose while *E. coli* K-12 strains do not produce it in the absence of a preferred carbon source. Furthermore, all of the *E. coli* O157 strains tested produce greater signaling activity than do non-pathogenic *E. coli* strains. Similarly, pathogenic *S. typhimurium* 14028 produces significantly more signaling activity than does *S. typhimurium* LT2.

Preparation of LuxS Nucleic Acids, Encoded Proteins, and Immunologically Specific Antibodies Nucleic Acids. Nucleotide sequence information, such as the DNAs having SEQ ID NOS:1–9, enables preparation of an isolated nucleic acid molecule of the invention by oligonucleotide synthesis. Synthetic oligonucleotides may be prepared by the phosphoramadite method employed in the Applied Biosystems 38A DNA Synthesizer or similar devices. The resultant construct may be purified according to methods known in the art, such as high performance liquid chromatography (HPLC). Long, double-stranded polynucleotides, such as a DNA molecule of the present invention, must be synthesized in stages, due to the size limitations inherent in current oligonucleotide synthetic methods. Such long double-stranded molecules may be synthesized as several smaller segments of appropriate complementarity. Complementary segments thus produced may be annealed such that each segment possesses appropriate cohesive termini for attachment of an adjacent segment. Adjacent segments may be ligated by annealing cohesive termini in the presence of DNA ligase to construct an entire 1.8 kb double-stranded molecule. A synthetic DNA molecule so constructed may then be cloned and amplified in an appropriate vector.

LuxS nucleic acids also may be isolated from appropriate biological sources through use of known methods. In a preferred embodiment, a genomic clone is isolated from a cosmid expression library of an *S. typhimurium* or *E. coli* genome, or a genomic clone is isolated from a cosmid library of another bacterial genome.

Nucleic acids having the appropriate level sequence homology with the protein coding region of any of SEQ ID NOS:1–9 may be identified by use of hybridization and washing conditions of appropriate stringency. For example, hybridizations may be performed, according to the method of Sambrook et al., through use of hybridization solution comprising: 5×SSC, 5×Denhardt's reagent, 1.0% SDS, 100 g/ml denatured, fragmented salmon sperm DNA, 0.05% sodium pyrophosphate and up to 50% formamide. After hybridization at 37–42° C. for at least six hours, filters are washed as follows: (1) five minutes at room temperature in 2×SSC and 1% SDS; (2) fifteen minutes at room temperature in 2×SSC and 0.1% SDS; (3) thirty minutes to one hour at 37° C. in 1×SSC and 1% SDS; (4) 2 hours at 42–65° C. in 1×SSC and 1% SDS, changing the solution every 30 minutes.

LuxS nucleic acids can also be found through a search of publicly available databases for the luxS sequence in the bacterial genome of interest, design of PCR primers from the sequence, amplification of the gene directly from the chromosome, and cloning of the PCR product. Alternatively, if the complete sequence of a specific bacterial genome is not available, the sequences set forth in the present invention, or any other luxS sequence, may be used to design degenerate oligonucleotides for PCR amplification and cloning of luxS from the chromosome.

Nucleic acids of the present invention may be maintained as DNA in any convenient cloning vector. In a preferred embodiment, clones are maintained in plasmid cloning/ expression vector, such as pBluescript (Stratagene, La Jolla, Calif.), which is propagated in a suitable *E. coli* host cell.

LuxS nucleic acids of the invention include DNA, RNA, and fragments thereof, which may be single or double-stranded. Thus, this invention provides oligonucleotides (sense or antisense strands of DNA or RNA) having sequences capable of hybridizing with at least one sequence of a nucleic acid molecule of the present invention, such as selected segments of the DNA having SEQ ED NOS:1, 2 or 3. Such oligonucleotides are useful as probes for detecting luxS genes or transcripts.

Proteins and Antibodies. A full-length luxS gene product of the present invention may be prepared in a variety of ways, according to known methods. The protein may be purified from appropriate sources, e.g., cultured bacteria such as *S. typhimurium, E. coli* or *V. harveyi*.

The availability of full-length luxS nucleic acids enables production of the encoded protein through use of in vitro expression methods known in the art. According to a preferred embodiment, the enzyme may be produced by expression in a suitable expression system. For example, part or all of a DNA molecule, such as the DNA having SEQ ID NO:1 or 2, may be inserted into a plasmid vector adapted for expression in a bacterial cell, such as *E. coli*, or a eucaryotic cell, such as *Saccharomyces cerevisiae* or other yeast. Such vectors comprise the regulatory elements necessary for expression of the DNA in the host cell, positioned in such a manner as to permit expression of the DNA in the host cell. Such regulatory elements required for expression include promoter sequences, transcription initiation sequences and, optionally, enhancer sequences.

The protein produced by luxS gene expression in a recombinant procaryotic or eucyarotic system may be purified according to methods known in the art. In a preferred embodiment, a commercially available expression/secretion system can be used, whereby the recombinant protein is expressed and thereafter secreted from the host cell, to be easily purified from the surrounding medium. If expression/secretion vectors are not used, an alternative approach involves purifying the recombinant protein by affinity separation, such as by immunological interaction with antibodies that bind specifically to the recombinant protein. Such methods are commonly used by skilled practitioners.

The protein encoded by the luxS gene of the invention, prepared by one of the aforementioned methods, may be analyzed according to standard procedures. For example, the protein may be subjected to amino acid sequence analysis, according to known methods. The stability and biological activity of the enzyme may be determined according to standard methods, such as by the ability of the protein to catalyze production of the signaling molecule under different conditions.

The present invention also provides antibodies capable of immunospecifically binding to the luxS-encoded protein of the invention.

Uses of LuxS Nucleic Acids, Encoded Protein and Immunologically Specific Antibodies LuxS nucleic acids or fragments thereof may be used as probes for luxS genes in (1) in situ hybridization; (2) Southern hybridization (3) northern hybridization; and (4) assorted amplification reactions such as polymerase chain reactions (PCR). They may also be used as probes to identify related genes from other bacteria.

LuxS nucleic acids may further be used to produce large quantities of substantially pure encoded protein, or selected portions thereof. Furthermore, the cloned genes inserted into expression vectors can be used to make large quantities of the signaling molecule itself, from any selected bacterial species, in a recombinant host such as *E. coli* DH5α. Cloning of specific luxS genes, and production of a large quantity of the encoded protein, thereby allows production of a large quantity of the specific autoinducer. This capability will be particularly useful in determining differences, if any, in the structures of autoinducers from different species. Alternatively, large quantities of signaling molecule from the species of interest could be made through use of the cloned gene in an expression vector, and thereafter used in library screens for potential targets in Petri plate assays.

Purified luxS gene products, or fragments thereof, may be used to produce antibodies that also may serve as sensitive detection reagents for those proteins in cultured cells. Recombinant techniques enable expression of fusion proteins containing part or all of a selected luxS-encoded protein. The full length protein or fragments of the protein may be used to advantage to generate an array of antibodies specific for various epitopes of the protein, thereby providing even greater sensitivity for detection of the protein. Other uses of the LuxS proteins include overproduction to make a quantity sufficient for crystallization. Knowledge of the crystal structure of the LuxS proteins would enable determination of the LuxS active site that produces the naturally-occurring autoinducer-2, and that could therefore be used for computer-aided design of autoinducer-2 analogs, LuxS inhibitors, and rational drug design.

Antibodies specific for a LuxS-encoded protein may be used in a variety of assays designed to detect and quantitate the protein. Such assays include, but are not limited to: (1) flow cytometric analysis; (2) immunochemical localization of a LuxS protein in cells or tissues; and (3) immunoblot analysis (e.g., dot blot, Western blot) of extracts from various cells and tissues. Additionally, as described above, antibodies can be used for purification of the proteins (e.g., affinity column purification, immunoprecipitation).

*Vibrio Harveyi* Screening Strain

The invention provides a luxN– and luxS– strain of *V. harveyi*, designated MM32, for identifying inhibitors of the quorum-sensing pathway. Since the new strain is luxN– (i.e., sensor 1–), AI-1 does not affect its ability to grow or to luminesce. Further, since MM32 cannot produce AI-2, addition of exogenous AI-2 or its analogs allows rapid identification of inhibitors of AI-2.

Figure 14:
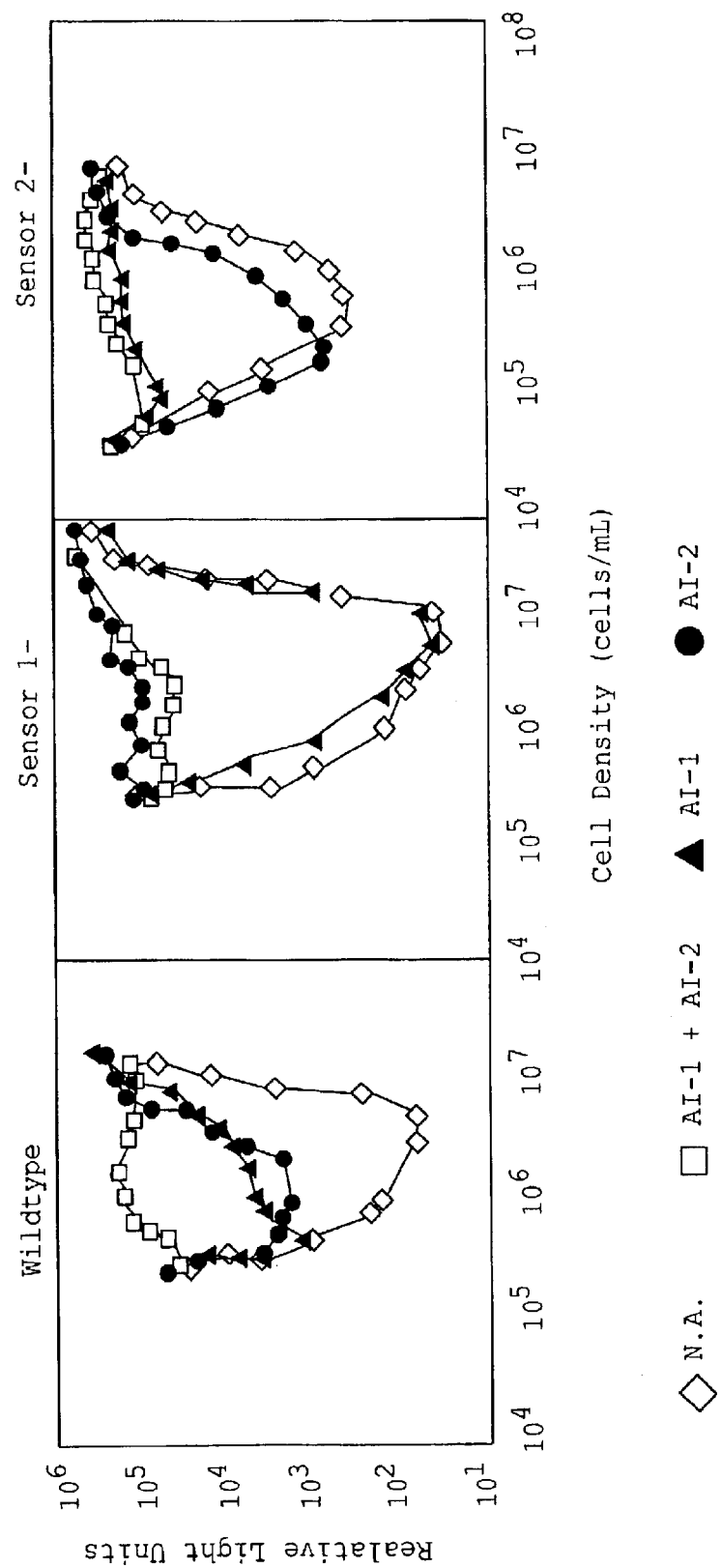
FIG. 14 is a graph representing response phenotypes of *V. harveyi* wild type and lux regulatory mutants. At the first time point, cell-free culture fluids (10%), or nothing (N.A.) was added. Wild type, cell-free culture fluid (AI-1+AI2); LuxS⁻ cell-free culture fluid (AI-1); LuxM⁻ cell-free culture fluid (AI-2). Relative light units are defined as cpm×10³/CFU/ml.

*V. harveyi* strains containing separate mutations in Lux genes L or M, or in Lux genes S or Q, lack the ability to synthesize or detect autoinducer-1 or autoinducer-2, respectively. Use of strain BB170, which is sensor 1–, sensor 2+ (LuxN–, LuxQ+) allows detection of autoinducer-2 in diverse bacteria The light emission response of wild type, LuxN– and LuxQ– phenotypes to increasing cell density is shown in FIG. 14.

The strains described above are ideally suited for the preparation of a kit. Such a kit may comprise a carrier compartmentalized to receive one or more containers such as vials, tubes, and the like, each of the containers comprising one of the separate elements to be used in the method. The container may comprise a strain of bacteria capable of detecting the presence of an autoinducer. Preferably, the bacterial strain is capable of providing a signal in the presence of autoinducer-2. More preferably, the desired strain lacks the ability to detect AI-1 (sensor 1–) and to synthesize AI-2. Thus, the kit may provide a luxN– and luxS– strain of *V. harveyi* designated MM32 for identifying autoinducer-2 as well as inhibitors of autoinducer-2 and the quorum-sensing pathway.

Methods for Detecting a Bacterial Biomarker

The present invention provides methods of using autoinducer-2 analogs to identify and regulate the expression of bacterial biomarkers in bacteria. The method is particularly useful for identifying a biomarker of pathogenic bacteria, which are thought to express an antigenic determinant or other biomarker in response to increased autoinducer concentration in the surrounding environment. Thus the present invention provides a method for identifying such a biomarker by exposing a bacterium to an autoinducer-2 analog and assaying for the presence of the biomarker through use of a labeled nucleic acid or other biomolecule, such as an antibody.

The method can be used in a screen to detect infections, for example. In addition, the method of the invention can be used to analyze differential gene expression in a bacterial cell following contact with an autoinducer through comparison of the expression of genes in different cells.

The materials described above are ideally suited for the preparation of a kit. Such a kit may comprise a carrier compartmentalized to receive one or more containers such as vials, tubes, and the like, each container comprising one of the separate elements to be used in the method. A kit of the invention may contain a first container comprising isolated autoinducer-2. The isolated autoinducer-2 can be used to regulate the expression of a biomarker in a target bacterium. For example, autoinducer-2 can be used to induce expression of a particular biomarker that can then be identified by a probe. Thus, the kit may contain a second container comprising a probe that can be detectably labeled. The kit may also have a third container comprising a reporter, such as a biotin-binding protein, such as avidin or streptavidin, bound to a label, such as an enzymatic, fluorescent, or radionuclide label. Other reporters and labels are well known in the art. For example, the kit of the invention may provide reagents necessary to perform nucleic acid hybridization analysis as described herein or reagents necessary to detect antibody binding to a target.

Regulation of Biofilm Formation

Bacteria can adhere to solid surfaces to form slimy, slippery coatings known as biofilms, which are a highly hydrated matrix of exopolymers, typically polysaccharide, and other biopolymers. The biofilm mode of existence, involving colony-forming sessile bacteria, accounts for a sizable portion of the biomass in many environments. In some instances, biofilm-associated forms of bacteria may outnumber their planktonic (free-swimming) equivalents by several orders of magnitude. The transition from a planktonic existence to growth attached to a surface occurs in response to many environmental factors, including long-term growth under conditions of nutrient deprivation or high osmolarity. Biofilms may contain either a single species, or multiple species of bacteria, and these can be organized into higher order structures (e.g. water/nutrient channels, cellular pillars, dense monolayers punctuated by microcolonies) that benefit the entire community. Biofilm colonies exhibit coordinated metabolic responses, such as spatially distinct gene expression in different regions of the biofilm, that contribute to their overall fitness. Biofilms allow bacteria to survive in hostile environments.

Bacterial biofilms are at the root of many persistent and chronic bacterial infections. Consequently, the prevention of colonization, and eradication of biofilm-associated bacteria is a major goal of modern medicine. Unlike single cells, biofilm formation can withstand exposure to most biocidal treatments. In the biofilm, the extracellular matrix (glycocalyx) provides a barrier that protects and isolates the microorganisms from biocides such as surfactants and antibiotics. In one study, biofilm cultures were able to withstand a dose of antibiotic twenty-fold greater than needed to eradicate planktonic cultures of the same bacteria. It also shields the resident microorganisms from host defense mechanisms such as antibodies and antigen processing by phagocytes.

Biofilm-associated infections have been implicated in a number of disease conditions. Examples include porstatitis, osteomyelitis, septic arthritis, and cystic fibrosis. In some of these diseases (e.g. septic arthritis), the biofilm can cause destruction of the host surface structure. In many of these conditions, the biofilm provides a reservoir of bacteria that can lead to chronic and recurrent infections, (sepsis). Biofilm formation can also be a complication in bioimplants, such as bone prostheses, heart valves, and pacemakers. Biofilm formation may compromise the function of the implant, or lead to serious bone or joint infections.

Because quorum sensing strongly influences biofilm formation, quorum-sensing blockers can impede formation of biofilms and substantially decrease the extent of biofilms that have already formed on a surface. Thus, by providing the structure of autoinducer-2 (AI-2) and analogs of AI-2, such as Structure I, II, III or IV, the present invention provides a new approach to inhibiting bacterial infections by regulating biofilm formation.

The invention further provides data indicating that AI-2 regulates bacterial biofilm formation. Null mutant strains of $V.$ harveyi lacking autoinducer-1 and autoinducer-2 activity (AI-1–/AI-2–) do not produce biofilm, unlike wild type, Al-1–/AI-2+ and AI-1+/AI-2– $V.$ harveyi strains. Addition of AI-1, AI-2 or Salmonella AI-2 to the medium allows (AI-1–/AI-2–) $V.$ harveyi to produce biofilm. Thus, the invention provides a way of regulating biofilm formation by contacting a bacterial cell with autoinducer-2 or an autoinducer-2 analog.

Furthermore, the unexpected finding that quorum-sensing blockers inhibit biofilm formation implies that compounds that exhibit quorum-sensing blocking in other systems, such as protease production, will also inhibit biofilm formation.

In another embodiment, the invention provides a method of removing a biofilm from a surface that comprises treating the surface with a compound of the invention. The surface is preferably the inside of an aqueous liquid distribution system, such as a drinking water distribution system or a supply line connected to a dental air-water system, where removal of biofilms can be particularly difficult to achieve. The compound is preferably applied to the surface either alone or together with other materials such as conventional detergents or surfactants.

A further embodiment of the invention is an antibacterial composition comprising a compound of the invention together with a bacteriocidal agent. In the antibacterial compositions, the compound of the invention helps to remove the biofilm while the bacteriocidal agent kills the bacteria. The antibacterial composition is preferably in the form of a solution or suspension for spraying and/or wiping on a surface.

In yet another aspect, the invention provides an article coated and/or impregnated with a compound of the invention in order to inhibit and/or prevent biofilm formation thereon. The article is preferably composed of plastic with the compound of the invention distributed throughout the material.

Synergistic Antibiotic Compositions

In a further embodiment, the invention provides a synergistic antibiotic composition comprising an antibiotic and an inhibitor of the quorum-sensing pathway of a microorganism, or a pharmaceutically-acceptable salt thereof, and one or more pharmaceutically acceptable carriers, adjuvants or vehicles.

The synergistic antibiotic composition of the invention can be used to treat infections in a warm-blooded animal caused by microorganisms possessing a quorum-sensing mechanism, which comprises administering to the animal a therapeutically effective amount of the synergistic antibiotic composition of this invention.

Surprisingly, we have found that combinations of inhibitors for one or more of the quorum sensing pathways with antibiotics effective against microorganisms containing the quorum sensing mechanism reduces the amount of antibiotic normally necessary for its therapeutic effect. Also, the combination may lower the therapeutically effective amount of the antibiotic so that it has a beneficial effect against the microorganism when ordinarily it was considered to have no effect at concentrations considered both effective and safe. Thus, another aspect of the instant invention is directed to a synergistic antibiotic composition comprising an antibiotic and an inhibitor of the quorum-sensing pathway of a microorganism. By "synergistic", we mean that the combination of the quorum sensing inhibitor lowers the dose of the antibiotic required to kill (in a bactericidal agent) or arrest the growth (in a bacteristatic agent) of the microorganism being treated in warm-blooded animal, or renders the antibiotic effective against the organism in an animal when it ordinarily is not effective.

Figure 13:
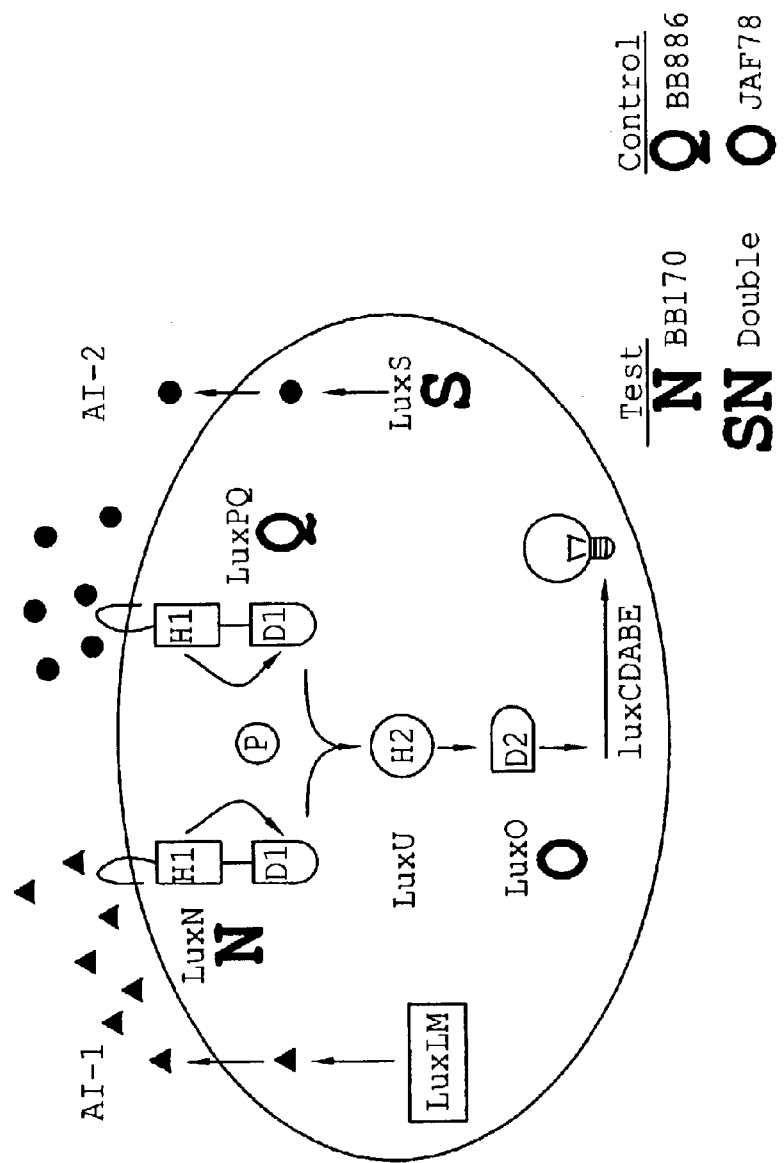
FIG. 13 provides a diagram of the hybrid quorum-sensing circuit of *Vibrio harveyi*. The AI-1 and AI-2 circuits are independently stimulated but integrate their signals for light expression. Each pathway, however, is also independently competent to generate light. This allows for reciprocal mutations in the LuxN or LuxQ sensors to be used to construct a reporter specific for AI-2 or AI-1, respectively.

By "inhibitor of the quorum-sensing pathway of a micro organism" we mean inhibitors that can either inhibit the production, or the response to, an autoinducer. Such inhibitors may inhibit one or more of the AI-1, AI-2 and the peptide-mediated quorum sensing pathways. For instance, inhibitors of the AI-2 pathway (depicted in FIG. 13) are molecules that either bind to or inhibit the production of the proteins derived from the LuxP, LuxS and LuxQ genes of the V. harveyi and their homologs in other species. The assays for detecting inhibitors of the AI-1, AI-2 and peptide-mediated sensing pathways appear in Examples 6, 4, and 7, respectively. For the AI-2 pathway, inhibitors are found by their inhibition of bioluminescence of mutant strains V. harveyi that are otherwise insensitive to the effects of AI-1. Inhibitors of the AI-1 pathway are also measured by their ability to inhibit bioluminescence of V. fischeri. Finally, inhibitors of the peptide-mediated quorum sensing pathway are detected by their ability diminish the production of the virulence factor δ-toxin from Staphlycoccus aureus as colonies of this bacteria grew to confluence.

Examples of inhibitors of the AI-1 quorum sensing pathway are analogs of N-acyl-L-homoserine lactones in which the N-acyl side chain has been modified, specifically:

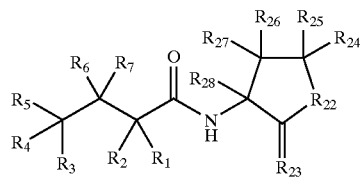

A modified N-butyryl-L-homoserine lactone compound of the structure V:

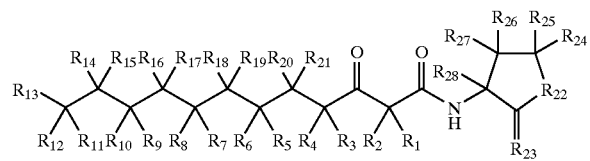

or a modified N-(3-oxododecanoyl)-L-homoserine lactone compound of the structure VI:

wherein $R_1$–$R_{22}$ are independently selected from the group consisting of $C_1$ to $C_4$ alkyl; a hydrogen atom, hydroxy, amino, and thiol;

$R_{22}$–$R_{23}$ are independently an oxygen or a sulfur atom; and $R_{24}$–$R_{28}$ are independently a hydrogen or a halogen atom.
These molecules are described in Davies et al., PCT Patent Application Publication No. WO98/58075, published Dec. 23, 1998, the entirety of which is incorporated herein by reference.

Other examples of inhibitors of AI-1 quorum-sensing pathways are halogenated firanones of the structure VII:

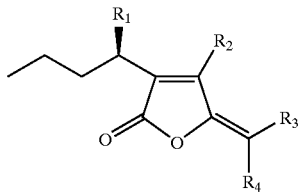

These halogenated furanones are produced by benthic marine macroalga D. pulchra. One particular example of such an inhibitor is 4-bromo-5-(bromomethylene)-3-(1-hydroxybutyl)-2-(5H)-furanone. These molecules are described in Manefield et al., Microbiology, 145, 283–291 (1999)).

Examples of the inhibitors of the AI-2 mediated quorum sensing pathway includes compounds of structures I, II, III and IV:

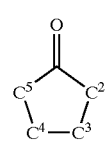

I wherein $C^2$ is additionally bonded to at least one substituent selected from hydrogen, hydroxyl, $C_{1-5}$ alkyl, $C_{2-5}$ alkenyl, $C_{2-5}$ alkanoyl, $C_{2-5}$ alkanoyloxy, heteroaryl, or forms a double bond with an oxygen atom or $C^3$; wherein $C^3$ is additionally bonded to at least one substituent selected from hydrogen, hydroxyl, $C_{1-5}$ alkyl, $C_{2-5}$ alkenyl, $C_{2-5}$ alkanoyl, $C_{2-5}$ alkanoyloxy, or forms a double bond with an oxygen atom or $C^2$; wherein $C^4$ is additionally bonded to at least one substituent selected from hydrogen, $C_{1-5}$ alky, $C_{2-5}$ alkanoyl, $C_{2-5}$ alkanoyloxy, or forms a double bond with an oxygen atom or $C^5$; and wherein $C^5$ is additionally bonded to at least one substituent selected from hydrogen, $C_{1-5}$ alkyl, $C_{2-5}$ alkanoyl, $C_{2-5}$ alkanoyloxy, or forms a double bond with an oxygen atom or $C^4$; wherein at least one of $C^2$, $C^3$, $C^4$ or $C^5$ is bonded to a substituent selected from hydroxyl, $C_{1-5}$ alkyl, $C_{2-5}$ alkenyl, $C_{2-5}$ alkanoyl, and heteroaryl; and wherein at most one carbon-carbon double-bond is present in the ring of Structure I;

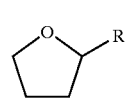

II wherein R is a $C_{1-5}$ alkoxyl group;

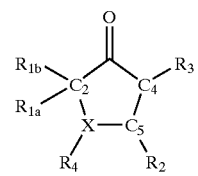

III wherein X is either an oxygen, sulfur or nitrogen atom; $R_{1a}$ is either hydrogen, hydroxy, alkyl, acyl, amido, hydroxyl, amino, thio, or aryl; $R_{1b}$ is either hydrogen, hydroxy, alkyl, acyl, arido, hydroxyl, amino, mercapto, thio, or aryl, or $R_{1a}$ and $R_{1b}$ can include the same atom bonded to $C_2$ to form a double bond with $C_2$; $R_2$ is hydrogen, alkyl, or halogen; $R_3$ is hydrogen, alkyl, acyl, amido, hydroxyl, amino, thio, or aryl; $R_4$ is hydrogen or alkyl, if X is nitrogen, or is absent if X is oxygen or sulfur, and wherein $C_4$ and $C_5$ can be further joined by a double bond;

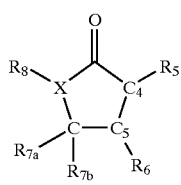

IV wherein X is oxygen, sulfur or nitrogen; $R_{7a}$ is hydrogen, hydroxy, alkyl, acyl, amido, hydroxyl, amino, thio, or aryl; $R_{7b}$ is hydrogen, hydroxy, alkyl, acyl, amido, hydroxyl, amino, mercapto, thio, or aryl, or $R_{7a}$ and $R_{7b}$ can together form a double bond; $R_6$ is hydrogen, alkyl, or halogen; $R_7$ is hydrogen, alkyl, acyl, amido, hydroxyl, amino, thio, or aryl; $R_8$ is hydrogen, if X is nitrogen, or is absent if X is oxygen or sulfur; and wherein $C_4$ and $C_5$ can be further joined by a double bond.

Examples of inhibitors of peptide-mediated quorum sensing molecules include chemically-modified pheromones of *Staphylococcus epidermidis* that are competent inhibitors of the *Staphylococcus aureus* agr (accessory gene regulator) system. These inhibitors include molecules of the structures VIII and IX:

Further inhibitors of peptide-mediated quorum sensing are compounds of the structure:

(cyclo)-YSTCDFIM; (X)
(cyclo)-GVNACSSLF; (XI)
(cyclo)-GVNASSSLF; (XII) or
(cyclo)-GVNA(DAPA)SSLF, (XIII)

wherein in these four structures the C-terminal carbonyl group forms 1) a thiolactone with the sulfur atom of the cysteine residue (YSTCDFIM and GVNACSSLF); 2) a lactone group with the oxygen atom of the first serine residue (GVNASSSLF); or 3) an anide bond with amino group of the diaminoproprionic acid (DAPA) residue (GVNA(DAPA)SSLF). The synthesis of these molecules and activity of these molecules have been described in Mayville et al., Proc. Natl. Acad. Sci. USA, 96, 1218–1223 (1999).

Further embodiments of the instant synergistic antibiotic composition include those wherein the inhibitor inhibits the AI-1 quorum sensing pathway. Of this latter embodiment, further specific embodiments include those where the inhibitor is a halogenated 2(5H) furanone of Structure VII above, or when the inhibitor is either a modified N-buturyl-L-homoserine lactone of Structure VIII above or a modified N-(3-oxododecanoyl)-L-homoserine lactone of Structure IX above.

Another group of embodiments occurs when the inhibitor of the synergistic antibiotic composition is one that inhibits the AI-2 quorum sensing pathway, and more so when it is of the Structure III or Structure IV above. One further embodiment is when the inhibitor is 2-ethyl-4-hydroxy-5-methyl-

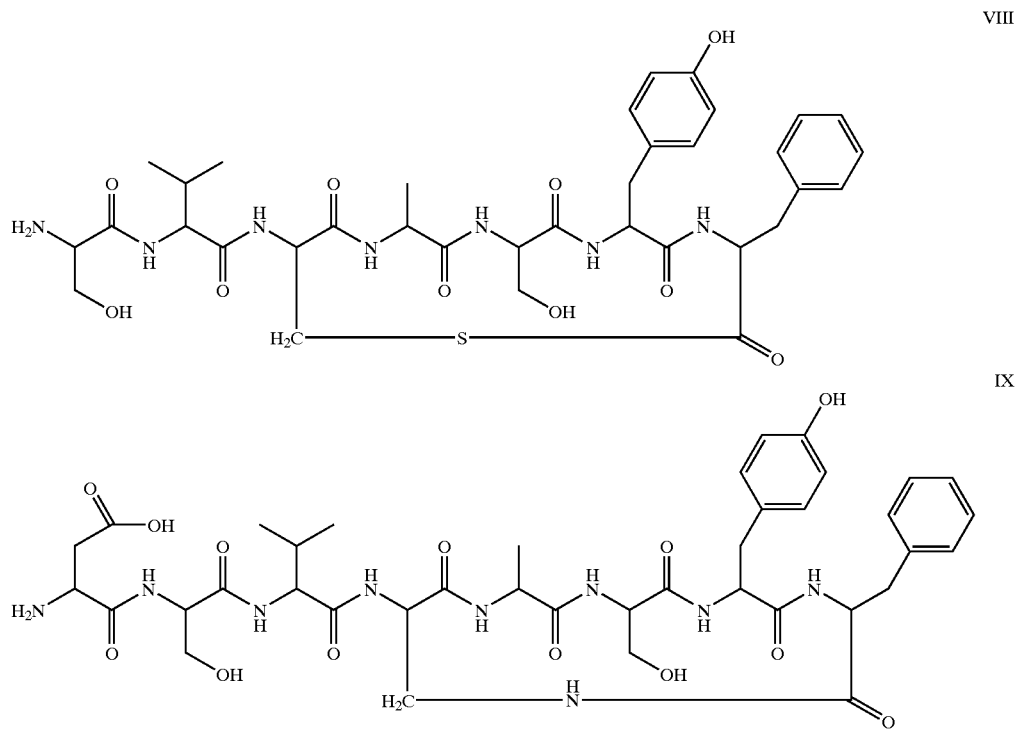

VIII

IX (cyclo-SVCASYF)
(cyclo-DSV(DAPA)ASYF)

These modified pheromones were especially effective in inhibiting production of δ-toxin in the *S. aureus* strains as described in Otto et al., FEBS Letters, 450 257–262 (1999).

3(2H)-furanone. Another group of embodiments for a composition containing an AI-2 inhibitor occurs when 1) the antibiotic is a penicillin, and further when the penicillin is ampicillin; 2) the antibiotic is a quinoline, and further when the quinoline is ciprofloxacin; 3) the antibiotic is vancomycin; and 4) the antibiotic is a sulfonamide, and further when the sulfonamide is sulfisoxaxole.

Synergistic antibiotic compositions where the inhibitor inhibits the peptide-mediated quorum sensing pathway constitute another embodiment of the instant synergistic compositions. Within this latter embodiment are those compositions that include inhibitors of the Structure (VIII) and (IX) above, and alternatively those that contain inhibitors of Structures (X) through (XIII) above.

Yet another group of embodiments of the instant synergistic antibiotic compounds occurs when 1) the antibiotic is a penicillin, and further when the penicillin is ampicillin; 2) the antibiotic is a quinoline, and further when the quinoline is ciprofloxacin; 3) the antibiotic is vancomycin; and 4) the antibiotic is a sulfonamide, and further when the sulfonamide is sulfisoxaxole.

Further embodiments of the instant pharmaceutical compositions track those set forth above for the synergistic antibiotic compositions of this invention, as determined by the identity of the inhibitors and antibiotics in the pharmaceutical composition.

A further aspect of this invention is directed to a method of treating infections in a warm-blooded animal caused by microorganisms possessing a quorum-sensing mechanism that comprises administering to the animal a therapeutically effective amount of the synergistic antibiotic composition of this invention. It will be understood that the amount of antibiotic administered in the instant method will normally be less than that administered if the inhibitor compound were not present. The amount normally necessary to treat an infection by a particular microorganism can be determined by using the antibiotic susceptibility assay of Example 8, and also in the case of known antibiotics by consulting sources such as J. Hardman and L. Limbard, Editors-in-Chief, Goodman and Gilman's The Pharmacological Basis of Therapeutics, Ninth Edition, McGraw-Hill, New York, (1996), especially at pages 1027 through 1223. Of course, the synergistic antibiotic composition administered in this method can also be in the form of a pharmaceutical composition of this invention. Also, the synergistic antibiotic compound can be administered to warm-blooded animal infected with a microorganism possessing a quorum sensing pathway that would otherwise be refractory to the treatment with the antibiotic alone if screens such as the one set forth in Example 8 below indicate that the synergistic antibiotic composition does indeed have activity against that microorganism.

Further embodiments of this method includes methods for treating infections in warm blooded animals caused by =Streptococcus pyogenes, and especially so when the inhibitor that is administered is one that inhibits the AI-2 quorum sensing pathway. Of this latter embodiment, further embodiments include those where the antibiotic is vancomycin, when the antibiotic is a quinoline antibiotic, for example, ciprofloxacin; or when the antibiotic is a sulfonamide, for example, sulfisoxazole.

Yet another embodiment of the instant method includes methods for treating infections in warm blooded animals caused by Staphylococcus aureus, and especially so when the inhibitor inhibits the AI-2 quorum-sensing pathway. Of this latter embodiment, further embodiments include those wherein the antibiotic is a penicillin, and in particular when the antibiotic is ampicillin.

Medical Devices

In another embodiment, the compounds and synergistic antibiotic compositions of the invention can be used to inhibit bacterial cell growth and/or biofilm formation on a medical device. Percutaneous devices (such as catheters) and implanted medical devices (e.g., pacemakers, vascular grafts, stents, and heart valves) commonly serve as foci for bacterial infection. The tendency of some microorganisms to adhere to and colonize the surface of the device promotes such infections, which increase the morbidity and mortality associated with use of the devices. Consequently, physicians have great interest in development of surfaces that are less prone to bacterial colonization.

The synergistic antibiotic compositions of the invention can be used to inhibit bacterial cell growth and biofilm formation on substrates used to manufacture medical devices associated with noninvasive and invasive medical procedures. Such substrates include tubular, sheet, rod and articles of proper shape for use in a number of medical devices such as vascular grafts, aortic grafts, arterial, venous, or vascular tubing, vascular stents, dialysis membranes, tubing or connectors, blood oxygenator tubing or membranes, surgical instruments, ultrafiltration membranes, intra-aortic balloons, stents, blood bags, catheters, sutures, soft or hard tissue prostheses, synthetic prostheses, prosthetic heart valves, tissue adhesives, cardiac pacemaker leads, artificial organs, endotracheal tubes, lenses for the eye such as contact or intraocular lenses, blood handling equipment, apheresis equipment, diagnostic and monitoring catheters and sensors, biosensors, dental devices, drug delivery systems, or bodily implants of any kind. For example, arthroscopic surgery is routinely performed with use of medical devices that minimize the invasiveness of the procedure. Such devices include, for example, ultrathin microfiberoptic endoscopes that offer the laryngologist unique access to the limited spaces of the temporal bone and skull base. In another example, a stent supplemented with a composition of the invention that deters bacterial infections resulting from the presence of the implanted stent can be constructed. Stents are used to maintain an open lumen in tissues including the tracheo-bronchial system, the biliary hepatic system, the esophageal bowel system, and the urinary tract system. U.S. Pat. No. 5,637,113 issued to Tartaglia, and incorporated herein by reference, teaches a stent with a sheet of polymeric film wrapped around the exterior. With regard to the present invention, the film may be loaded or coated with a compound or composition of the invention. Alternatively, the material used to manufacture the stent can be impregnated with a composition of the invention.

A medical device may be further supplemented with, for example, one or more antibodies, analgesics, anticoagulants, anti-inflammatory compounds, antimicrobial compositions, cytokines, drugs, growth factors, interferons, hormones, lipids, demineralized bone or bone morphogenetic proteins, cartilage inducing factors, oligonucleotides polymers, polysaccharides, polypeptides, protease inhibitors, vasoconstrictors or vasodilators, vitamins, minerals, stabilizers and the like. Supplemented, as used herein, includes medical devices that are impregnated, infused, coated, covered, layered, permeated, attached or connected with a compound or synergistic antibiotic composition of the invention. Methods for immobilizing biomaterials to a medical device are discussed in U.S. Pat. No. 5,925,552, which is incorporated herein by reference. Additional methods of coating surfaces of medical devices with antimicrobial compositions are taught in U.S. Pat. No. 4,895,566 (a medical device substrate carrying a negatively charged group having a pKa of less than 6 and a cationic antibiotic bound to the negatively charged group); U.S. Pat. No. 4,917,686 (antibiotics are dissolved in a swelling agent which is absorbed into the matrix of the surface material of the medical device); U.S. Pat. No. 4,107,121 (constructing the medical device with ionogenic hydrogels, which thereafter absorb or ionically bind antibiotics); U.S. Pat. No. 5,013,306 (laminating an antibiotic to a polymeric surface layer of a medical device); and U.S. Pat. No. 4,952,419 (applying a film of silicone oil to the surface of an implant and then contacting the silicone film bearing surface with antibiotic powders). U.S. Pat. No. 5,902,283 further discloses a method for coating a medical device with an antimicrobial agent such that the agent penetrates the exposed surfaces of the device and is impregnated throughout the material of the device.

The desirability of coating medical devices such as, inter alia, surgical implants, sutures and wound dressings with pharmaceutical agents is well documented in the art. Such coated devices could theoretically provide a means for locally delivering pharmaceutical or therapeutic agents at the site of medical intervention to treat a variety of diseases. For example, surgical implants or sutures coated with antibiotics can provide local delivery of antibiotic directly at an implantation or suture site, thereby decreasing the onset of infection following the surgical intervention. Thus, compounds and synergistic antibiotic compositions of the invention can supplement medical devices used for implantation in guided tissue regeneration (GTR) procedures by preventing or ameliorating infections at the site of tissue regeneration. Such devices and procedures are currently used by those skilled in the medical arts to accelerate tissue regeneration following invasive surgical procedures. For example, nonresorbable or bioabsorbable membranes are used to accelerate tissue regeneration by promoting the repopulation of the wound area with cells that form the architectural and structural matrix of the tissue. The compounds and syngeristic antibiotic compositions of the invention can be used to inhibit bacterial growth at the site of tissue regeneration. For example, a compound or syngeristic antibiotic composition can be used to aid periodontal tissue regeneration in a human or lower animal by placing a composition containing a bioresorbable polymer, leachable solvent, and a compound or syngeristic composition of the invention, at a site in need of periodontal tissue regeneration in a human or other mammal such that the composition is effective for inhibiting bacterial cell growth by releasing a therapeutically-effective amount of the compound or syngeristic composition at the site.

A medical device supplemented with a compound or composition of the invention is further useful for promoting tissue growth during the process of tissue engineering. By "tissue engineering" is meant the creation, design, and fabrication of biological prosthetic devices, in combination with synthetic or natural materials, for the creation, augmentation, or replacement of body tissues and organs. Thus, a medical device supplemented with a compound or composition of the invention includes cell-containing or cell-free device that induce the regeneration of functional human tissues when implanted at a site that requires regeneration. As previously discussed, biomaterial-guided tissue regeneration can be used to promote cell proliferation in, for example, digestive tract tissue for treatment of gastric ulcers or the pathogenic result of Crohn's disease. A compound or synergistic antibiotic composition of the invention can be used to promote the growth of reconstituted tissues assembled into three-dimensional configurations at the site of a wound or other tissue in need of such repair by inhibiting pathogenic bacterial cell growth at the site. A compound or synergistic antibiotic composition can be included with the device upon implantation or the device itself can be impregnated with a compound or synergistic antibiotic composition such that the compound or synergistic antibiotic composition is released slowly during tissue regeneration.

A compound or synergistic antibiotic composition of the invention can be included in external or internal medical devices containing human tissues designed to replace the function of diseased internal tissues. This approach involves isolating cells from the body, placing them on or within structural matrices, and implanting the new system inside the body or using the system outside the body. A compound or synergistic antibiotic composition invention can be included in such matrices to promote the growth of tissues contained in the matrices by inhibiting bacterial growth. For example, compound or synergistic antibiotic composition of the invention can be included in a cell-lined vascular graft to inhibit bacterial cell growth and biofilm formation in the graft. It is envisioned that the invention can be used to augment tissue repair, regeneration, and engineering in products, such as epithelial tissue, cartilage and bone, central nervous system tissues, muscle, liver, and pancreatic islet (insulin-producing) cells.

A specific, non-limiting example is the use of the invention in promoting the growth of skin graft replacements that are used as a therapy in the treatment of burns and ulcers. Burn victims are particularly susceptible to infections resulting from skin graft treatments. The compounds or synergistic antibiotic composition of the invention can be included during tissue engineering of a skin graft such that the graft is free of bacterial infection when transplanted to a burn victim. Compounds or synergistic antibiotic compositions of the invention can also be included at the site of transplant to further minimize the possibility of infection. Thus, the invention encompasses inhibiting bacterial cell growth and biofilm formation during preparation and application of a tissue graft using an effective amount of a compound or synergistic antibiotic composition of the invention.

Additionally, or alternatively, the synergistic antibiotic compositions of the invention may be incorporated into a biodegradable carrier. For example, such a carrier is described in U.S. Pat. No. 5,788,979. Time-controlled release of the compound or composition is attributable to the degradation or disintegration of the carrier itself, so that the drug or other agent remains captive within the carrier until it is dispensed or released, i.e., freed from its host, by progressive dissolution upon continuing diffusion of the carrier from the reservoir. The compound or composition tends to act locally rather than systemically in such an arrangement.

It is further envisioned that the synergistic antibiotic compositions of the invention can be used to aid wound repair. For example, U.S. Pat. No. 6,117,485 describes a foaming tissue sealant for treating wounded tissue in a subject. The sealant can be formulated to include a compound or composition of the invention. The sealant is useful for significantly diminishing or preventing blood or fluid loss from injured tissues, organs or blood vessels, while also providing a barrier to infection.

It is further envisioned that the synergistic antibiotic compositions of the invention can be used to inhibit bacterial cell growth and biofilm formation in or on products or devices used for personal hygiene. Soap, toothpaste, dental floss, laundry detergent or moisturizing lotion are examples of consumer products that would benefit from the inclusion of a compound or synergistic antibiotic composition of the invention. In addition, such a compound or composition can be included in a personal hygiene device such as a toothbrush, tongue depressor, or any other such device which comes in contact with a tissue.

The following description sets forth the general procedures involved in practicing this aspect of the present invention. To the extent that specific materials are mentioned, it is merely for purposes of illustration and is not intended to limit the invention. Unless otherwise specified, general cloning procedures, such as those set forth in Sambrook et al., *Molecular Cloning*, Cold Spring Harbor Laboratory (1989) (hereinafter "Sambrook et al.") or Ausubel et al. (eds) *Current Protocols in Molecular Biology*, John Wiley & Sons (1998) (hereinafter "Ausubel et al.") are used.

EXAMPLES

Example 1
Quorum Sensing in *Escherichia coli* and *Salmonella typhimurium*

Assay conditions. *V. harveyi* reporter strain BB170 (with quorum-sensing phenotype Sensor 1⁻, Sensor 2⁺) can induce lux expression only through Signaling System 2. Addition of 10% cell-free spent culture fluid prepared from *V. harveyi* strain BB152 (which contains the autoinducer-2 analog) stimulates a roughly 1000-fold increase in luminescence, an increase that is normalized to 100% activity in FIG. 1.

*E. coli* strain AB1157 and *S. typhimurium* strain LT2 were each grown for 8 h in LB broth or LB broth containing 0.5% glucose and the *E. coli* or *S. typhimurium* cells removed from the growth medium. Addition of 10% cell-free culture fluid maximally induced luminescence in the reporter strain BB170, similar to culture fluids from *V. harveyi* BB152 (FIG. 1A). Specifically, *E. coli* AB1157 produced 106% and *S. typhimurium* produced 237% of the *V. harveyi* BB152 activity.

In control experiments, *E. coli* and *S. typhimurium* grown in LB without added glucose did not produce the signaling factor, nor did blank solutions containing 10% (v/v) of LB medium containing 0.5% glucose. Glucose, amino acids, cAMP, acetate, homoserine lactone, -ketoglutarate and other keto acids that are known to be excreted lacked activity.

Analogous experiments were performed with the *V. harveyi* reporter strain BB886 (Sensor 1⁺, Sensor 2⁻). *V. harveyi* BB886 is defective in its response to signaling molecules that act through the Signaling System 2 detector, but it is an otherwise wild type strain (Bassler et al., Mol. Microbiol. 13: 273–286, 1994). FIG. 1B shows the normalized 100% activation of *V. harveyi* BB886 by cell-free spent culture fluids prepared from *V. harveyi* BB120. *V. harveyi* BB120 produces the System 1 autoinducer N-(3-hydroxybutanoyl)-L-homoserine lactone (Bassler et al., 1993, supra). Addition of *S. typhimurium* LT2 and *E. coli* AB1157 cell-free culture fluids to *V. harveyi* strain BB886 caused a 5% and a 1% increase above the control level (FIG. 1B). Together the results of FIGS. 1A and 1B show that the signaling molecule produced by *E. coli* and *S. typhimurium* acts specifically through *V. harveyi* Signaling System 2 and not some other, unidentified pathway.

FIG. 2 shows that viable *E. coli* AB1157 and *S. typhimurium* LT2 are Required for Secretion of the Signaling Molecule.

Growth of *E. coli* AB1157 and *S. typhimurium* LT2 in LB medium containing glucose do not simply remove some pre-existing inhibitor of induction of luminescence. Washed *E. coli* and *S. typhimurium* cells added directly to the luminescence assay.

*E. coli* AB1157 and *S. typhimurium* LT2 were grown for 8 h in LB containibg 0.5% glucose, the cells removed by centrifugation, and the cell pellets washed and resuspended in sterile *V. harveyi* luminescence assay medium. *E. coli* AB1157 or *S. typhimurium* LT2 cells ($1\times10^6$ cells) were added to the diluted *V. harveyi* BB170 culture at the start of the experiment.

The presence of washed *E. coli* AB1157 or *S. typhimurium* LT2 cells fully induces LUX expression in *V. harveyi* BB170 (FIG. 2, left-hand bar in each series)(821-fold and 766-fold, respectively). Identical aliquots of the washed *E. coli* or *S. typhimurium* cells killed with short wave ultraviolet light before addition to the assay did not stimulate luminescence (FIG. 2, right-hand bar for each strain). Taken together, the results show that *E. coli* AB1157 and *S. typhimurium* LT2 cells produce the stimulatory factor themselves during the experiment.

*E. coli* DH5α Does Not Produce the Signaling Activity. Clinical isolates of *E. coli* and Salmonella also produce the signaling compound. Ten clinical isolates of Salmonella and five pathogenic isolates of *E. coli* O157 were assayed and all produced the activity. It was conceivable that the signal was some normal byproduct of glucose metabolism that simply diffuses out of the cells. This is not the case however, because we show that *E. coli* DH5α, which is equally capable of utilizing glucose as *E. coli* AB1157 and *S. typhimurium* LT2, does not produce the signaling activity. FIG. 1A demonstrates that unlike *E. coli*, AB1157 and *S. typhimurium* LT2, the addition of 10% cell-free culture fluid prepared from *E. coli* DH5α grown 8 h in LB containing 0.5% glucose does not stimulate light production in *V. harveyi* BB170. Similarly, inclusion of washed viable or killed *E. coli* DH5α cells in the luminescence assay does not stimulate *V. harveyi* BB 170 to produce light (FIG. 2). The inability of *E. coli* DH5α to produce the activity indicates that this highly domesticated strain lacks the gene or genes necessary for either the production or the export of the signaling activity. We assayed other laboratory strains of *E. coli* for the signaling activity (Table 1). Only *E. coli* DH5α was completely defective in producing the extracellular signal.

The induction of luminescence in *V. harveyi* reporter strain BB 170 by cell-free culture fluids from *V. harveyi*, *S. typhimurium* and *E. coli* is shown. Cell-free culture fluids were prepared from various strains of *V. harveyi*, *S. typhimurium* and *E. coli* as described and tested for production of a signaling substance that could stimulate light production in the reporter strain *V. harveyi* BB170. The level of *V. harveyi* stimulation was normalized to 100%. The data for the 5 h time point are shown.

TABLE 2

| Species and Strain | Induction of Luminescence (%) |
| --- | --- |
| *V. harveyi* BB152 | 100 |
| *S. typhimurium* LT2 | 237 |
| *E. coli* AB1157 | 106 |
| *E. coli* DH5α | 5 |
| *E. coli* JM109 | 76 |
| *E. coli* MG1655 | 100 |
| *E. coli* MC4100 | 93 |

Glucose Regulates the Production and Degradation of the Signaling Factor by *S. typhimurium* LT2. Cell-free culture fluids from *S. typhimurium* LT2 and *E. coli* AB1157 cells grown in LB without added glucose did not stimulate the expression of luminescence in the reporter strain, indicating that metabolism of glucose is necessary for the production of the signal. We tested other carbohydrates, and in general, growth in the presence of PTS sugars (see Postma et al., in *Escherichia coli and Salmonella Cellular and Molecular Biology*, S. C. Niehardt (ed), Am. Soc. Microbiol., Washington D.C., pp. 1149–1174, 1996) enabled *E. coli* AB1157 and *S. typhimurium* LT2 to produce the signal. Of the sugars tested, growth on glucose induced the synthesis of the highest level of activity. Growth on other carbon sources, for example TCA cycle intermediates and glycerol did not induce significant production of the signaling activity.

Figures 3A, 3B:
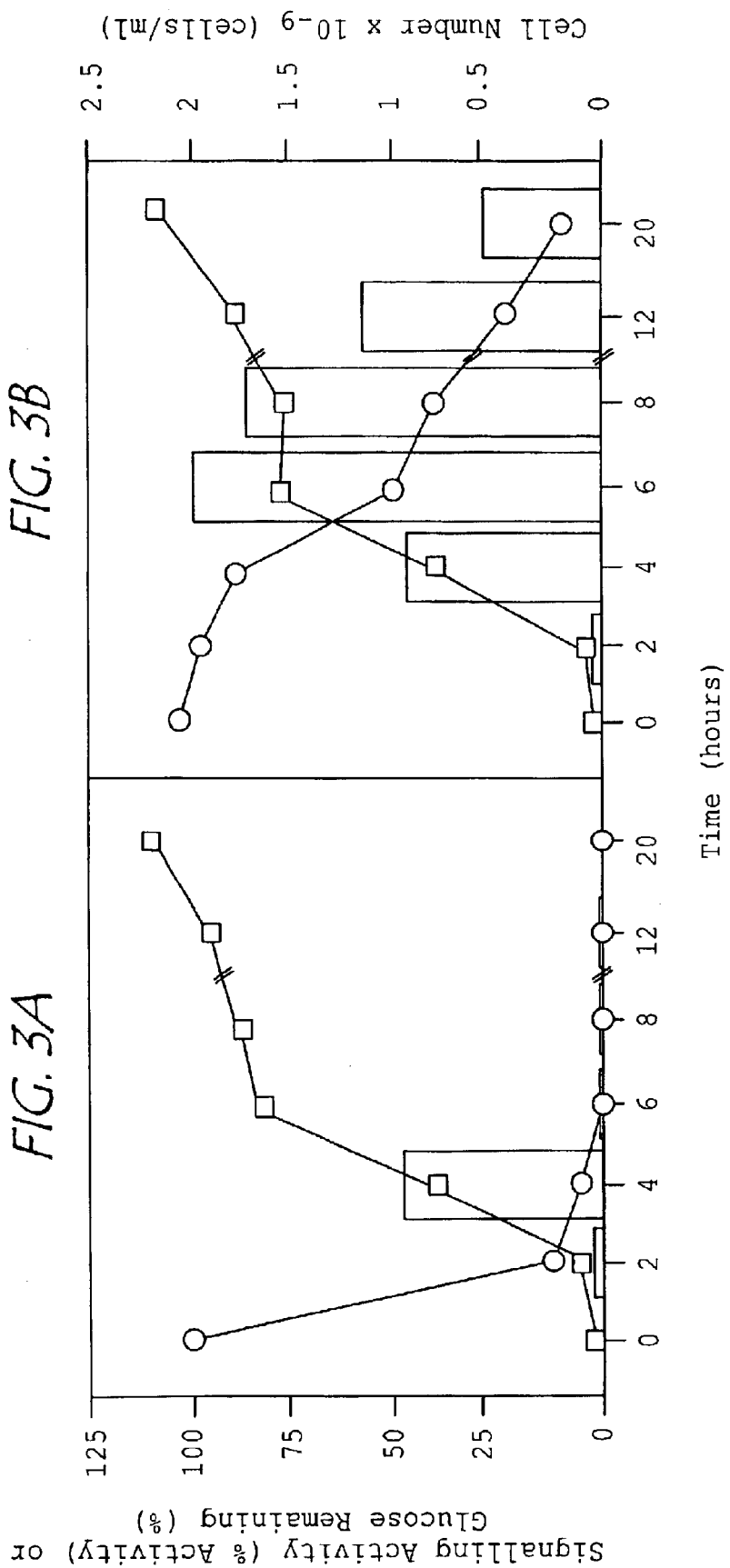
FIG. 3. Effect of glucose depletion on the production and degradation of the autoinducer-2 signaling activity by S. typhimurium LT2. S. typhimurium LT2 was grown in LB medium containing either 0.1% glucose (FIG. 3A) or 0.5% glucose (FIG. 3B). At the specified times cell-free culture fluids were prepared and assayed for signaling activity in the luminescence stimulation assay (Bars), and the concentration of glucose remaining (circles). The cell number was determined at each time by diluting and plating the S. typhimurium LT2 on LB medium and counting colonies the next day (squares). The signaling activity is presented as the percent of the activity obtained when V. harveyi cell-free spent culture fluids are added. These data correspond to the 5 h time point in the luminescence stimulation assay. The glucose concentration is shown as % glucose remaining. Cell number is cells/ml×10⁻⁹. The symbol \\ indicates that the time axis is not drawn to scale after 8 h.

We tested whether the presence of glucose was required for the cells to continue to produce the signal. FIG. 3 shows results with *S. typhimurium* LT2 grown in LB containing limiting (0.1%) and non-limiting (0.5%) glucose concentrations. FIG. 3A shows that when glucose is limiting, *S. typhimurium* LT2 produces the signal in mid-exponential phase (after 4 h growth), but stops producing the signaling activity once glucose is depleted from the medium. FIG. 3B shows that when glucose does not become limiting, *S. typhimurium* LT2 produces greater total activity and continues to produce the signaling activity throughout exponential phase, with maximal activity at 6 h growth. Furthermore, the Figure also shows that the signaling activity synthesized by mid-exponential phase cells is degraded by the time the cells reach stationary phase. In conditions of limiting glucose, no activity remained at stationary phase, and when glucose was plentiful, only 24% of the activity remained. Increasing the concentration of glucose in the growth medium did not change these results, i.e., the activity was secreted during mid-exponential growth, and severely reduced activity remained in the spent culture fluids by stationary phase.

In sum, the results presented in this example show that *E. coli* and *S. typhimurium* produce a signaling substance that stimulates one specific quorum-sensing system in *V. harveyi*. Many other bacteria have previously been assayed for such an activity, and only rarely were species identified that are positive for production of this factor (Bassler et al., 1997, supra). Furthermore, as shown here, the *E. coli* and *S. typhimurium* signal is potent; these bacteria make activity equal to that of *V. harveyi*. The degradation of the *E. coli* and *S. typhimurium* signal prior to stationary phase indicates that quorum sensing in these bacteria is tuned to low cell densities, suggesting that quorum sensing in *E. coli* and *S. typhimurium* is regulated so that the response to the signal does not persist into stationary phase. Additionally, quorum sensing in *E. coli* and *S. typhimurium* is influenced by several environmental factors. The production and the degradation of the signal are sensitive not only to growth phase but also to the metabolic activity of the cells. These results indicate that the quorum-sensing signal in *E. coli* and *S. typhimurium* has two functions; it allows the cells to communicate to one another their growth phase and also the metabolic potential of the environment.

Understanding the regulation of quorum sensing in *E. coli* and *S. typhimurium* is important for understanding community structure and cell/cell interactions in pathogenesis. In the wild, pathogenic *E. coli* and *S. typhimurium* may never reach stationary phase because dispersion is critical. It is therefore appropriate that quorum sensing in *E. coli* and *S. typhimurium* should be functioning at low cell density. This situation is in contrast to that of *V. fischeri*, the luminescent marine symbiont, where the quorum-sensing system is only operational at high cell densities; cell densities indicative of existence inside the specialized light organ of the host. The specific quorum-sensing systems of *V. fischeri* and *E. coli* and *S. typhimurium* appear appropriately regulated for the niche in which each organism exists. In both cases, quorum sensing could be useful for communicating that the bacteria reside in the host, not free-living in the environment. Additional complexity exists in the *E. coli* and *S. typhimurium* systems because these bacteria channel both cell density information and metabolic cues into the quorum-sensing circuit. Again, signals relaying information regarding the abundance of glucose or other metabolites could communicate to the bacteria that they should undergo the transition from a free-living mode to the mode of existence inside the host.

Under all the conditions we have tested, the signaling activity described in this example does not extract quantitatively into organic solvents and it does not bind to either a cation or anion exchange column. Preliminary characterization indicates that the signal is a small (less than 1000 MW) polar but apparently uncharged organic compound. The activity is acid stabile and base labile, it is heat resistant to 80 but not 100° C. Purification of the *E. coli, S. typhimurium* and *V. harveyi* signal is described in greater detail in the following examples.

Example 2
Regulation of Autoinducer Production in *Salmonella typhimurium*

In this example, the conditions under which *S. typhimurium* LT2 produces AI-2, the extracellular factor that stimulates lux expression in the *V. harveyi* Sensor 1$^-$, Sensor 2$^+$ reporter strain, are elucidated. Production of the signaling molecule by *S. typhimurium* occurs during growth on preferred carbohydrates that, upon utilization by the bacteria, result in a decrease in the pH of the medium. Lowering the pH of the growth medium in the absence of a preferred carbon source induces limited production of the factor, indicating that the cells are influenced by both the changing pH and the utilization of the carbon source. The signaling activity is degraded by the time the cells reach stationary phase, and protein synthesis is required for degradation of the activity. Osmotic shock following growth on an appropriate carbon source greatly increases the amount of activity present in the *S. typhimurium* culture fluids. This increased activity is apparently due to induction of synthesis of the autoinducer and repression of degradation of the activity. *E. coli* and *S. typhimurium* possess a protein called SdiA which is homologous to LuxR from *V. fischeri* (Wang et al., EMBO J. 10: 3363–3372, 1991; Ahmer et al., J. Bacteriol. 180: 1185–1193, 1998). SdiA is proposed to respond to an extracellular factor (Sitnikov et al., Proc. Natl. Acad. Sci. USA 93: 336–341, 1996; Garcia-Lara et al., J. Bacteriol. 178: 2742–2748, 1996), and it has been shown to control virulence factor production in *S. typhimurium* (Ahmer et al., 1998, supra). The analysis set forth below shows that the AI-2 autoinducer signaling activity does not function through the SdiA pathway.

Figure 4:
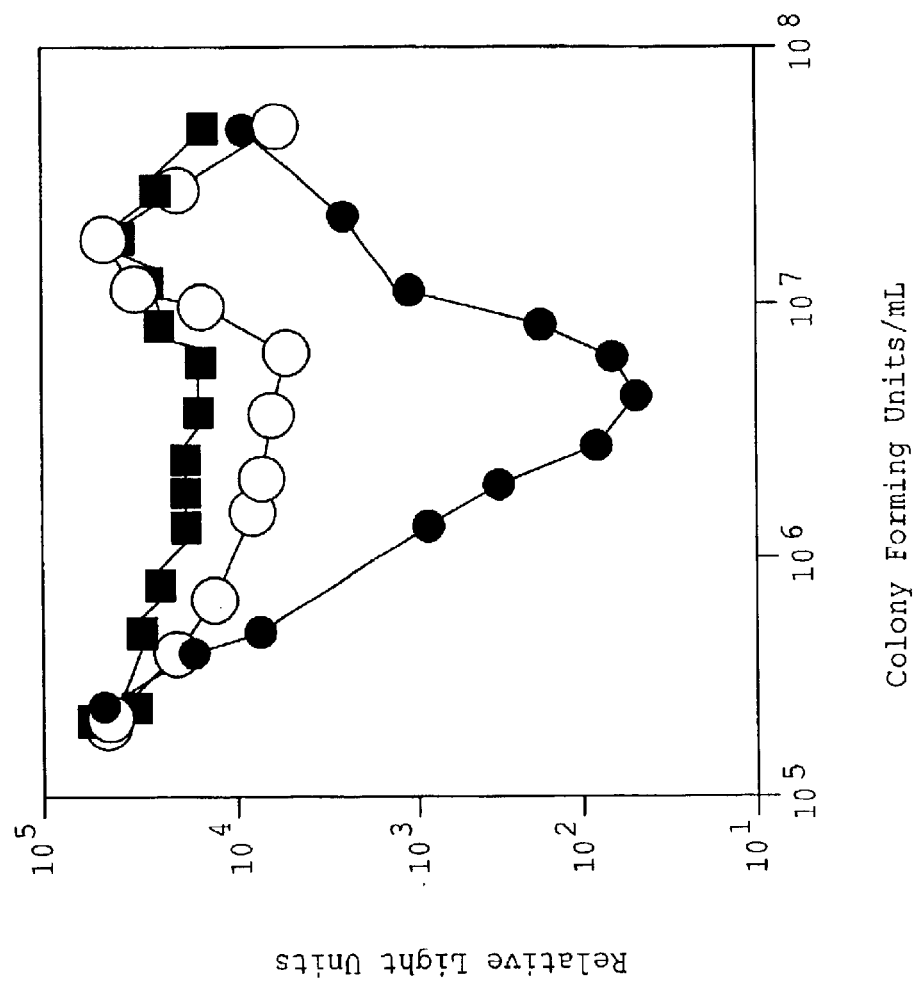
FIG. 4. Response curve of V. harveyi to AI-2 produced by V. harveyi and S. typhimurium. The V. harveyi reporter strain BB170 (Sensor 1⁻¹, Sensor 2⁺) was tested for its response to the addition of exogenous AI-2 made by V. harveyi strain BB152 (AI-1⁻ AI-2⁺) and to that made by S. typhimurium LT2. A bright culture of the reporter strain was diluted 1:5000 and either 10% (v/v) growth medium (closed circles), cell-free culture fluid from V. harveyi BB152 grown overnight in AB (open circles), or cell-free culture fluid from S. typhimurium LT2 grown for 6 h on LB+0.5% glucose (closed squares) was added at the start of the experiment. RLU denotes relative light units and is defined as (counts min⁻¹×1⁻³)/(colony-forming units ml¹).

*S. typhimurium* LT2 Produces an Autoinducer-like Activity. Example 1 demonstrates that *S. typhimurium* and *E. coli* strains produce a signaling activity that stimulates lux expression in *V. harveyi*, and the signaling molecule acts exclusively through the *V. harveyi* quorum-sensing System 2. FIG. 4 shows the induction of luminescence in the *V. harveyi* System 2 reporter strain BB170 (Sensor 1$^-$, Sensor 2$^+$). The control experiment shows the characteristic quorum-sensing behavior of *V. harveyi* (closed circles). Immediately after dilution into fresh medium, the light emitted per cell by *V. harveyi* drops rapidly, over 1000-fold. At a critical cell density, which corresponds to the accumulation of a critical concentration of endogenously produced autoinducer (AI-2) in the medium, the luminescence per cell increases exponentially, approximately three orders of magnitude, to reattain the pre-dilution level.

Addition of 10% cell-free culture fluid prepared from *V. harveyi* BB152 (AI-1⁻, AI-2⁺) caused the reporter strain to maintain a high level of light output following dilution (open circles). The increased light output is due to the *V. harveyi* BB170 cells responding to the presence of AI-2 in the cell-free culture fluids prepared from *V. harveyi* strain BB152 (Bassler et al., 1993, supra). Similarly, addition of cell-free culture fluid from *S. typhimurium* LT2 grown in LB+0.5% glucose induced luminescence in the reporter strain approximately 800-fold over the control level (solid squares). No activity similar to *V. harveyi* M-1 was produced by *S. typhimurium* LT2 under these conditions and there is no AI-1 or AI-2 activity in LB+0.5% glucose (see Example 1).

Environmental Factors Influence Autoinducer Production and Degradation in *S. typhimurium*. Control of autoinducer production in *S. typhimurium* is different than in other described quorum-sensing systems. FIG. 5A demonstrates three important aspects of the regulation of autoinducer production in *S. typhimurium*. First, no autoinducer activity is observed when *S. typhimurium* is grown for 6 h in LB in the absence of glucose. Second, growth in the presence of glucose for 6 h results in substantial production of autoinducer (760-fold activation of the reporter strain). Third, activity, while detectable, is severely reduced when the *S. typhimurium* culture is allowed to grow to stationary phase (33-fold activation of the reporter strain).

We subjected *S. typhimurium* LT2 to several different treatments including some environmental stresses in order to begin to understand what conditions favor autoinducer production versus those that favor autoinducer degradation. In the experiment presented in FIG. 5B, the *S. typhimurium* cells were induced for signal production by pre-growth in LB containing 0.5% glucose for 6 h. We have shown that under these conditions, the glucose is not depleted (Surette and Bassler, 1998). After the induction phase of growth, the culture fluid was removed and aliquots of the cells were resuspended and incubated for 2 h under a variety of conditions that are described in the description of FIG. 2. Following each of these treatments cell-free fluids were prepared and tested for activity on BB170.

It is important to note that in the results presented in FIG. 5B, the *S. typhimurium* were pre-induced for autoinducer production at the start of the experiment, i.e., their cell-free culture fluid activated the reporter strain 760-fold. FIG. 5B shows that removal of the pre-growth culture fluid from these cells and resuspension of the cells in LB without glucose, in 0.1 M NaCl (hypotonic conditions), or heat shock at 43° C. for 2 h resulted in no or very low autoinducer production. These results indicate that the above treatments result in termination of autoinducer production, or degradation of newly released autoinducer, or both.

In contrast to the above results, resuspension of pre-induced cells in fresh LB+glucose resulted in continued high-level production of autoinducer (735-fold activation of the reporter). Similarly, acidic pH promoted continued production of autoinducer (600-fold activation), and hypertonic osmotic shock (0.4 M NaCl) resulted in 1300-fold induction of the reporter. Increased AI-2 activity was only observed in the pH 5.0 fluids or 0.4 M NaCl osmotic shock fluids of cells that were already actively producing AI-2, i.e., if glucose was not included during the pre-growth, no measurable activity was produced following the identical 2 h treatments.

Shifting *S. typhimurium* cells from LB+glucose to 0.4 M NaCl resulted in an accumulation of AI-2 activity to a level much greater than that observed under any other condition tested. Below it is shown that *S. typhimurium* cells resuspended in 0.4 M NaCl increase the biosynthesis and/or release of autoinducer, and furthermore they apparently do not degrade significant quantities of the released activity. A similar increase in AI-2 production occurs when the *S. typhimurium* cells are resuspended in 0.4 M NaCl, 0.4 M KCl or 0.8M sucrose, indicating that the NaCl effect on AI-2 production is an osmotic one, not an ionic one. This apparent osmotic shock effect on the *S. typhimurium* cells was extremely useful because it enabled us to measure maximal release of autoinducer activity in the absence of loss due to degradation.

The Effect of Glucose on Signal Production in *S. typhimurium*. In Example 1 we showed that the continued presence of glucose was required for *S. typhimurium* to produce the quorum-sensing signaling factor. Because sugar utilization both increases the growth rate while decreasing the pH of the culture, we further analyzed the effect of metabolism of glucose, decreasing pH and increasing cell number on signal production by *S. typhimurium*. In the experiment presented in FIG. 6, we measured signal production, growth rate, and pH in growing *S. typhimurium* LT2 cultures containing limiting (0.1%) and non-limiting (1.0%) concentrations of glucose. In the data presented in FIG. 6, at various times, the level of autoinducer produced in both the cell-free culture fluids and in the corresponding 0.4 M NaCl osmotic shock fluids was measured and normalized for ×10⁹ cells. It should be noted that unlike in FIG. 5, the cells in this experiment were not pre-induced for signal production.

FIG. 6 shows that the pattern of production and disappearance of autoinducer observed in 0.4 M NaCl osmotic shock fluids mimics that observed in cell-free culture fluids. However, at every time point that autoinducer is produced, much greater activity is detected in the osmotic shock fluids than in the corresponding cell-free culture fluids. Under conditions of limiting (0.1%) glucose (FIGS. 6A, 6C and 6E), *S. typhimurium* produces the signaling activity between 2–4 h (Bars). However, the glucose becomes completely depleted at 4 h, and at that time production of the factor ceases (FIG. 6A). In contrast, when the cells are grown in 1.0% glucose (FIGS. 6B, 6D, and 6F), glucose is present in the medium throughout the entire experiment (FIG. 6B). Under these conditions, the cells continue to synthesize activity for 12 hours. Similar to the results shown in FIG. 5 and those reported in Example 1, almost no activity was observed in cell-free culture fluids or osmotic shock fluids from stationary phase cells at 24 h regardless of the glucose concentration.

*S. typhimurium* grows at roughly the same rate in both high and low glucose media during exponential phase. In fact, the *S. typhimurium* culture grown in high glucose medium does not reach the cell density achieved by the *S. typhimurium* grown in the low glucose medium (FIGS. 6C and 6D). Cell growth is probably inhibited in this culture by the dramatically reduced pH that occurs from increased glucose utilization. These results show that the higher level of activity produced by *S. typhimurium* in the LB containing 1% glucose is not due to higher cell number, but due to induction of signal production caused by glucose metabolism.

FIGS. 6E and 6F show the pH of the low and high glucose cultures at each time point. Under conditions of low glucose (FIG. 6E), the pH of the culture initially decreases as the cells utilize the glucose. However, simultaneous to the complete depletion of the glucose, the pH begins to rise. In contrast, under conditions of high glucose, the pH of the medium decreases to below pH 5 (FIG. 6F). In the experiments presented in FIG. 6, both glucose catabolism and decreasing pH occur simultaneously suggesting that either or both of these factors could be responsible for signal production by *S. typhimurium*.

Figures 7A, 7B:
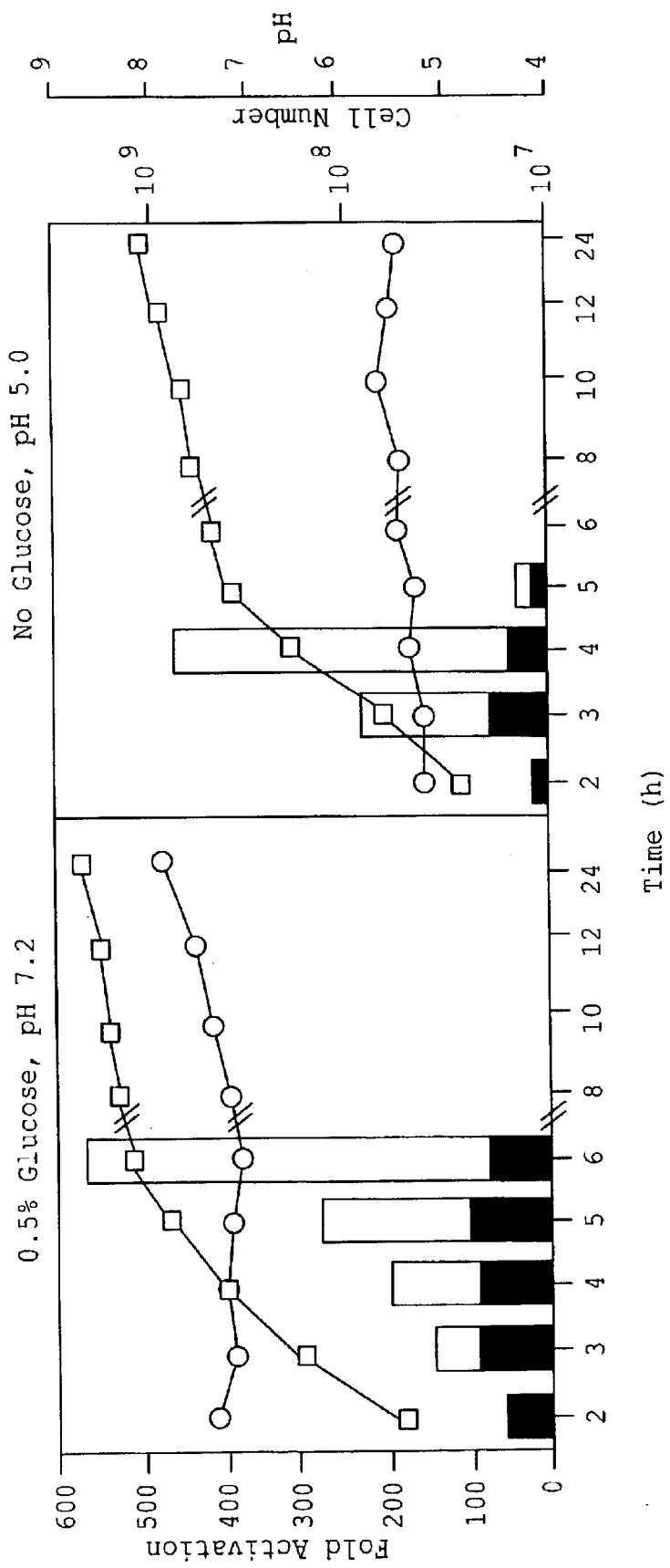
FIG. 7. Effects of glucose and pH on signal production by S. typhimurium. The quorum-sensing signal released by S. typhimurium LT2 was measured when the cells were grown in LB medium containing 0.5% glucose at pH 7.2 (FIG. 7A, bars), and when the cells were grown in LB at pH 5.0 without an added carbon source (FIG. 7B, bars). The level of signal present in cell free culture fluids (black bars) and in 0.4 M NaCl osmotic shock fluids was measured (white bars on top of black bars) at the time points indicated. In each panel, the circles represent the pH of the medium, and the squares show the cell number at the different time points.

Both Glucose Metabolism and Low pH Independently Control Signal Production in *S. typhimurium*. To distinguish between the contribution from glucose metabolism and that from low pH in signal production by *S. typhimurium*, we compared the activity produced by *S. typhimurium* grown in LB containing 0.5% glucose in a culture in which the pH was maintained at 7.2 (FIG. 7A), to that produced by *S. typhimurium* grown in LB without glucose where the pH was maintained at 5.0 (FIG. 7B). Again, we measured the signal present in cell-free culture fluids and in 0.4 M NaCl osmotic shock fluids. Similar to the data presented in FIG. 3, the level of signal observed in cell-free culture fluids was lower than that observed in the 0.4 M osmotic shock fluids.

When *S. typhimurium* was grown in LB+0.5% glucose at pH 7.2 increasing amounts of the quorum-sensing signal were detected for 6 h. At 6 h, in 0.4. M NaCl osmotic shock fluids, there was an approximately 550-fold stimulation of light production of the *V. harveyi* reporter strain BB170. No activity was produced after the 6 h time point. FIG. 7A shows that the pH was maintained between 7.15 and 7.25 for 8 h, after this time, the pH of the culture no longer decreased, but began increasing presumably because the cells had depleted the glucose. We allowed the pH to continue to increase for the duration of the experiment. Also shown in the figure is the cell number at each time point. At pH 7.2, the cells grew rapidly and reached a high cell density.

Analysis of time courses similar to those presented here, has shown that *S. typhimurium* does not produce any signal when it is grown in LB without glucose at neutral pH (see Example 1). However, *S. typhimurium* did transiently produce the quorum-sensing factor in the absence of glucose when grown at pH 5.0 (FIG. 7B). Signal was produced for 4 h, and about 450-fold stimulation of the reporter was the maximum activity achieved in 0.4 M NaCl osmotic shock fluids. Very little signal was produced by 5 h, and signal was completely absent after 6 h of incubation. FIG. 7B shows that the pH was maintained between 5.0 and 5.2 in this experiment. Note that the cells grew much more slowly at pH 5.0 than at pH 7.2.

Preliminary Characterization of the *S. typhimurium* Autoinducer Degradative Apparatus. The quorum-sensing activity produced by *S. typhimurium* LT2 is degraded by the onset of stationary phase. We have determined that the activity contained in cell-free culture supernatants and 0.4 M NaCl osmotic shock fluids from cells grown for 6 h in LB+glucose is stable for at least 24 h at 30° C., indicating that no degradative activity is present in these cell-free fluids. Furthermore, mixing cell-free culture fluids prepared from actively producing *S. typhimurium* (i.e., from cultures grown for 6 h in LB+glucose) with cell-free culture fluids prepared from *S. typhimurium* that have degraded the factor (i.e., from cultures grown for 12 or 24 h in LB+glucose) does not result in degradation of the activity. This result indicates that the degradative activity is not released, but instead, is associated with the cells.

We show in FIG. 5 that no further autoinducer is produced if *S. typhimurium* cells that are actively releasing autoinducer are shifted to 0.1 M NaCl. However, when these same cells are shifted to 0.4 M NaCl, we observe even greater autoinducer production. This result implies that low osmolarity could be a signal that induces the autoinducer degradative machinery. To begin to analyze the mechanism by which osmolarity affects autoinducer production and degradation in *S. typhimurium*, we investigated the requirement for protein synthesis in signal production and degradation by *S. typhimurium* in high and low osmolarity. As described in the legend to FIG. 5, *S. typhimurium* LT2 was grown in LB containing 0.5% glucose to achieve maximal induction of signal production then treated with 0.1M or 0.4 M NaCl in the presence and absence of protein synthesis. Cell-free fluids were prepared and tested for signaling activity. Because half of the cell-free osmotic shock fluids contained chloramphenicol (Cm), *V. harveyi* JAF305 was used as the reporter strain in the activity assay. This *V. harveyi* strain contains a $Cm^r$ cassette in the luxN gene, and its phenotype is Sensor $1^-$, Sensor $2^+$, a phenotype identical to that of *V. harveyi* BB170.

Figures 8A, 8B:
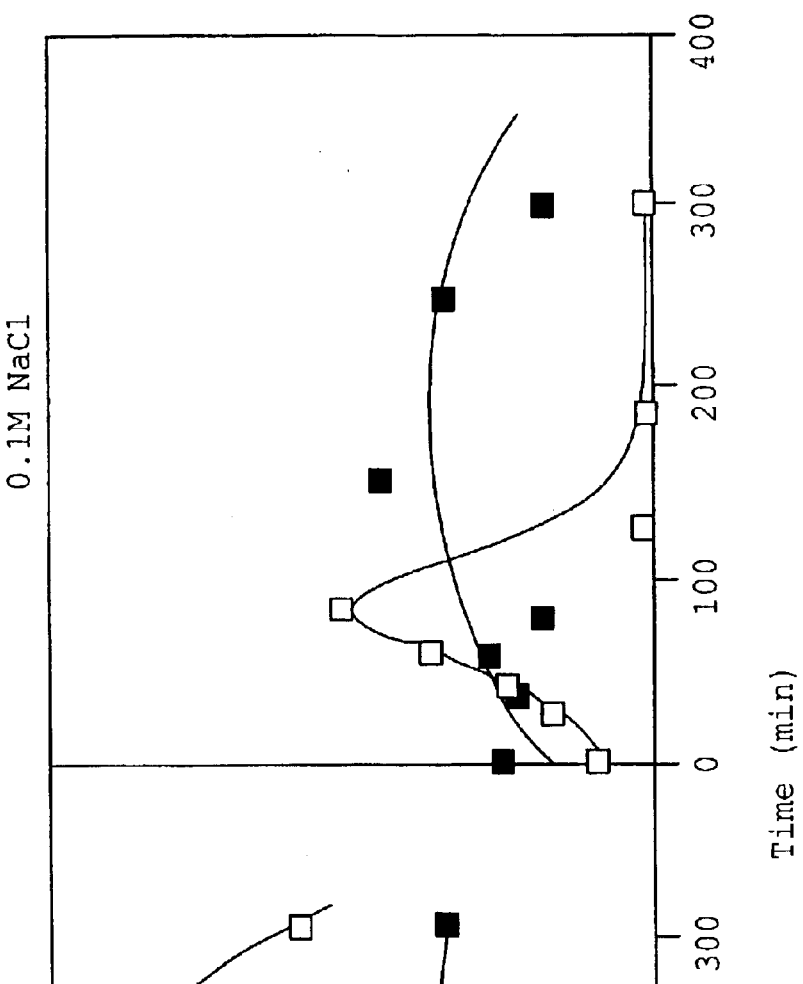
FIG. 8. High osmolarity induces signal release and low osmolarity induces signal degradation in S. typhimurium LT2. The quorum-sensing signal released by S. typhimurium LT2 resuspended in 0.4 M NaCl and in 0.1M NaCl was measured in the presence and absence of protein synthesis. S. typhimurium LT2 was pre-grown in LB containing 0.5% glucose for 6 h. The cells were harvested and resuspended in 0.4 M NaCl (FIG. 8A) or 0.1 M NaCl (FIG. 8B) in the presence or absence of 30 g/ml Cm for the time periods indicated. In each panel, the open symbols represent the activity measured in the absence of Cm and the closed symbols represent the activity measured in the presence of Cm.

When the cells were resuspended in 0.4 M NaCl, the *S. typhimurium* produced and released increasing amounts of the signal for 200 min (FIG. 8A, open squares). After this time, the level of signaling activity present in the cell-free osmotic shock fluid decreased somewhat, suggesting that some of the released signal was degraded. Quite different results were obtained when the *S. typhimurium* cells were resuspended in 0.1M NaCl (FIG. 8B, open squares). In this case, at early time points, the *S. typhimurium* produced a quantity of activity equivalent to that produced by cells resuspended in 0.4 M NaCl. However, by 120 min, no activity remained in the cell-free low osmolarity fluid. This result indicates that under conditions of low osmolarity, the released activity is rapidly degraded. We do not observe degradation of the activity in cell-free culture fluids, indicating that the disappearance of the activity from low osmolarity cell-free fluids is not due to chemical instability of the signaling molecule.

Under conditions of high osmolarity, when the cells were treated with Cm to inhibit protein synthesis, only about one quarter of the activity was produced compared to untreated cells. The closed squares in FIG. 8A show that 300-fold induction of the reporter strain occurred in the presence of Cm as compared to 1200-fold induction with the untreated cells (FIG. 8A, open squares). When the *S. typhimurium* was resuspended in low osmolarity (FIG. 8B), roughly three quarters of the activity produced in the absence of Cm (open squares) was produced in the presence of Cm (closed squares). In the presence of Cm, the released activity was not degraded by 300 min in high osmolarity and only partially degraded in low osmolarity.

To show that high osmolarity does not inhibit AI-2 signal degradation, we added the activity contained in the 0.4 M NaCl cell-free osmotic shock fluids to *S. typhimurium* cells that had been resuspended in 0.1M NaCl for two hours. As shown in FIG. 8, these are cells that can degrade the factor. Table 3 shows that these *S. typhimurium* cells degraded greater than 98% of the signaling activity while incubated at high osmolarity. The table also shows that *S. typhimurium* cells that had been incubated in 0.4 M NaCl (these are cells that are actively producing the signal) released no further activity when resuspended in the 0.1M NaCl incubation fluid obtained from the actively degrading cells. Furthermore, mixing active and inactive 0.4 M and 0.1M cell-free osmotic fluids did not result in degradation of the activity in the 0.4 M fluids.

TABLE 3

High osmolarity induces release and low osmolarity induces degradation of the *S. typhimurium* signaling factor

| Treatment | Fold-induction of Luminescence |
| --- | --- |
| 0.1 M NaCl activity[a] | 4 |
| 0.1 M NaCl activity[a] | 4 |
| 0.4 M NaCl activity[a] | 944 |
| 0.1 M cells + 0.4 M activity[b] | 17 |
| 0.4 M cells + 0.1 M activity[c] | 6 |

[a]*S. typhimurium* was grown for 6 h in LB containing 0.5% glucose. The cells were pelleted and resuspended in either 0.1 M or 0.4 M NaCl for 2 h. Cell-free fluids were prepared and tested for activity.
[b]*S. typhimurium* cells that had been incubated in 0.1 M NaCl for two hours were pelleted and resuspended in the activity contained in the cleared osmotic shock fluids obtained from cells suspended in 0.4 M NaCl for 2 h. Cell-free fluids were prepared after a 2 h incubation and assayed for signaling activity.
[c]*S. typhimurium* cells that had been suspended in 0.4 M NaCl were pelleted and incubated for 2 h in the cleared osmotic shock fluids obtained from cells suspended for 2 h in 0.1 M NaCl. Cell-free fluids were prepared after the 2 h incubation and assayed for signaling activity.

The LuxR Homolog SdiA is not Involved in Response to the AI-2 Autoinducer. A gene homologous to luxR of *V. fischeri* has been identified in *E. coli* and *S. typhimurium* and is called sdiA. Two reports suggest that in *E. coli*, SdiA modestly regulates the expression of the cell division locus ftsQAZ in response to a factor present in cell-free culture fluids (Garcia-Lara et al., 1996, supra), and in response to a few homoserine lactone autoinducers (Sitnikov et al., 1996, supra). Completion of the sequence of the *E. coli* genome shows that no LuxI homologue exists in *E. coli* so the locus responsible for the biosynthesis of the hypothesized soluble factor(s) has not been determined. Overexpression of SdiA in *S. typhimurium* has recently been shown to influence the expression of several ORFs located on the *S. typhimurium* virulence plasmid (Ahmer et al., 1998, supra). As in the *E. coli* studies, SdiA activity in *S. typhimurium* is proposed to be regulated by an extracellular factor.

It was possible that the AI-2 autoinducer that we have been characterizing in *S. typhimurium* and *E. coli* acted through SdiA. We tested whether AI-2 had an effect on genes regulated by SdiA in *E. coli* and *S. typhimurium*. In *E. coli*, we assayed an ftsQ1p2p-lacZ reporter, and in *S. typhimurium* we assayed an rck::MudJ fusion in both an sdiA+ and sdiA− background. We tested the effects of addition of LB, 0.4 M NaCl, 0.4 M NaCl osmotic shock fluids containing AI-2 activity from *S. typhimurium* LT2, *E. coli* O157, and 0.4 M NaCl osmotic shock fluid from *E. coli* DH5α. We have shown previously in Example 1 that DH5α does not produce AI-2 activity under our growth conditions.

For the *E. coli* experiments we determined that MC4100 and MC4100/pMS209 (containing ftsQ1p2p in the incorrect orientation) had no measurable-galactosidase activity. The level of -galactosidase produced by MC4100/pMS207 (containing the ftsQ1p2p-lacZ fusion) was roughly 20–30 Miller units, and this level of activity did not change under any of the conditions tested here. This level of activity of the fusion was comparable to that reported previously (Sitriikov et al., 1996, supra; Garcia-Lara et al., 1996, supra). In the *S. typhimurium* SdiA studies, similar to Ahmer et al. (1998, supra), we obtained ~30 Miller units of rck::MudJ activity in the sdiA+ background and this level was reduced to 10 units in the sdiA− background. No change in -galactosidase production occurred following the addition of AI-2 from *E. coli* or *S. typhimurium*. These results indicate that, if an extracellular factor exists that regulates the activity of SdiA, under the conditions we have tested, it is not AI-2.

Quorum Sensing in *E. coli* and *S. typhimurium*. We have developed a heterologous bio-assay that enables detection of an extracellular signaling factor produced by *S. typhimurium*. The factor mimics the action of AI-2 of the quorum-sensing bacterium *V. harveyi*, and it acts specifically through the *V. harveyi* Signaling System 2 detector LuxQ. Results using lacZ fusions to the ftsQ and rck promoters indicate that, under our assay conditions, the AI-2 quorum-sensing factor does not signal to SdiA, at least with respect to regulation of these genes. The AI-2 quorum-sensing system is therefore involved in a different *S. typhimurium* and *E. coli* signal transduction pathway than the one(s) investigated previously.

*S. typhimurium* LT2 produces an amount of activity roughly equivalent to that produced by *V. harveyi*, with approximately 800-fold stimulation of the *V. harveyi* reporter strain BB170 upon addition of 10% *S. typhimurium* cell-free culture fluids. The timing of lux induction and the shape of the response curve of *V. harveyi* to the *S. typhimurium* signal are indistinguishable from those of *V. harveyi* responding to its own AI-2. Furthermore, we have been successful at partially purifying both the *V. harveyi* AI-2 and the *S. typhimurium* signal molecule using identical purification procedures. These two results lead us to believe that the *S. typhimurium* signaling molecule is identical to or very closely related to AI-2 of *V. harveyi*.

Growth Conditions Regulate Signal Production and Degradation in *S. typhimurium*. In this example, we further characterize the regulation of the signaling activity in *S. typhimurium* LT2. Accumulation of signaling activity in *S. typhimurium* culture supernatants is maximal during mid-exponential phase when the cells are actively using glucose in rich medium. Under these growth conditions, use of glucose is accompanied by a rapid drop in pH of the culture. The results demonstrate that either glucose metabolism or low pH induces *S. typhimurium* LT2 to produce the quorum-sensing factor, indicating that both glucose and acidity generate independent signals for autoinducer production. In the presence of glucose, when the pH is not maintained, probably both the decreasing pH and the presence of an appropriate carbon source contribute to the regulation of quorum sensing in *S. typhimurium*. The results also show that production of the autoinducer ceases before stationary phase in the presence of glucose at neutral pH and in the absence of glucose at low pH. Therefore, a combination of acidic conditions and the absence of glucose is not required to cue *S. typhimurium* to terminate production of autoinducer.

In addition to glucose, growth on several other carbohydrates also induces production of the signaling activity. These include both PTS (fructose, mannose, glucitol, and glucosamine) and non-PTS (galactose and arabinose) sugars. These findings eliminate an exclusive role for the PTS in the regulation of autoinducer biosynthesis. When the *S. typhimurium* LT2 are grown on several other carbon sources (acetate, glycerol, citrate and serine) no significant accumulation of signaling activity is observed. Example 1 shows that the signal is not any of a number of substances known to be secreted by *S. typhimurium*, including the major products of mixed acid fermentation. Clearly, the cells precisely regulate production of the signaling molecule and favor its production when growing on preferred carbohydrates. Identification of the signaling molecule and cloning of the biosynthetic gene(s) will aid in a fuller understanding of the regulation process.

This example shows that, in contrast to other quorum-sensing systems, the *S. typhimurium* signal does not accumulate in stationary phase. Autoinducer production and degradation both contribute to this regulation. This example establishes autoinducer production as an increase in the signaling activity present in cell-free fluids. Activity could increase from release of newly biosynthesized autoinducer, release of stored autoinducer, repression of degradation of autoinducer, or some combination of these. We define autoinducer degradation as the disappearance of signaling activity from the cell-free fluids. This disappearance could be due to destruction of the autoinducer, re-uptake of the autoinducer, or a combination of these activities. Autoinducer production and degradation could occur simultaneously under some conditions. These findings indicate that quorum sensing in S. typhimurium is regulated such that the signal and presumably the response to the signal do not persist into stationary phase. Because signal production requires use of a preferred carbohydrate, quorum sensing in S. typhimurium may be used for measuring both the cell density and the potential of the environment for growth.

Osmolarity Influences Signal Production and Degradation in S. typhimurium. S. typhimurium cells that are actively producing signal can be further stimulated to produce signal by specific environmental treatments, such as 0.4 M NaCl osmotic shock, which indicates that several independent regulatory pathways channel information into autoinducer synthesis. On resuspension in 0.4 M NaCl, S. typhimurium cells producing autoinducer exhibit significantly greater activity when they can synthesize protein than when protein synthesis is blocked. Furthermore, degradation of the signal also requires protein synthesis.

These results have several implications. First, in the presence of Cm, S. typhimurium resuspended at both high and low osmolarity produce a similar amount of activity. This result indicates that, following growth in the presence of glucose, the S. typhimurium cells have a pre-defined capacity to produce signaling activity (and/or to release already synthesized activity from the cell). Second, resuspension of the cells in high osmolarity medium increases signal production well beyond this level, which requires protein synthesis. High osmolarity is apparently one environmental cue that induces S. typhimurium to synthesize more of the biosynthetic apparatus necessary for signal production and/or release. Third, low osmolarity causes an initial release of activity, followed by a rapid degradation that requires protein synthesis because it does occur in the presence of Cm. These results imply that the environment has changed from conditions favoring autoinducer production (LB+ a preferred carbohydrate, or high osmolarity) to conditions where autoinducer production is not favored (low osmolarity, or absence of a preferred carbon source). This environmental change induces S. typhimurium to synthesize the protein(s) required for degradation of the signaling activity.

When the S. typhimurium cells were incubated in 0.4 M NaCl no significant degradation of the activity occurred by 200 min. This result indicates that either the necessary degradative protein(s) are not synthesized under these conditions, or alternatively, the degradative apparatus is assembled, but its activity is inhibited by high osmolarity. The results show that high osmolarity does not inhibit signal degradation, because cells induced to degrade the activity can do so at high osmolarity. Therefore, the persistence of the activity in the high NaCl samples occurs because the degradation machinery is not synthesized, not because its activity is inhibited.

It is difficult to determine precisely when S. typhimurium cells produce autoinducer and when they degrade it because both processes could occur simultaneously. It appears, however, that little or no degradation occurs in high osmolarity, that conversion of cells from overall signal producers to overall signal degraders occurs in low osmolarity and that degradation requires protein synthesis. Preliminary characterization indicates that degradation is cell-associated, because the autoinducer activity is stable in cell-free culture supernatants for long periods. In addition, combining active with inactive cell-free culture fluids or active and inactive high and low osmolarity cell-free fluids does not promote degradation of the autoinducer.

The Role for Quorum Sensing in Salmonella Pathogenesis. The observations presented here on the regulation of signal production and degradation by S. typhimurium LT2 implicate a role for quorum sensing in pathogenesis of Salmonella. The conditions favoring signal production (nutrient rich, high osmolarity and low pH) are those likely to be encountered upon the first interaction of an enteric pathogen with its host. Conditions favoring degradation of the signal (nutrient poor, low osmolarity) are those most probably encountered as the pathogen exits the host. The initial colonization of the host may be a concerted effort between a population of cells coordinated through this cell-cell signaling system. Other cues, that we have not yet tested, could also regulate quorum sensing in S. typhimurium. These may represent independent or overlapping signaling pathways involved in pathogenesis. We are isolating S. typhimurium mutants to test these hypotheses. Finally, Salmonella pathogenesis is a dynamic process of interaction between the host and metabolically active bacteria. Consistent with a role for quorum sensing in pathogenesis, our evidence suggests that this quorum-sensing system is not functioning during stationary phase. We have shown that the signaling molecule is not produced during stationary phase, and furthermore, existing signal is degraded. Perhaps quorum sensing is critical for S. typhimurium to undergo the transition between a host-associated and a free-living existence.

Example 3

Quorum Sensing in Escherichia coli, Salmonella typhimurium and Vibrio harveyi: A New Family of Genes Responsible for Autoinducer Production Genes responsible for AI-2 production in V. harveyi, E. coli and S. typhimurium (named $luxS_{V.h.}$, $luxS_{E.c}$, and $luxS_{S.t.}$ respectively) are highly homologous to each other, and are thought to define a new family of proteins involved in autoinducer production. The genes have been identified in many bacteria by genome sequencing projects, but until now no function has been ascribed to them in any organism. The luxS genes do not bear homology to any other gene known to be involved in autoinducer production.

Identification and Cloning of the Gene Responsible for AI-2 Production In V. harveyi. Previous examples show that unlike many other E. coli strains, E. coli strain DH5α does not produce an AI-2 signal molecule that can be detected by V. harveyi. We reasoned therefore, that we could use E. coli DH5α as a mutant to clone the V. harveyi AI-2 production gene. A library of wild type V. harveyi BB120 genomic DNA was transformed into E. coli strain DH5α, and the transformants were screened for AI-2 production in the V. harveyi BB170 AI-2 detection bioassay. The library consisted of 2,500 clones each containing roughly 25 kb of V. harveyi genomic DNA. Five DH5α clones were identified that resulted in upwards of 300-fold stimulation of the reporter strain in the bioassay.

The recombinant cosmid DNA from the five AI-2 producing E. coli DH5α clones was analyzed by restriction analysis and Southern blotting. All five of the cosmids contained an overlapping subset of identical *V. harveyi* genomic restriction fragments, indicating that we had cloned the same locus several times. One cosmid, called pBB2929 was selected for further analysis. Random mutagenesis using transposon Tn5 was carried out on cosmid pBB2929, and pools of cosmids harboring Tn5 insertions were subsequently transformed into *E. coli* DH5α. We tested 962 individual *E. coli* DH5α/pBB2929::Tn5 strains for the loss of the ability to produce AI-2. Four *E. coli* DH5α strains harboring Tn5 insertions in pBB2929 were identified that failed to produce AI-2. We mapped the locations of these Tn5 insertions in pBB2929 and found that all four transposon insertions resided in the same 2.6 kb HindIII *V. harveyi* genomic DNA fragment (FIG. 9A).

Cosmid pBB2929 was digested with HindIII and the 8 resulting fragments were subcloned in both orientations into pALTER (Promega). The pALTER subclones were transformed into *E. coli* DH5α, and subsequently tested for AI-2 production. The only strains capable of producing AI-2 contained the 2.6 kb HindIII fragment identified in the Tn5 mutagenesis. This fragment was sequenced, and only one open reading frame (ORF) could be identified, and its location corresponded to the map positions of the four Tn5 insertions that eliminated AI-2 production. We named the ORF LuxS$_{V.h.}$ (FIG. 9A).

Mutagenesis of luxS$_{V.h.}$ in *V. harveyi*. We analyzed the effects of luxS$_{V.h.}$ null mutations on AI-2 production in *V. harveyi*. The four Tn5 insertions that mapped to the LuxS$_{V.h.}$ gene and the control Tn5 insertion adjacent to the luxS$_{V.h.}$ locus were transferred to the corresponding locations in the *V. harveyi* BB120 chromosome to make strains MM37, MM30, MM36, MM38 and MM28, respectively (FIG. 9A). Southern blotting was used to confirm the correct placement of all five Tn5 insertions in the *V. harveyi* chromosome. The four *V. harveyi* luxS$_{V.h.}$::Tn5 insertion strains were tested for the ability to produce AI-2, and all four strains gave identical results.

In FIG. 10A, we show the AI-2 production phenotypes of the wild type control Tn5 insertion strain MM28 and one representative luxS$_{V.h.}$::Tn5 insertion strain, MM30. *V. harveyi* MM28 and MM30 were grown to high cell density, after which cell-free culture fluids were prepared. The culture fluids were assayed for AI-2 activity by the ability to induce luminescence in the AI-2 detector strain BB170. FIG. 10A shows that addition of culture fluids from the control Tn5 insertion strain MM28 induced luminescence in the reporter 780-fold, while culture fluid from the luxS$_{V.h.}$::Tn5 insertion strain MM30 did not induce the expression of luminescence in the reporter. Therefore, a null mutation in luxS$_{V.h.}$ in *V. harveyi* eliminates AI-2 production.

Identification and Analysis of *S. typhimurium* Autoinducer Production Mutants. To identify the gene responsible for AI-2 production in *S. typhimurium*, we randomly mutagenized *S. typhimurium* LT2 using the MudJ transposon (Maloy et al., 1996, supra). Ten-thousand *S. typhimurium* LT2 insertion mutants were assayed for AI-2 production in the *V. harveyi* BB170 bioassay. One *S. typhimurium* MudJ insertion mutant (strain CS132) was identified that lacked detectable AI-2 in culture fluids at mid-exponential phase.

FIG. 10B shows the AI-2 production phenotypes of *S. typhimurium* strain LT2 and the corresponding MudJ insertion strain CS132. The strains were grown to mid-exponential phase in LB containing glucose, and cell-free culture fluids were prepared and assayed for AI-2. *S. typhimurium* LT2 culture fluids induced the reporter strain 500-fold, while culture fluids from strain CS132 contained no AI-2 activity. Furthermore, strain CS132 did not produce AI-2 under any of the growth conditions that we have previously reported induce AI-2 production in *S. typhimurium* (not shown).

The site of the MudJ insertion in *S. typhimurium* CS132 was determined by PCR amplification followed by sequencing of the 110 bp of chromosomal DNA adjacent to the transposon. This sequence was used to search the database for DNA homologies. The sequence matched a site (89/105 bp identity) in the *E. coli* MG1655 genome that corresponded to an open reading frame of unknown function denoted ygaG (Blattner et al., 1997, supra). In the chromosome, the *E. coli* ygaG gene is flanked by the gshA and emrB genes (FIG. 9B). The ygaG gene is transcribed from its own promoter which is located immediately upstream of the gene, indicating that it is not in an operon with gshA. The emrB gene is transcribed in the opposite direction. We PCR amplified the ygaG region from the chromosomes of *E. coli* O157:H7 and *E. coli* MG1655, and the two *E. coli* ygaG genes were cloned into pUC19.

Complementation of *S. typhimurium* and *E. coli* AI-2⁻ Mutants. We tested whether the *E. coli* O157:H7 ygaG gene and the *V. harveyi* luxS$_{V.h.}$ gene could restore AI-2 production in the AI-2⁻ strains *S. typhimurium*. CS132 and *E. coli* DH5α. In FIG. 11A, we show the AI-2 activity produced by wild type *V. harveyi* BB120, *E. coli* O157:H7 and *S. typhimurium* LT2. In this figure, the level of AI-2 activity present in *V. harveyi* BB120 cell-free culture fluids was normalized to 100%, and the activities in cell-free culture fluids from *E. coli* and *S. typhimurium* compared to that. In this experiment, *E. coli* O157:H7 produced 1.5 times and *S. typhimurium* LT2 produced 1.4 times more AI-2 activity than *V. harveyi* BB120 (i.e., 150% and 141%, respectively).

FIGS. 11B and 11C show the AI-2 complementation results for *S. typhimurium* CS132 and *E. coli* DH5α. FIG. 11B demonstrates that introduction of the *E. coli* O157:H7 ygaG gene into *S. typhimurium* CS132 restored AI-2 production beyond the level of production of wild type *S. typhimurium* (i.e., 209% activity). Comparison of the data in FIGS. 11A and 11B shows that the *E. coli* ygaG gene in *S. typhimurium* resulted in AI-2 production exceeding that produced in vivo by *E. coli* O157:H7. Introduction of the *V. harveyi* LuxS$_{V.h.}$ gene into *S. typhimurium* resulted in AM-2 production at slightly less than the level produced by wild type *V. harveyi* BB120 (i.e., 73% of the level of *V. harveyi* BB120). FIG. 11C shows that *E. coli* DH5α was also complemented to AI-2 production by both the cloned *E. coli* O157:H7 and the *V. harveyi* BB120 AI-2 production genes. However, introduction of *E. coli* O157:H7 ygaG and *V. harveyi* BB120 luxS$_{V.h.}$ into *E. coli* DH5α resulted in only 31% and 43% of the *V. harveyi* BB120 AI-2 activity, respectively. FIGS. 11B and 11C show that the control vectors produced no activity in the complementation experiments.

Analysis of the AI-2 Production Genes from *V. harveyi*, *E. coli* and *S. typhimurium*. We sequenced the AI-2 production gene LuxS$_{V.h.}$ from *V. harveyi* BB120 and the ygaG loci from *E. coli* O157:H7, *E. coli* MG1655 and *E. coli* DH5α. The translated protein sequences encoded by the ygaG ORF's are shown in FIG. 12, and they are aligned with the translated LuxS protein sequence from *V. harveyi*. The non-bold, underlined amino acids indicate the residues in the *E. coli* proteins that differ from the *V. harveyi* LuxS protein. The ygaG loci from *E. coli* encode proteins that are highly homologous to one another and also to LuxS from *V. harveyi*. The *E. coli* MG1655 (SEQ ID NO: 25) and the *E. coli* O157:H7 (SEQ ID NO: 11) YgaG proteins are 77% and 76% identical to LuxS from *V. harveyi* BB120 (SEQ ID NO: 10). The DNA sequence we determined for ygaG from *E. coli* O157:H7 differs at five sites from the reported (and our) sequence for the *E. coli* MG1655 ygaG gene. Four of the changes are silent, the fifth results in a conservative Ala to Val alteration at amino acid residue 103 in the *E. coli* O157:H7 protein.

Identification of the ygaG locus in *E. coli* MG1655 and *E. coli* O157:H7 allowed us to investigate the AI-2 production defect in *E. coli* DH5α. *E. coli* DH5α possesses the ygaG gene because we could PCR amplify this region from the chromosome using the same primers we employed to amplify it from *E. coli* MG1655 and *E. coli* O157:H7. Examination of the *E. coli* DH5α ygaG promoter showed that it is identical to that of *E. coli* MG1655, indicating that the AI-2 defect in *E. coli* DH5α is not simply due to decreased transcription of ygaG. However, sequence analysis of the *E. coli* DH5α ygaG coding region showed that a one G-C base pair deletion and a T to A transversion exist at bp 222 and 224, respectively. The frameshift mutation resulting from the G/C deletion causes premature truncation of the *E. coli* DH5α protein. FIG. 12 shows that the truncated *E. coli* DH5α protein is 111 amino acids, while the *E. coli* MG1655 and *E. coli* O157:H7 proteins are 171 residues. Twenty altered amino acids are translated after the frame shift and prior to termination of the protein. Our complementation results (FIG. 11) demonstrate that the AI-2 production defect in *E. coli* DH5α is recessive to in trans expression of ygaG, which is consistent with the defect being due to a null mutation caused by the frame shift in the *E. coli* DH5α ygaG gene.

We searched the *S. typhimurium* database using the sequence we obtained adjacent to the MudJ that inactivated the AI-2 production function in *S. typhimurium* CS132. A perfect match (110/110 bp) was identified to fragment B_TR7095.85-T7 in the *S. typhimurium* LT2 genome-sequencing database (Genome Sequencing Center, Washington University, St. Louis). However, the *S. typhimurium* LT2 database ygaG sequence (SEQ ID NO: 26) is incomplete (FIG. 12). The translated sequence matches the *E. coli* and *V. harveyi* sequences beginning at amino acid residue 8. The translated sequence shows that the *S. typhimurium* protein is 75% identical to LuxS of *V. harveyi*. In order to align the *S. typhimurium* sequence with the *V. harveyi* LuxS protein, we corrected three apparent frame shift errors in the database sequence. Considering that only crude, unannotated sequence data is currently available for *S. typhimurium*, we predict that the *S. typhimurium* protein contains seven more amino acids, and that the frame shift mutations are sequencing errors. We were unsuccessful at PCR amplifying either the *S. typhimurium* 14028 or the *S. typhimurium* LT2 ygaG gene using the primers designed for *E. coli*, so we do not yet have the complete sequence of the *S. typhimurium* gene.

The results set forth above indicate that the genes we have identified and analyzed encode a novel family of proteins responsible for autoinducer production. Members of this new family of genes, referred to herein as LuxS, are highly homologous to one another but not to any other identified genes. The encoded product of the LuxS genes catalyze an essential step in the synthesis of the signaling molecules of the present invention.

Example 4
Construction of a Sensor 1⁻, AI⁻2⁻ *V. harvevi* Reporter Strain

V. harveyi null mutants in each of the lux genes luxL, luxM, luxN, luxS and luxQ fail either to make or to respond to one specific autoinducer, but they still produce light because, in each case, one quorum-sensing system remains operational. A double luxN, luxS *V. harveyi* mutant does not emit light without the addition of exogenous AI-2 because this mutant does not respond to AI-1 and it does not produce AI-2.

The *V. harveyi* LuxS gene has been cloned into *E. coli* DH5α on a broad host range mobilizable cosmid called pLAFR2. This construction restores AI-2 production to *E. coli* DH5α. A marked null mutation was engineered into the luxS gene by introducing a chloramphenicol resistance (Cm$^r$) cassette into an internal restriction site. Placement of the Cm$^r$ cassette at this site in luxS subsequently eliminated AI-2 production in *E. coli* DH5α.

The luxS::Cm$^r$ null allele was transferred onto the chromosome of *V. harveyi* strain BB170. Strain BB170 contains a Tn5Kan$^r$ in luxN and does not respond to AI-1. To construct the double mutant, triparental conjugations were carried out by mixing stationary phase cultures of *E. coli* DH5α carrying the *V. harveyi* luxS::CM$^r$ construction in pLAFR2 (pLAFR2 carries tetracycline resistance), *E. coli* DH5α carrying the tra donor plasmid pRK2013 and the *V. harveyi* recipient strain BB170. Exchange of the luxS::Cm$^r$ mutant allele for the wild type luxS allele on the chromosome occurs by homologous recombination. The exogenote cosmid in *V. harveyi* was eliminated by the introduction of a second incompatible plasmid pPH1JI. This was accomplished by mating *E. coli* DH5α containing pPH1JI with the *V. harveyi* BB170 recipient containing the luxS::Cm$^r$ cosmid, and selecting for exconjugants on plates containing ampicillin (for counter selection of the *E. coli* donor) chloramphenicol (for inheritance of the mutant luxS::Cm$^r$ allele) and gentamicin (for maintenance of the plasmid pPH1JI). Southern blot analysis was used to verify that the exogenote pLAFR2 cosmid has been eliminated and that the luxS::Cmr construction had been transferred to the corresponding position in the genome of *V. harveyi*. The pPH1JI cosmid was subsequently eliminated by growth in the absence of gentamicin selection.

Verification that the LuxN, LuxS Double Mutant Responds to AI-2. The *V harveyi* strain that is mutant in luxN and luxS was stimulated to produce light in response to the exogenous addition of AI-2 but not AI-1. This was verified in a luminescence assay for response to *V. harveyi* AI-1 and AI-2. *V. harveyi* strain MM30 (luxS::Tn5) which is phenotypically AI-1⁺, AI-2⁻, and *V. harveyi* strain BB152 (luxM::Tn5) which is phenotypically AI-1⁻, AI-2⁺ were used as the sources of AI-1 and AI-2, respectively. The AI-2 and AI-2 present in culture fluids of these strains was tested for stimulation of light production of the *V. harveyi* LuxN, LuxS double mutant reporter strain. In this assay, autoinducer preparations from MM30, BB152 or sterile medium controls were added to the wells of microtiter plates, followed by the addition of the *V. harveyi* reporter strain. The resulting light production was monitored using a liquid scintillation counter in the chemiluminescence mode. Maximal stimulation of light production in the *V. harveyi* luxN, luxS reporter strain was compared to that produced by the Sensor 1⁺, Sensor 2⁻ *V. harveyi* strain BB886 and the Sensor 1⁻, Sensor 2⁺ *V. harveyi* strain BB170. These two *V. harveyi* strains are routinely used in this assay as reporters of AI-1 and AI-2 activity, respectively.

Determine Optimum Concentrations of AI-2 in Microtiter Assays. The aforementioned screen will be optimized for use in 96-well microtiter assays. The screen will be used in inhibitor assays for identifying inhibitors of AI-2. Purified or synthetic AI-2 will be added to the microtiter wells containing the newly constructed reporter strain and inhibition will be measured by a decrease in light emission from the wells containing an inhibitor. The assay will be optimized by determining the concentration of cells and AI-2 in the microtiter wells that will allow for maximal sensitivity. The optimal AI-2 concentration will be that which stimulates half-maximal light output for a given concentration of cells per unit time. Initial experiments will be conducted in this concentration range to determine the range of AI-2 concentration that produces the greatest change in light output. Similar experiments using AI-1 and a non self-stimulating sensor-1$^+$, sensor-2$^-$ mutant (BB886) showed that the assay was sensitive to concentrations as low as 100 nM AI-1 and that light emission was linear over 6 orders of magnitude (light emission from a self-stimulating strain was linear over 3 orders). Similar results for AI-2 using the new reporter strain that will not self-stimulate and therefore have zero background light emission are predicted. Light emission from the microtiter wells will be measured with a Wallac TriLux liquid scintillation counter model 1450-021 in the chemiluminescence mode. This machine will accommodate 16 plates and will therefore allow for 1536 separate concentration experiments per run.

Example 5

In-Vitro Method for Synthesizing AI-2; Purification and Identification of AI-2.

Several lines of evidence show that autoinducer-2 is not a acyl-homoserine lactone. Autoinducer-2 resists purification by conventional techniques used for the isolation of acyl-homoserine lactone autoinducers such as AI-1 from *V. harveyi*. Unlike other acyl-homoserine lactone autoinducers, AI-2 activity does not extract quantitatively into organic solvents. Furthermore, autoinducer-2 fails to bind to either a cation or anion exchange column. The present characterization of autoinducer-2 indicates that it has a molecular weight of less than 1000 kDa, and is a polar but apparently uncharged organic compound. The AI-2 activity is acid-stable, base-labile, and withstands heating to about 80° C. but not 100° C. The luxS genes identified bear no homology to other genes known to be involved in production of HSL autoinducers further indicating that the present AI-2 class of autoinducers is novel.

Thus, in addition to providing a cloned, overexpressed, and purified *S. typhimurium* LuxS protein, the present invention also provides a method for producing AI-2 in vitro. The present invention provides a mechanism for generating large quantities of pure AI-2 useful for mass spectral and NMR analysis, and for screening compounds that regulate the activity of AI-2. Moreover, the present invention provides a method for determining the in vivo biosynthetic pathway for AI-2 synthesis.

Figure 15:
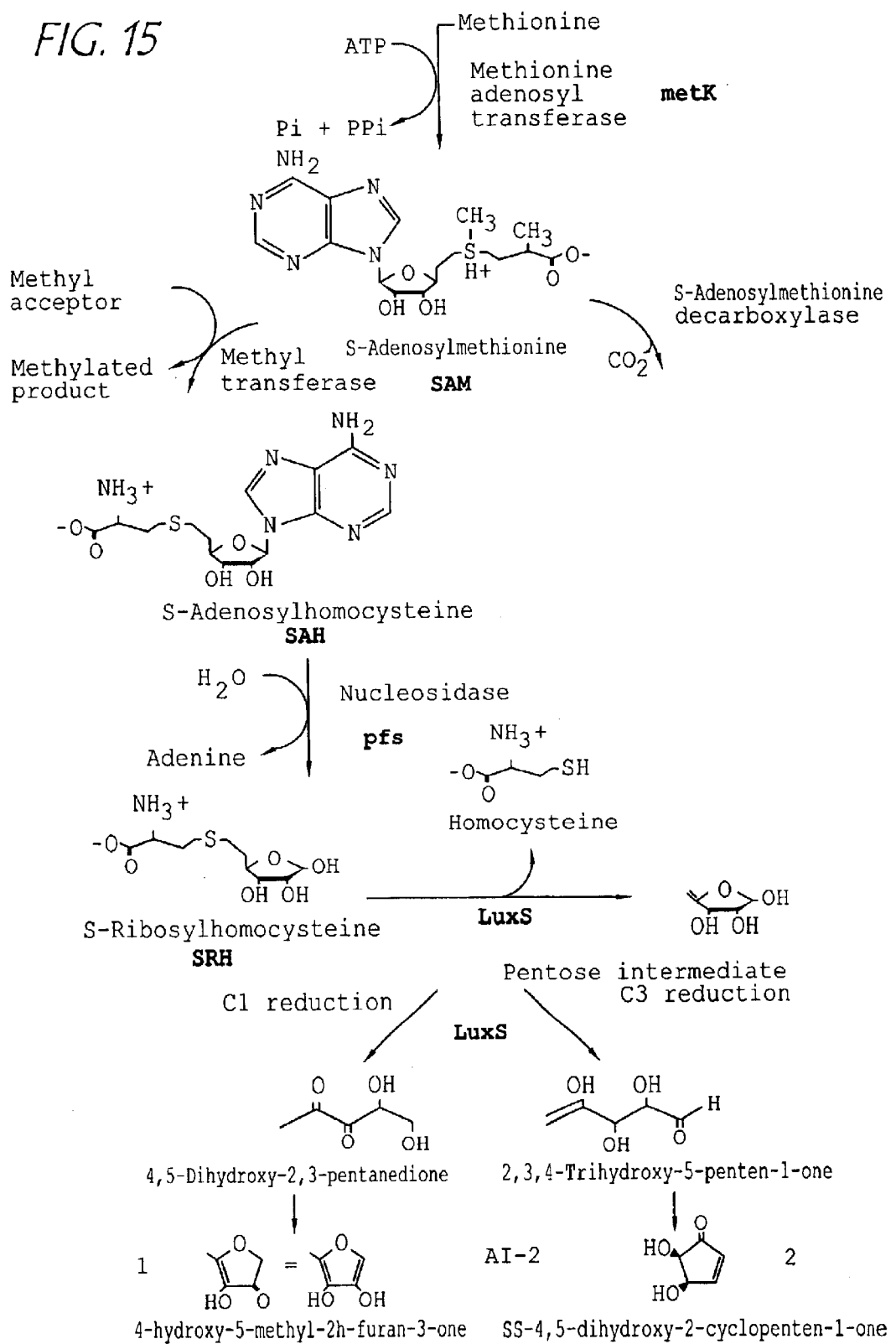
FIG. 15 shows a diagram of the biosynthetic pathway of autoinducer-2 (AI-2).
Figure 16A:
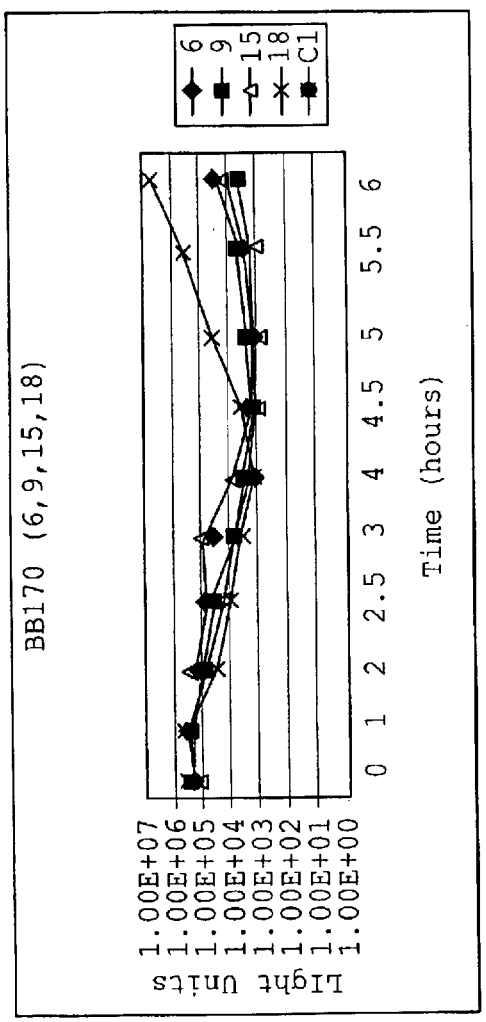
FIG. 16 shows bar graphs indicating the result of luminescence screening assays of AI-2 analogs.
Figure 16B:
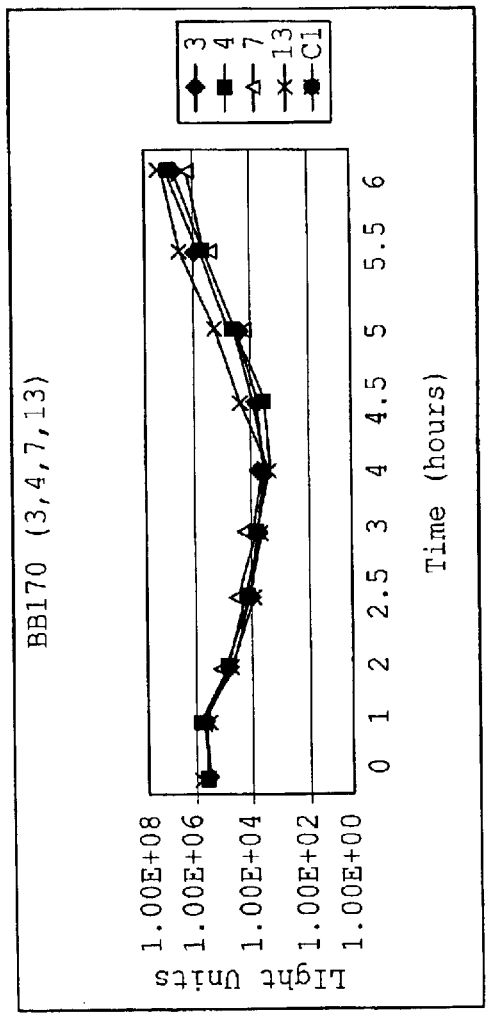
Figure 16C:
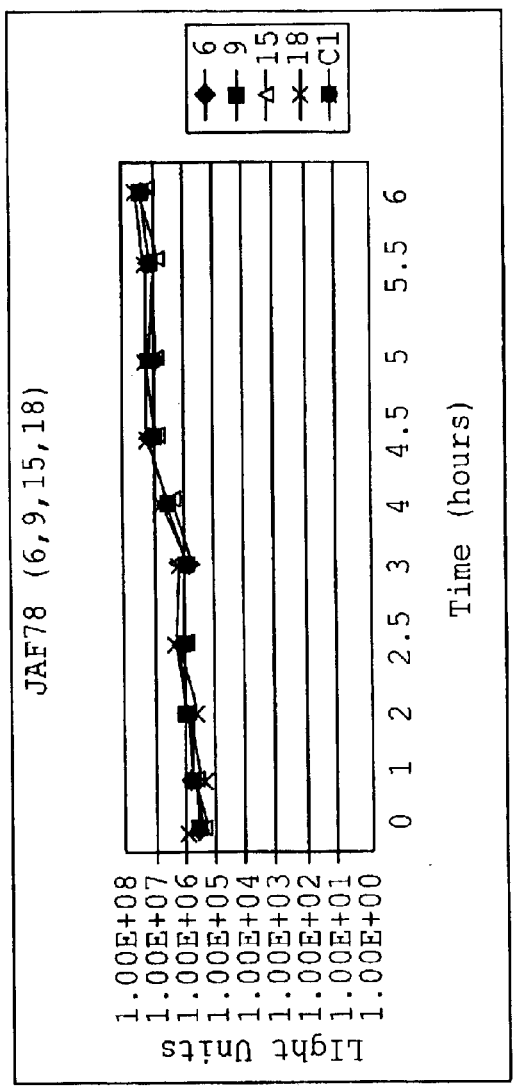
Figure 16D:
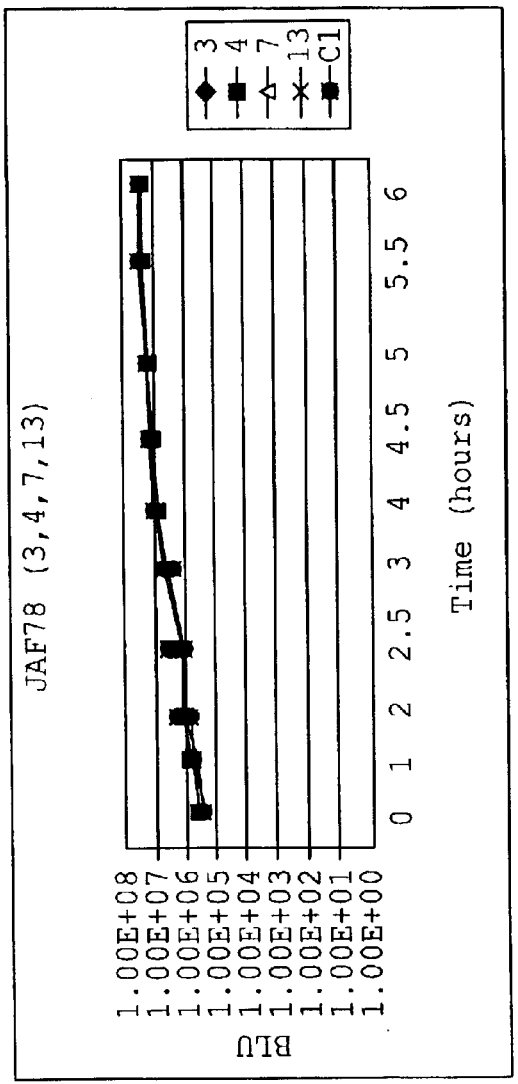

Analysis of the genomic locations of the various luxS genes identified in the present invention indicates that the luxS genes do not consistently reside in any one location in the chromosome, nor do they typically appear in close proximity to any specific gene(s). In one case, however, the luxS gene is the third gene in a three-gene operon with two genes (metK and pfs). In *E. coli*, Salmonella and many other bacteria, MetK and Pfs are involved in the conversion of S-adenosyl methionine (SAM) to homocysteine and autoinducer-2 (FIG. 15). MetK converts methionine to SAM, which is an important cofactor in one-carbon metabolism. SAM methylates DNA, RNA, and a variety of cell proteins, and several SAM dependent methyl transferases act at this step. S-adenosyl homocysteine (SAH) results from transfer of the methyl group from SAM to its substrates. SAH strongly inhibits SAM dependent methyltransferases. Therefore, bacteria rapidly degrade SAH via the enzyme Pfs. The designation "pfs" refers to an open reading frame in the *E. coli* genome that has recently been determined to encode the enzyme 5'-methylthioadenosine/S-adenosylhomocysteine nucleosidase, also known as MTA/SAH nucleosidase. In the present system, the enzyme cleaves the glycosidic bond in S-adenosylhomocycteine (SAH). Thus, Pfs converts SAH to adenine and S-ribosyl homocysteine. In a final step, S-ribosyl homocysteine undergoes cleavage to homocysteine and autoinducer-2. Homocysteine can re-enter this pathway after methylation to generate methionine, which MetK can convert to SAM.

Catabolism of SAH is a salvage pathway for recycling metabolic intermediates (adenine and homocysteine). Some bacteria, however, eliminate SAH by removing adenosine directly from SAH to generate homocysteine. Cells that use this second mechanism do not produce autoinducer-2. In the pathway shown in FIG. 15, the enzyme responsible for conversion of S-ribosyl homocysteine to 4,5-dihydroxy-2-cyclopenten-1-one or 4-hydroxy-5-methyl-2h-furan-3-one was not previously identified, cloned, or purified.

LuxS is involved in the pathway shown in FIG. 15, and SAM and SAH are involved in AI-2 production. The structure of AI-2 can be 4,5-dihydroxy-2-cyclopenten-1-one or 4-hydroxy-5-methyl-2h-furan-3-one, in which case LuxS is the uncharacterized enzyme that acts on S-ribosyl homocysteine. Second, LuxS could act on one of the intermediates to make AI-2. LuxS would represent a branch point off the known pathway.

To confirm that LuxS is involved in the conversion of SAM to AI-2, the gene encoding the *S. typhimurium* LuxS protein was cloned, overexpressed and the *S. typhimurium* LuxS protein was purified. This protein was used in combination with dialyzed cell-free extracts prepared from a *S. typhimurium* luxS null mutant to show that addition of SAM and LuxS protein could restore AI-2 production to dialyzed LuxS– cell extracts. Reaction mixtures were prepared containing 10 mM Sodium Phosphate buffer pH 7.0, dialyzed *S. typhimurium* LuxS– cell extract and SAM. Purified LuxS protein was added to some of these mixtures. The reactions were incubated at room temperature for 60 min, followed by centrifugation in a 5000 MWCO centricon. The material with MW<5000 was added to the standard *V. harveyi* bioassay as previously described. Dialyzed LuxS– cell extracts to which SAM was added or extracts containing LuxS protein without the addition of SAM produced no AI-2 activity. However, identical extracts to which LuxS protein and SAM had been added produced AI-2 that resulted in over 500-fold stimulation in light production in the bioassay.

Further investigation showed that SAM is not the direct substrate for LuxS, and that LuxS must act at a step subsequent to the conversion of SAM to SAH (FIG. 15). It was determined that AI-2 was not produced if SAM was added directly to LuxS protein, however activity was produced by pre-incubation of SAM with the LuxS– extracts, filtration, and subsequent addition of LuxS protein to the filtrate. Importantly, these studies indicate that SAM can react with an element in the cell extract before it can be used by LuxS to make AI-2. Presumably, the SAM dependent methyl transferases present in the cell extract use SAM as a methyl donor and convert it to SAH in the process. To verify this, SAH was substituted for SAM in an in vitro assay. Addition of SAH to the in vitro assay resulted in much greater AI-2 production than when SAM was added. This result indicates that LuxS functions in the pathway subsequent to the conversion of SAM to SAH. Again, addition of SAH directly to LuxS protein is not sufficient for production of AI-2 activity, while pre-incubation of SAH with dialyzed LuxS− extracts followed by filtration and subsequent addition of LuxS protein to the filtrates does result in AI-2 production. Presumably SAH is converted to S-ribosyl homocysteine and then LuxS acts to produce AI-2.

The proposed pathway shown in FIG. 15 is not a salvage pathway for recycling secondary metabolites, but rather is the pathway for production of AI-2. According to the invention, AI-2 is a derivative of ribose. It is noteworthy that, in V. harveyi, LuxP, the primary sensor for AI-2, is a homologue of the E. coli and S. typhimurium ribose binding protein.

Example 6

Bioassay for Inhibitor of the AI-1 Mediated Quorum Sensing Pathway

The quantitative assay for detection of an autoinducer-1 quorum sensing system derives from a previous report by in M. Manefield et al., Microbiol 145, 283–291(1999).

In one example of this bioassay, test compounds such as the halogenated furanones of Structure VII are dissolved in ethanol for use in the current assay.

Synthetic OHHL (N-3-(oxohexanoyl)-L-homoserine), the Al-1 autoinducer in V. fischeri, prepared according to the method of A. Eberhard et al. Arch Microbiol 146, 35–40 (1986), is dissolved in ethyl acetate for use in the assay. [3H]OHHL is prepared based on the method of H. Kaplan et al., J Label Compd Radiopharm 22, 387–395 (1985).

Bioluminescence is quantified as relative light units on a liquid scintillation counter. After addition of OHHL (10 nM to 100 nM OHHL) and the test compounds (up to 100 $\mu$M) to dilute 10 mL cultures (OD600<0.0005) the luminescence response of 100 $\mu$L samples is measured in triplicate. Appropriate concentrations of ethanol solvent are incorporated into control treatments. Growth is monitored by following the OD600 of 10 ml cultures in appropriate media from lag-, through exponential- into stationary-phase growth.

Example 7

Bioassay for Inhibitors of the Peptide-Mediated Quorum Sensing Mechanism

The assay for detection of a peptide-mediated quorum sensing system is based on a previous report described in M. Otto et al., FEBS Lett. 450, 257–262. (1999). S. epidermidis Tü3298 (DSM) is the wild-type test strain and the host for the promoter test plasmid. S. aureus strains tested for δ-toxin production are S. aureus Newman, 8325-4, SA113, ATCC 12600, RN4220, and ATCC 33591 of Otto et al. (1999). S. aureus RN6390 is a prototypic strain from which the following mutant strains are derived: S. aureus RN6911 "agr−" an isogenic mutant carrying an agr::getM mutation, "sar−" carrying a sar::Tn917LTV1 mutation, and "agr−/sar−" carrying both a sar::Tn917LTV1 and an agr::tetM mutation of A. L. Cheung et al., J. Clin. Invest. 94, 1815–1822 (1994). The promoter test plasmid inserted into S. epidermidis Tü3298 contains the promoterless pUB112 cat gene of R. Brückner et al., EMBO J. 4 2950–2300 (1985) adjacent to a multiple cloning site and carries an erythromycin-resistance gene ermB from transposon Tn551. Plasmid pRB594P3 is constructed by insertion of a BamHI-digested PCR product of the agr P3 region of S. epidermidis ATCC 14990 into the BamHI site of the multiple cloning site.

S. epidermidiscells grown in TSB or BM ('basic medium': 1% tryptone (Difco), 0.5% yeast extract (Gibco BRL), 0.5% NaCl, 0.1% K2HPO4, 0.1% glucose) are disrupted in 20 mM Tris-HCl (pH 7.8) by glass beads as described in C. Sizemore et al., Mol. Gen Genet. 227, 377–384 (1991). Cell debris is removed by centrifugation (10 min, 5000×g). Membrane fractions are prepared by additional ultracentrifugation of the crude cell extract at 10500×g for 1 h. Surface-associated proteins are isolated by boiling cells at 100° C. for 5 min and centrifugation (10 min, 5000×g). Surface proteins are isolated by incubating cells with lysostaphin for 10 min at 37° C. and centrifugation (10 min, 5000×g). Chromosomal staphylococcal DNA is prepared according to the method of J. Mamur, J. Mol. Biol. 3, 208–218 (1961). Proteins are separated by tricine-SDS-PAGE according to H. Schägger, H. Anal. Biochem. 166, 368–379 (1987) using Bio-Rad Protean IIxi chambers and a separation length of 16 cm.

Crude peptides are isolated on a Waters 600 Multi Solvent Delivery System equipped with a Lambda Max Model 481 as detector. A semi-preparative column (Nucleosil C18, 4×250 mm; 5 m; Grom, Herrenberg, Germany) is eluted at a flow rate of 3.5 ml/min with a linear gradient (10–100% B in A in 45 min; solvent A: 0.1% trifluoroacetic acid (TFA) in water; solvent B: 0.1% TFA in acetonitrile). The detection wavelength is 214 nm. The concentration of purified peptides, redissolved in dimethylsulfoxide (DMSO), is determined using analytical HPLC on a Kontron HPLC System with Kroma System 2000 software. An analytical column (Spherisorb ODS2 2×100 mm; 5 $\mu$M; Grom, Herrenberg, Germany) is eluted at a flow rate of 250 $\mu$l/min with a linear gradient (0–100% B in A in 30 min; solvent A: 0.1% TFA in water; solvent B: 0.1% TFA in acetonitrile). The detection wavelength is 214 nm. A known amount of the (unmodified) peptide DSVCASYF is used as a reference. The amount of delta-toxin is quantified using the same system. A Pharmacia Resource PHE 1 ml column is eluted with 1.5 column volumes of a linear gradient (0–100% of B in A; A: 0.1% TFA in water; B: 0.1% TFA in acetonitrile). The S. epidermidis delta-toxin is eluted using the same conditions on a AKTA explorer 100 system (Amersham Pharmacia Biotech, Freiburg, Germany). The isolated delta-toxin is chemically analyzed by ESI-MS.

CAT activity is determined according to the method of W. V. Shaw, (1975) Methods Enzymol. 43, 737–755. The assay mixture contained 100 mM Tris-HCL (pH 7.8), 0.1 mM acetyloenzyme A and 0.4 mg 5,5'-dithiobis-2-nitrobenzoic acid (DTNB/ml). Assays are performed in 96 well microtiter plates using a SpectraMax 340 microtiter plate reader (Molecular Devices, Sunnyvale, Calif. USA) with Spectra-MaxPro software. Cell extract (5 $\mu$l) and 5 mM chloramphenicol in 100% ethanol (5 $\mu$l) (or 5 $\mu$l 100% ethanol in controls) are added to 90 $\mu$l of the assay mixture. Cell extracts are diluted 1:10 or 1:100 with 20 mM Tris-HCL (pH 7.8) when necessary. Absorption at 412 nm is measured every 15 s for 20 min. The linear part of the resulting curve is used to determine the CAT activity (absorption coefficient $\epsilon$=13600/M for DTNB). For calculation of the specific activity, protein contents of the cell extracts are determined using the Bio-Rad DC protein assay for detergent-containing samples (Bio-Rad Laboratories GmbH, Munich, Germany).

SDS-polyacrylamide gels are blotted onto nitrocellulose membranes (Schleicher and Schuell BA 83) using the semi-dry blotting technique. Blots are blocked overnight with 5% skim milk. The first antibody is applied for 2 h at a concentration of 1:20,000 (anti-α-toxin) or 1:40,000 (anti-protein A). After washing, the blots are incubated with anti-IgG-coupled HRP from Amersham Pharmacia (1:5000) for 1 h. All dilutions are made in Tris-buffered saline (TBS: 10 mM Tris-HCl, pH 7.4, 150 mM NaCl). Signals are detected with the ECL detection system (Amersham Pharmacia Biotech, Freiburg, Germany).

Blood plates are prepared with sheep blood agar base (Oxoid) to which 5% defibrinated sheep blood is added. Samples are spotted onto filters, which are dried and then laid on agar plates and incubated at 37° C. for at least 24 h.

Example 8

Antibiotic Susceptibility Assay

Figure 32:
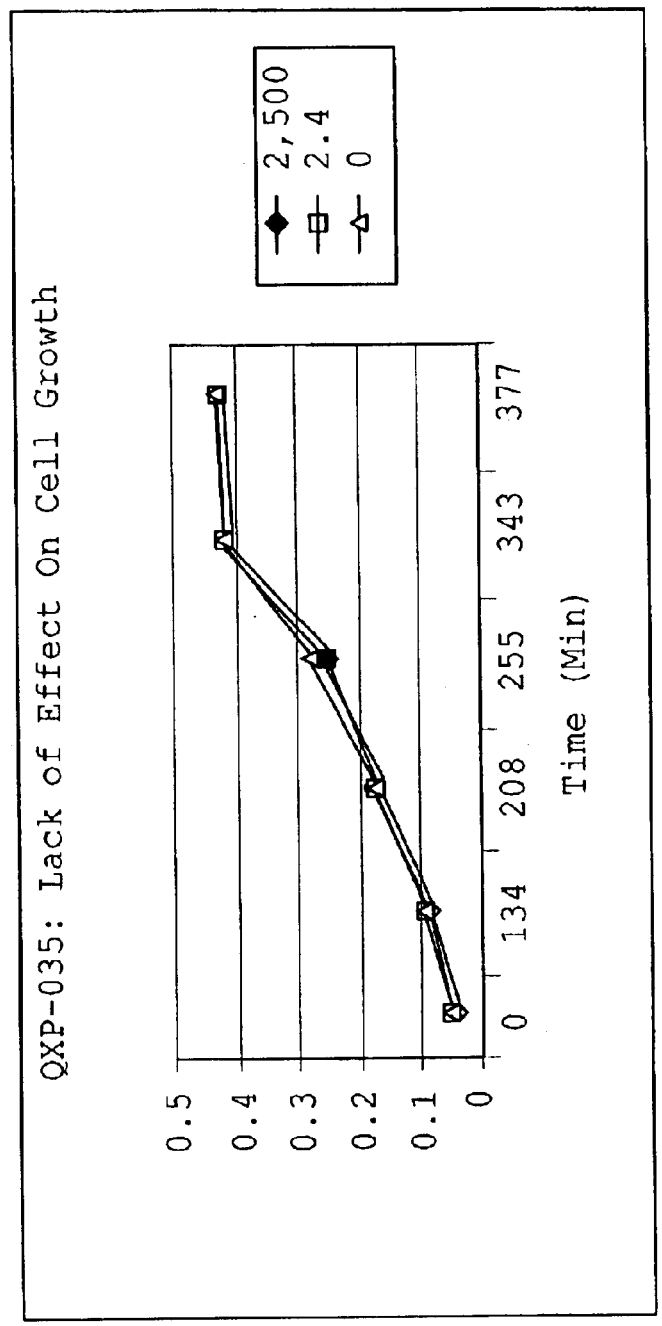
FIG. 32 shows the effect of compound QXP-035 (2-ethyl-4-hydroxy-5-methyl-3(2H)-furanone) on cell growth. *Streptococcus pyogenes* ATCC 19615 was grown in the presence of either 2.4 µg/ml or 2.5 mg/ml of compound QXP-035. Cell growth was monitored by taking periodic measurements of absorbance at 600 nm.

Antimicrobial susceptibility testing was conducted according to the National Committee for Clinical Laboratory Standards (NCCLS) reference method "Broth Dilution Procedure (Microdilution)" published January 1977 (UPDATE VERSION). The method yields a minimum inhibitory dose (MC) required for complete inhibition of bacterial growth. MICs were determined using a dilution series of antibiotic, in which all of the wells contained a constant concentration of the inhibitor compound was maintained. In addition, before the instant susceptibility tests were performed, the inhibitor compounds were tested in the appropriate inhibitor screens (See, for example, FIG. 32 for the AI-2 inhibitor 2-ethyl-4-hydroxy-5-methyl-3(2H)-furanone). Once their inhibitory activity is demonstrated in screens, the inhibitors were also tested for antibiotic activity. Experiments were conducted in 96 well microtiter plates using a final volume of 0.1 ml/well. Assays were conducted using either Mueller-Hinton broth, Todd-Hewitt broth, or Nutrient Broth (Difco). The bacterial innoculum was prepared from a log phase overnight culture of *Streptococcus pyogenes* ATCC 19615 or *Staphylococcus aureus* ATCC 25923. Turbidity of the cultures was adjusted with saline to 0.05 McFarland standard ($10^7$ CFU/ml), and 5 microliters of this innoculum was added to each well. The inhibitor compounds were prepared by dissolving a stock solution in water. Working stocks of quorum inhibitors compounds were made by diluting the stock solutions with bacterial broth. Sodium salts of the antibiotics were used in these experiments. A stock solution (10 mg/ml) was prepared as stipulated by the manufacturer by dissolving a weighed amount of antibiotic in water or DMSO. All antibiotics were added in two-fold serial dilutions to a series of wells to yield final concentrations ranging from 100 µg/ml to 0.1 µg/ml. The single exception was sulfisoxazole where the range of final doses ranged from 300 µg/ml to 2.5 µg/ml. Bacterial broth was used as the diluent. The range of antibiotic concentrations used were chosen to be at and below the MIC for the antibiotic alone. Cultures were sealed and incubated for 20 hours at 37° C. MIC values were determined by spectrophotometric measurements of absorbance at 600 nm. The MNC is defined as the lowest concentration of antibiotic that completely inhibits growth of 99% the test organism in the tubes. Fold-changes in MIC concentration were determined by comparing the MIC for antibiotic and quorum inhibitor compounds with the MIC measured using antibiotic alone.

Figure 33A:
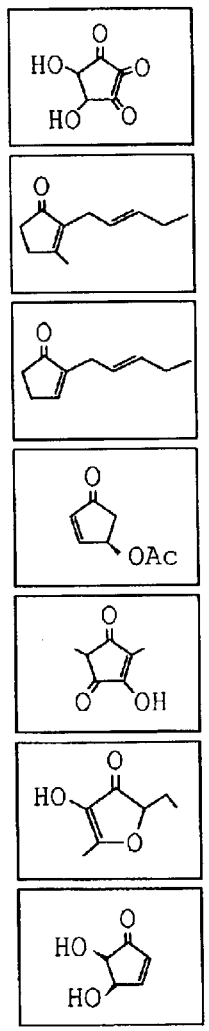
FIG. 33 are examples of inhibitory (Column A) and stimulatory (Columns B and C) compounds for the AI-2 receptor.
Figure 33B:
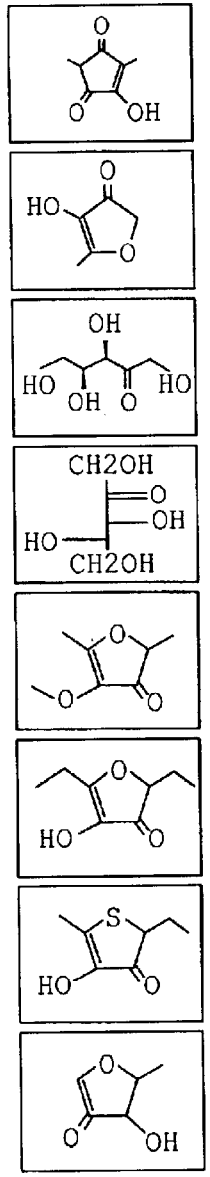
Figure 33C:
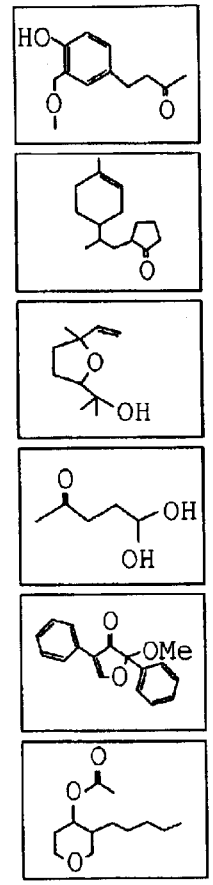
Figure 34:
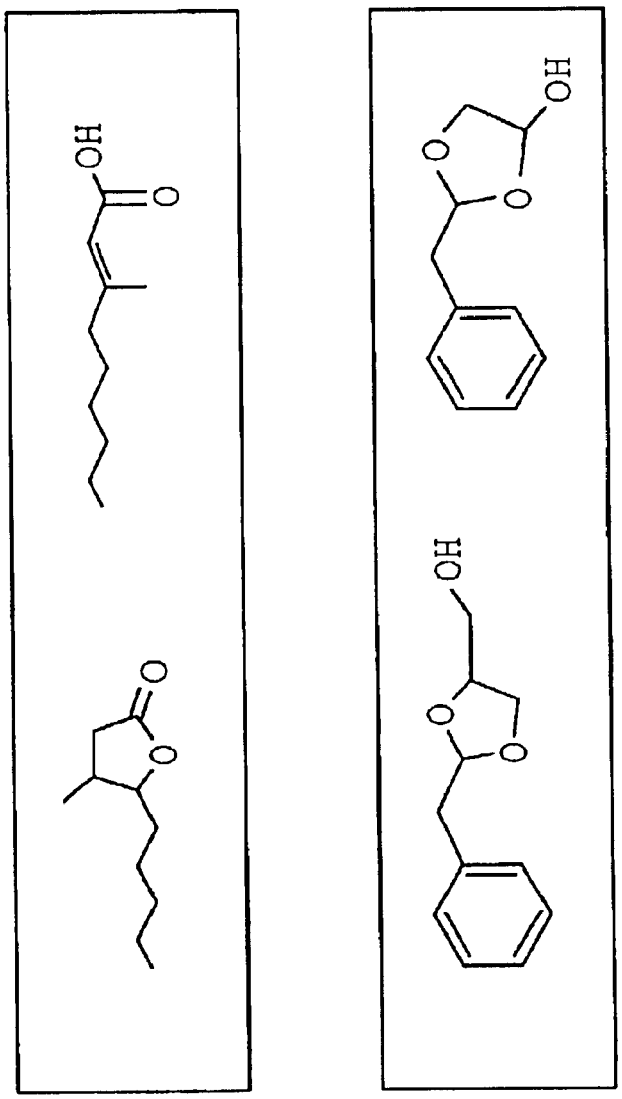
FIG. 34 are examples of stimulatory compounds for the AI-2 receptor.

Using the above antimicrobial assay, the combination of the quorum inhibitor compound 2-ethyl-4-hydroxy-5-methyl-3(2H)furanone in combination with either vancomycin, ciprofloxacin or sulfisoxazole showed marked synergies against the test strain. The quorum inhibitor compound did not inhibit cell growth (FIG. 33). Vancomycin alone had an Minimum Inhibitory Concentration (MIC) of approximately 100 µg/ml; when it was combined with the inhibitor compound at a concentration of 5 µg/ml it had approximately the same MIC, when it was combined with the quorum inhibitor compound at 12.5 µg/ml it had an MIC of approximately 1.6 micrograms/milliliter. Vancomycin had the same MIC when the concentration of the quorum inhibitor compound was increased to 50 µg/ml. Finally, with the inhibitor alone, the MIC was greater than 100 µg/ml. Against the same test strain, ciprofloxacin alone has a MIC of 0.8 µg/ml. In combination with the same quorum inhibitor molecule at a concentration of 25 µg/ml, ciprofloxacin displayed a MIC of 0.4 µg/ml. Again, when the inhibitor was tested alone the MIC was greater than 100 µg/ml. Against the same test strain sulfisoxazole alone exhibited an MIC of approximately 300 micrograms per milliliter, while in the presence of a concentration of 100 micrograms per milliliter of the quorum inhibitor compound it exhibited a MIC of approximately 100 µg/ml. As before, the inhibitor compound alone demonstrated and MIC of greater than 100 micrograms per milliliter. Against the other test strain, *Staphlylococcus aureus*, ampicillin alone had a MIC of 1.6 µg/ml, while in the presence of the inhibitor compound (25 µg/ml) the antibiotic had a MIC of 0.4 µg/ml.

Example 9

Isolation of Halogenated Furanones

Many of the halogenated furanones of Structure VII are extracted from their host bacteria according to protocols established by R. de Nys, Tetrahedron 49, 11213–11220 (1993). Algal tissue is frozen, freeze-dried, extracted with dichloromethane and reduced in vacuo. Pure compounds are isolated from this crude extract by vacuum liquid chromatography and HPLC, and identified by 1H and 13C NMR spectroscopy.

Example 10

Preparation of Inhibitors of the Peptide Quorum-Sensing Mechanism

Cyclic peptides of the formula (cyclo)-YSTCDFIM; (cyclo)-GVNACSSLF; (cyclo)-GVNASSSLF; and (cyclo)-GVNA(DAPA)SSLF, in which the C-terminal carbonyl group forms a thiolactone with the sulfur atom of the cysteine residue (YSTCDFIM and GVNACSSLF); a lactone group with the oxygen atom of the first serine residue (GVNASSSLF); or an amide bond with amino group of the diaminoproprionic acid (DAPA) residue (GVNA(DAPA) SSLF; are synthesized through use of the Fmoc/tBu strategy on Tritylresin (PepChem: Clausen and Goldammer, Tübingen, Germany). The sequence of the peptide is DSVXASYF, with cysteine (C), serine (S) or 1,3-diaminopropionic acid (Dpr) in the X position. The corresponding protected amino acids for the synthesis of cyclic peptides are Fmoc-Cys(Mmt)-OH, Fmoc-Ser(Trt)-OH (both cleavable with TFA:TIS in dichloromethane) and Fmoc-Dpr (Dde)-OH (cleavable with hydrazine). The cyclic peptides are synthesized and purified according to M Otto, et al. (1998) FEBS Lett. 424, 89–94. The purity of peptides (>90%) is controlled by RP-C18 chromatography and ESI-MS.

Example 11

Characterization and Biosynthesis of an AI-2 Analog

The invention further provides a method for an in vitro procedure for large-scale production of pure AI-2. As indicated in FIG. 15, SAH is a precursor in the LuxS dependent biosynthesis of AI-2. Furthermore, LuxS does not act directly on SAH. Prior to the action of LuxS, some enzyme in dialyzed cell extracts must first act on SAH to convert it to S-ribosyl homocysteine by Pfs. Therefore the substrate for LuxS is S-ribosyl homocysteine.

To confirm that LuxS acts on S-ribosyl homocysteine, the Pfs enzyme can be purified and used to convert SAH to S-ribosyl homocysteine. Toward this end, the pfs gene has been cloned from *S. typhimurium* 14028 placed into the overexpression vector pLM-1. The Pfs enzyme will be overexpressed and SAH will be added to purified Pfs to produce S-ribosyl homocysteine. The conversion of SAH to S-ribosyl homocysteine will be confirmed by reverse phase HPLC analysis (SAH is UV active while S-ribosyl homocysteine is not). Subsequently, the S-ribosyl homocysteine produced by Pfs will be added to purified LuxS. Following incubation, the mixture will be filtered over a 5000 MWCO centricon. The filtrate will be tested for AI-2 activity in the previously described *V. harveyi* bioassay.

Regulation of LuxP or LuxQ Activity

It is an object of the invention to provide compounds and methods for regulating the activity of autoinducer-2 receptors such as LuxP or LuxQ. Compounds of the invention include those that interact with LuxP or LuxQ. Specifically, the invention provides a method for the regulation of LuxP or LuxQ protein resulting in the regulation of bacterial cell growth or the regulation of bacterial pathogenicity by regulating the expression of a factor associated with bacterial virulence. The method of the invention envisions contacting LuxP or LuxQ with pentenomycin, or derivatives thereof, such that LuxP or LuxQ activity is regulated. Pentenomycin has previously been identified as having antibiotic activity. The present study provides the first data indicating that pentenomycin acts as an inhibitor of AI-2 initiated activation of a biochemical pathway. The chemical structure of pentenomycin, and derivatives thereof (see below), is/are similar to that of the structure of autoinducer-2 as identified in the present study.

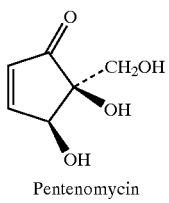
Pentenomycin

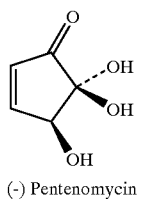
(-) Pentenomycin

The present invention provides a basis for the rational design of derivatives and analogs of AI-2 for regulating bacterial growth and pathogenicity. Such analogs and derivatives can be used to regulate the activity of those proteins involved in the autoinducer-2 signaling pathway, such as LuxP or LuxQ.

An autoinducer-2 (AI-2) molecule of the invention can interact with LuxP, the protein encoded by the homologue of the luxP gene of pathogenic bacteria such as *V. cholerae, S. typhimurium* and *E. coli*. In turn, the AI-2-LuxP complex can interact with LuxQ, which is the protein product encoded by the luxQ gene. The AI-2-LuxP-LuxQ interaction can promote luminescence in bacteria such as Vibrio spp by activating the expression of genes involved in luminesence. In addition, the AI-2-LuxP-LuxQ interaction has been linked to the activation of biochemical pathways required for bacterial pathogenicity. Thus, the invention provides a method for controlling bacterial gene expression and for regulating bacterial pathogenicity by regulating AI-2-LuxP-LuxQ interactions using an AI-2 analogue, such as pentenomycin. For example, an AI-2 analogue can compete with endogenous AI-2 for binding to LuxP or LuxQ proteins thereby providing a means for regulating the activity of the protein.

Figure 17:
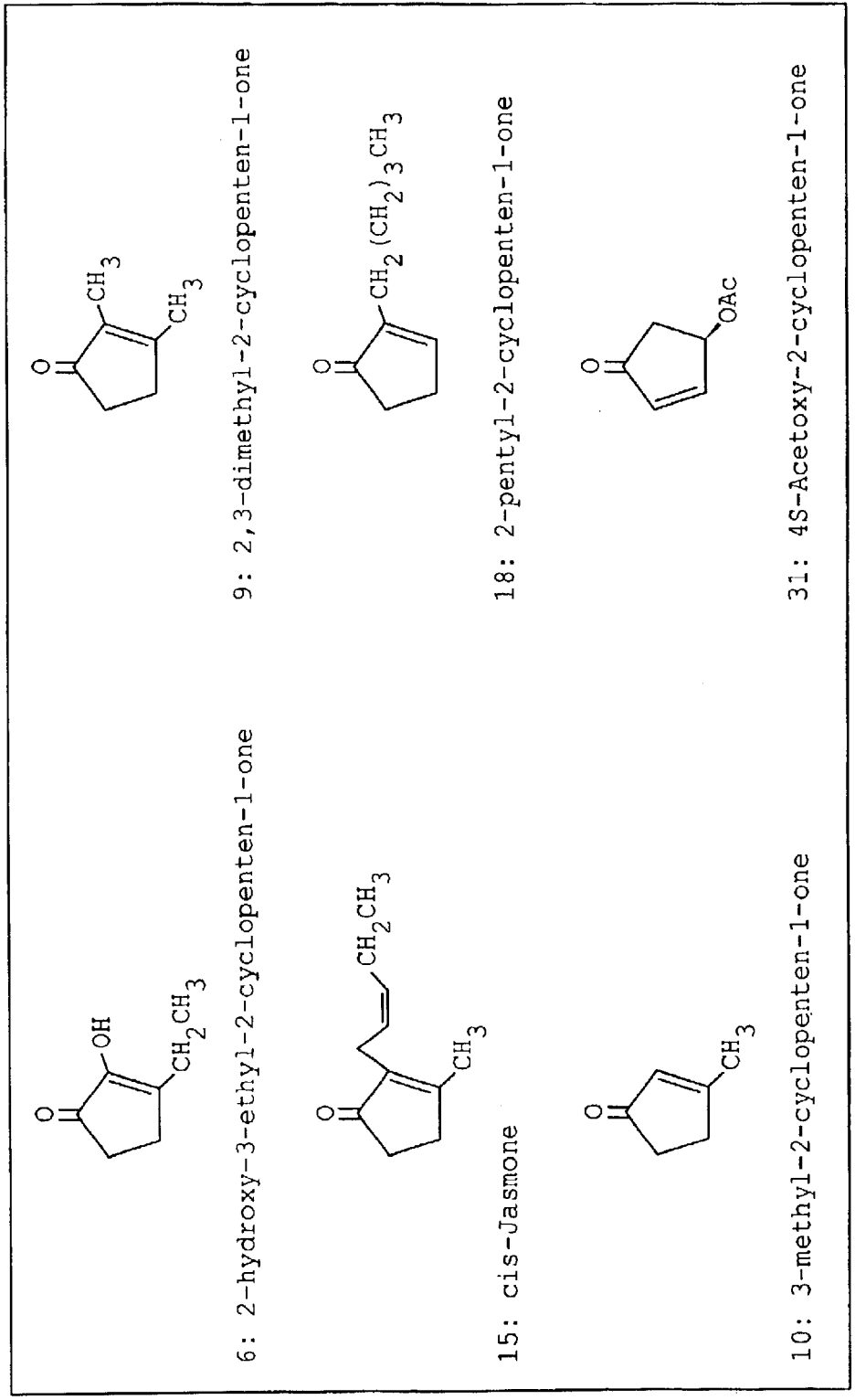
FIG. 17 shows examples of structures of analog compounds that inhibit the activity of AI-2 in the *V. harveyi* luminescence assay. The structures of these compounds indicate that the C2 and C3 positions are important to the inhibitory activity of the compounds.
Figure 18:
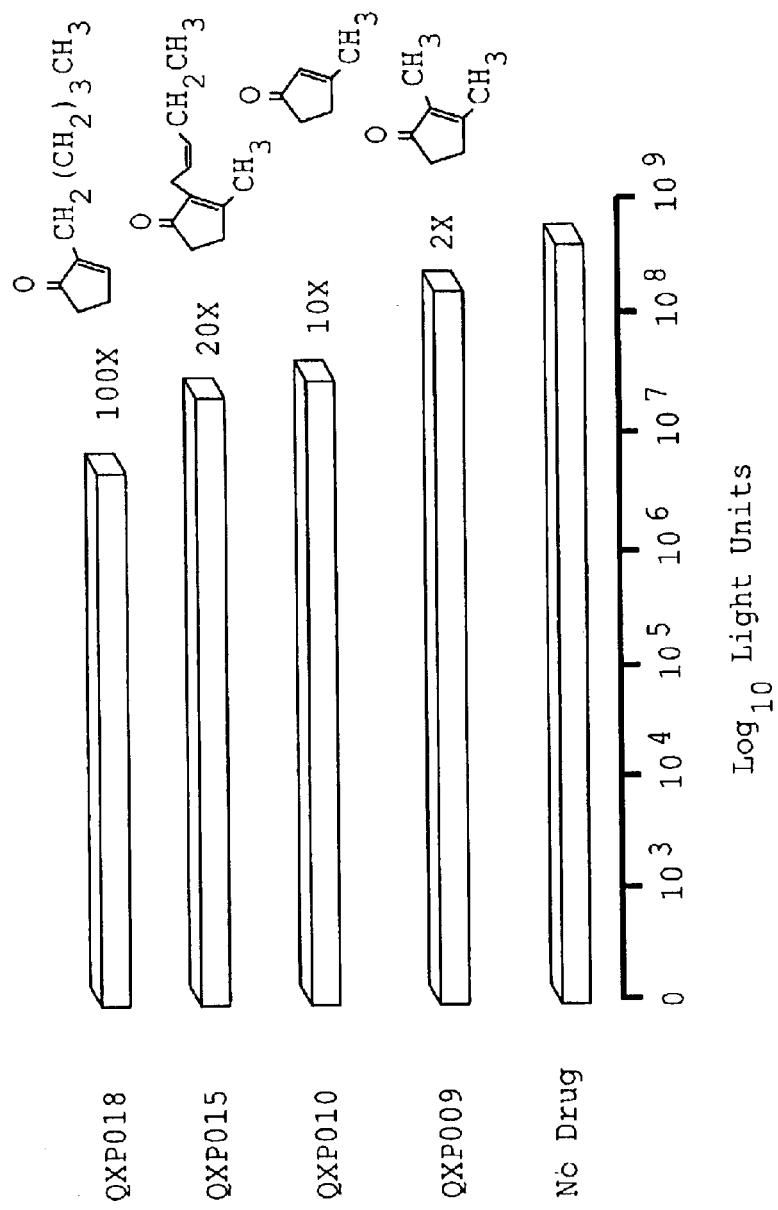
FIG. 18 is a bar graph showing the effect of compounds QXP009, QXP010, QXP015 and QXP018 on AI-2 activity in the *V. harveyi* luminescence assay.

The present invention further provides examples of AI-2 analogs capable of inhibiting AI-2 activated luninescence in the *V. harveyi* luninescence assay (see FIGS. 16–18). These AI-2 analogs have not previously been shown to have antimicrobial activity or act as an inhibitor of AI-2 initiated activation of a biochemical pathway. Examples of such analogs include:

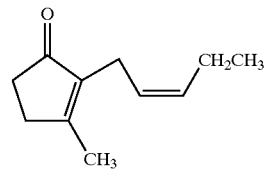
Cis-Jasmine

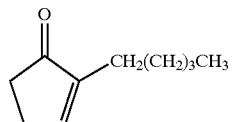
2-pentyl-2-cyclopenten-1-one

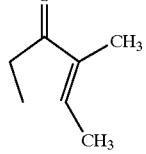
2,3-dimethyl-2-cyclopenten-1-one

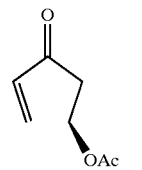
4S-Acetoxy-2-cyclopenten-1-one

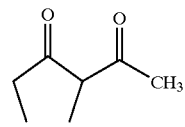
2-acetylcyclopentanone

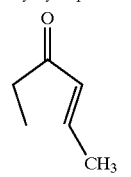
3-methyl-2-cyclopenten-1-one

FIG. 16 shows the results of screening assays of AI-2 analogues. FIG. 16 panels A and B show the results of a 6 hour assay using compounds 6, 9, 15 and 18 (panel A) and compounds 3, 4, 7 and 13 (panel B) on test strain BB170. FIG. 16 panels C and D show the effect of the same compounds on control strain JAF78. Strain BB170 synthesizes AI-2 starting at 4.5 hours into the assay. Light produced at the start of the assays is from AI-2 carried over from cells diluted from stationary phase. Strain JAF78 is a mutant strain in which light production is "locked on" and is unaffected by the presence or absence of autoinducer. Increase in light over the time course reflects increase in cell population density. Compounds 6,9,15 and 18 produced approximately a 100-fold decrease in light emission from the no-compound control at the 6 hour time point in BB170 but no significant change in light emission in JAF78 (panels A&C). Direct counts of cells plated from each treatment showed no significant differences in cell viability. Compounds 3,4,7 and 13 produced no significant difference in light emission in either strain (panels B&D).

LuxO Regulation of Expression. At low cell density, in the absence of autoinducer-2, the LuxQ sensor acts as a kinase. The sensor autophosphorylates conserved His residues and transfers the phosphoryl group to conserved Asp residues in attached response regulator domains. Thus, the first phosphotransfer event is intra-molecular. Subsequently, inter-molecular phospho-transfer occurs from the LuxQ sensor to a conserved His residue of the phosphorelay protein LuxU. In the final step, the phosphoryl group is transferred to the conserved Asp in the response regulator protein LuxO. Phosphorylation of LuxO activates the protein, and its function is to cause repression of the luxCDABEGH operon. Therefore, at low cell density, the bacteria make no light. At high cell density, in the presence of autoinducer-2, LuxQ activity is altered, switching from kinase to phosphatase activity. In this mode, the sensor drains phosphate out of the system. The phosphatase activity of the sensor results in rapid elimination of LuxO-phosphate, and the dephosphorylated form of LuxO is inactive. Therefore, at high cell density, no repression of luxCDABEGH occurs, and the bacteria emit light.

*V. harveyi* uses this complex quorum sensing system, specifically the LuxPQ/AI-2 quorum sensing circuit, to communicate between species. Therefore, *V. harveyi* monitors not only its own cell-population density but also that of other bacteria. This ability allows *V. harveyi* to regulate behavior based on whether it exists alone or in consortium. luxS, the gene encoding the AI-2 synthase, belongs to a highly conserved family of genes that specify AI-2 production in a wide range of both Gram-negative and Gram-positive bacteria, including *E. coli, S. typhimurium, Salmonella typhi, Vibrio cholerae, Yersinia pestis, Staphylococcus aureus, Streptococcus pyogenes, Enterococcus faecalis*, and *Bacillus subtilis*. Thus, various species of bacteria can use AI-2 for inter-species communication. Moreover, the present study indicates that the presence of AI-2 initiates a cascade of events culminating in the derepression (i.e., activation) of various genes. It is an object of the invention to provide compounds and methods for regulating AI-2 activity such that the derepression/activation of downstream genetic elements is also regulated. To that end, the present study indicates that LuxO activates transcription of downstream target genes including the production of siderophore, as well as colony morphology (Table 4 and FIG. 20). These are the first examples of quorum sensing regulated phenotypes, other than Lux, in *V. harveyi* clearly indicating that AI-2 quorum sensing controls potentially pathogenic phenotypes.

In the present study, mutations in luxO (the gene encoding the LuxO protein) and/or rpoN (the gene encoding the $\sigma^{54}$ protein) were tested to determine if they affected siderophore production in *V. harveyi*. The Schwyn and Neilands chromazurol S assay was used to measure siderophore released by different *V. harveyi* strains. The S assay quantitatively measures siderophore by optically assessing the color change that chromazurol S undergoes when it loses its chelated ferric ion to siderophore present in spent culture fluids. Regulation of siderophore production in many species of bacteria including *E. coli* and *V. cholerae* is under the control of the ferric uptake regulation (Fur) protein. In these cases, under iron-rich conditions, the Fur protein binds Fe(II) ions and represses the transcription of genes required for siderophore biosynthesis and transport. De-repression of these genes occurs during periods of iron deprivation, when Fur is not bound to Fe(II) The results presented in Table 4 indicate that LuxO and $\sigma^{54}$ have a role in activating the production of siderophores.

TABLE 4

LuxO and $\sigma^{54}$ regulate siderophore production in *V. harveyi*

| V. harveyi strain | Genotype | $P_{lac}$-rpoN[a] | Siderophore units[b] |
|---|---|---|---|
| BB120 | wild type | − | 8 ± 3 |
| JAF78 | luxO:: Cm$^r$ | − | 7 ± 4 |
| JAF548 | luxO D47E | − | 50 ± 5 |
| BNL240 | rpoN::Cm$^r$ | − | 3 ± 3 |
| BNL240 | rpoN::Cm$^r$ | + | 6 ± 3 |
| BNL244 | luxO D47E, rpoN::Cm$^r$ | − | 4 ± 1 |
| BNL244 | luxO D47E, rpoN::Cm$^r$ | + | 25 ± 3 |

[a]The wild type *V. harveyi* rpoN gene was expressed under control of the lac promoter from plasmid pBNL2090 (Table 4).
[b]Siderophore production was measured using the chromazurol S assay (Schwyn and Neilands, 1987). Siderophore units were calculated according to the method of Payne (1994), and normalized for cell number using the formula: 100 × [(OD$_{630}$ (media control) − OD$_{630}$ (spent culture fluid))/OD$_{600}$ (cell culture)]. Values shown are the mean ± SEM of three independent experiments.

Wild type strain BB120, the −luxO strain JAF78, and the rpoN::Cm$^r$ null strain BNL240 all produce similar amounts of siderophore (3 to 8 units) when grown in AB minimal medium. In contrast, the presence of activated luxO D47E in JAF548 increases siderophore production to 50 units. This result indicates that phospho-LuxO activates siderophore production. Disruption of rpoN in the luxO D47E background (strain BNL244) reduces siderophore production to wild type levels (4 units), indicating that similar to what was shown above for Lux regulation, phospho-LuxO controls siderophore production when wild type $\sigma^{54}$ is present. In trans introduction of wild type rpoN into the luxO D47E, rpoN::Cm$^r$ strain complements the defect. In this case, siderophore production increased to 25 units, approaching that of the luxO D47E strain. These results demonstrate that the activated form of LuxO, along with $\sigma^{54}$, has a role in regulation of siderophore production.

In addition to the siderophore production phenotype, the present study shows that *V. harveyi* mutants possessing a constitutively activated LuxO (i.e., LuxO D47E or LuxN L166R) also consistently exhibit an altered colony morphology that is similar to the rugose colony morphology described for *V. cholerae* and the opaque colony morphology described for *Vibrio parahaemolyticus*. In *V. cholerae*, the rugose phenotype requires a large gene cluster called vps that is necessary for the production of the exopolysaccharide rugose polysaccharide. In *V. parahaemolyticus* a homologue of the *V. harveyi* LuxR transcriptional activator protein called OpaR is involved in the switch to the opaque phenotype. *Vibrio cholerae i*s the causal organism of the diarrheal disease cholera and the rugose variants of *V. cholerae* have been shown to produce an exopolysaccharide matrix. The rugose polysaccharide has been shown to confer increased resistance to a variety of agents such as chlorine, bioacids, and oxidative and osmotic stresses. In addition, the rugose phenotype promotes biofilm formation thereby increasing the survival of the organism in aquatic environments.

Figure 20:
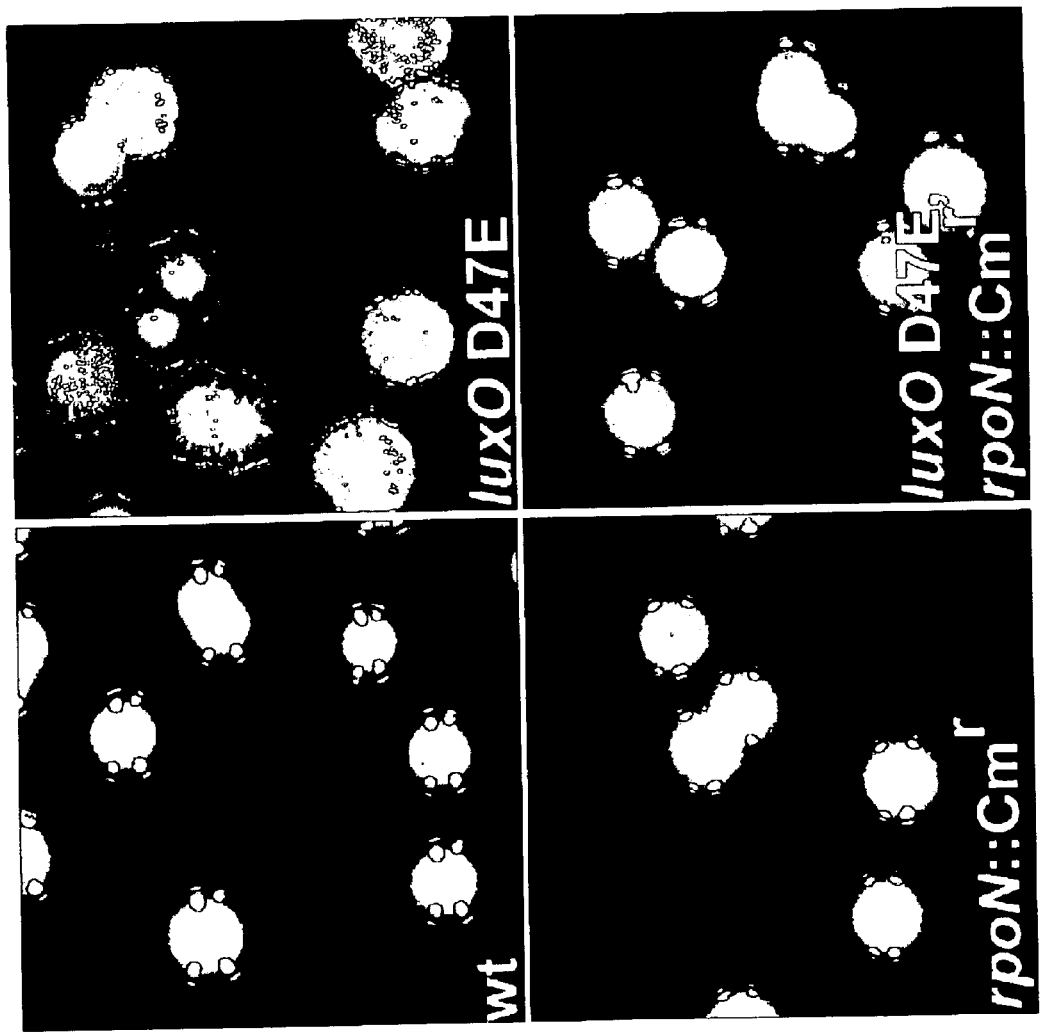
FIG. 20 is a photograph showing σ⁵⁴ and LuxO regulation of colony morphology in *V. harveyi*. The smooth and rugose colony morphologies of different *V. harveyi* strains are shown in the photographs. Each *V. harveyi* strain was grown in LM broth overnight at 30° C. The strains were streaked onto LM plates, grown for 24 hr at 30° C. and photographed. The strain denotations are the following: wt, BB120; luxO D47E, JAF548; rpoN::Cmr, BNL240; and luxO D47E, rpoN::Cmr, BNL244. Both BNL240 and BNL244 were supplemented with 1 mM L-glutamine in broth and on plates.

FIG. 20 is a photograph showing the colony morphologies of various *V. harveyi* strains. Colonies of wild type *V. harveyi* and the rpoN::Cm$^r$ null strain are smooth and glassy in appearance, while colonies of the luxO D47E strain are wrinkled and opaque. The figure shows that the colony morphology phenotype caused by the activated luxO D47E protein is dependent upon the presence of wild type rpoN because strain BNL244 (luxO D47E, rpoN::Cm$^r$) has the wild type smooth colony morphology. Similar to that observed for rugose strains of *V. cholerae*, the *V. harveyi* luxO D47E mutant forms a pellicle when grown in liquid culture. Pellicle formation is also dependent on wild type rpoN. Identical results were obtained when the "locked" LuxN L166R strain JAF549 was used in place of the LuxO D47E strain JAF548. The fact that a single amino acid change in LuxO or LuxN can affect various phenotypes including siderophore production and colony morphology indicates that LuxO and $\sigma^{54}$ are involved in the regulation of multiple target genes.

Figure 21:
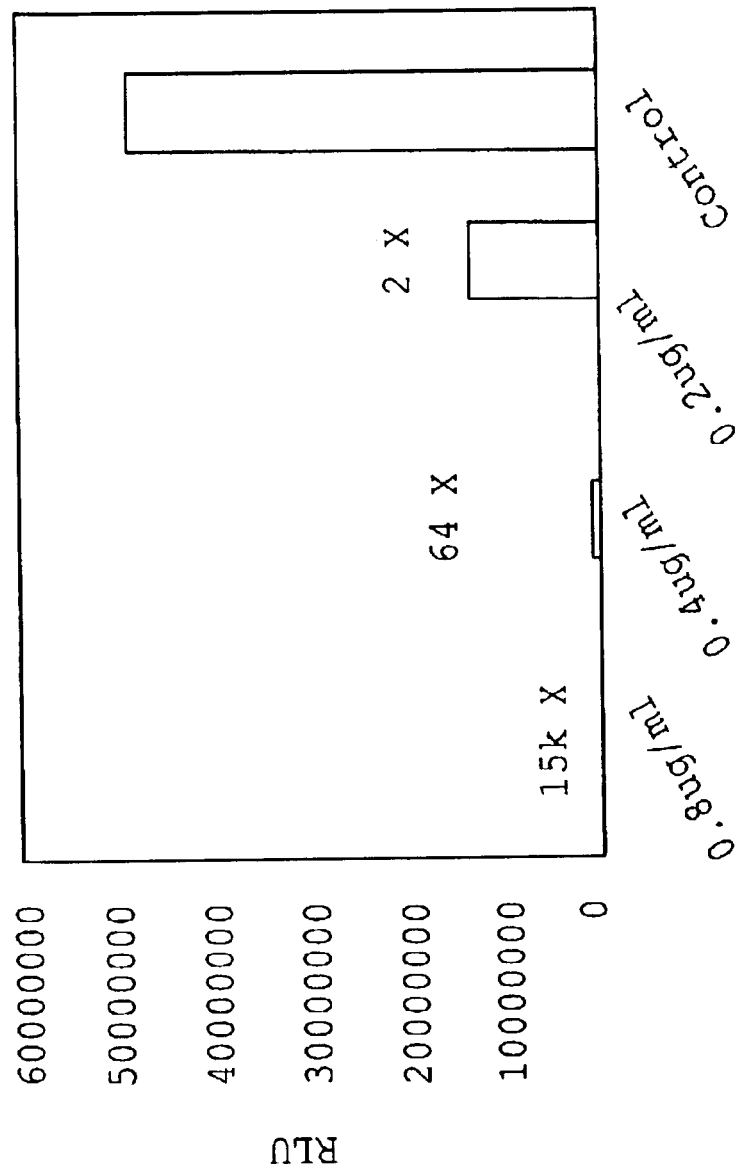
FIG. 21 shows the effect of compound QXP031 on bioluminescence intensity in *V. harveyi* tester strain. The results are normalized to cell count and control strain. Results demonstrate up to 15000 fold specific decrease in bioluminescence as a result of AI-2 inhibition at various compound QXP031 concentrations.

The inhibition of an AI-2 mediated response was further measured in the *V. harveyi* bioassay. Compound QXP031 was tested against *V. harveyi* tester and control strains. As shown in FIG. 21, at the concentrations indicated, compound QXP031 specifically inhibited AI-2 mediated luciferase expression in *V. harveyi* as monitored by bioluminescence intensity. The results are normalized to cell count and any minimal effects seen in the control strain. The fold difference in bioluminescence intensity at the different drug concentrations versus no drug control is indicated above the appropriate bars in FIG. 21.

Figure 22:
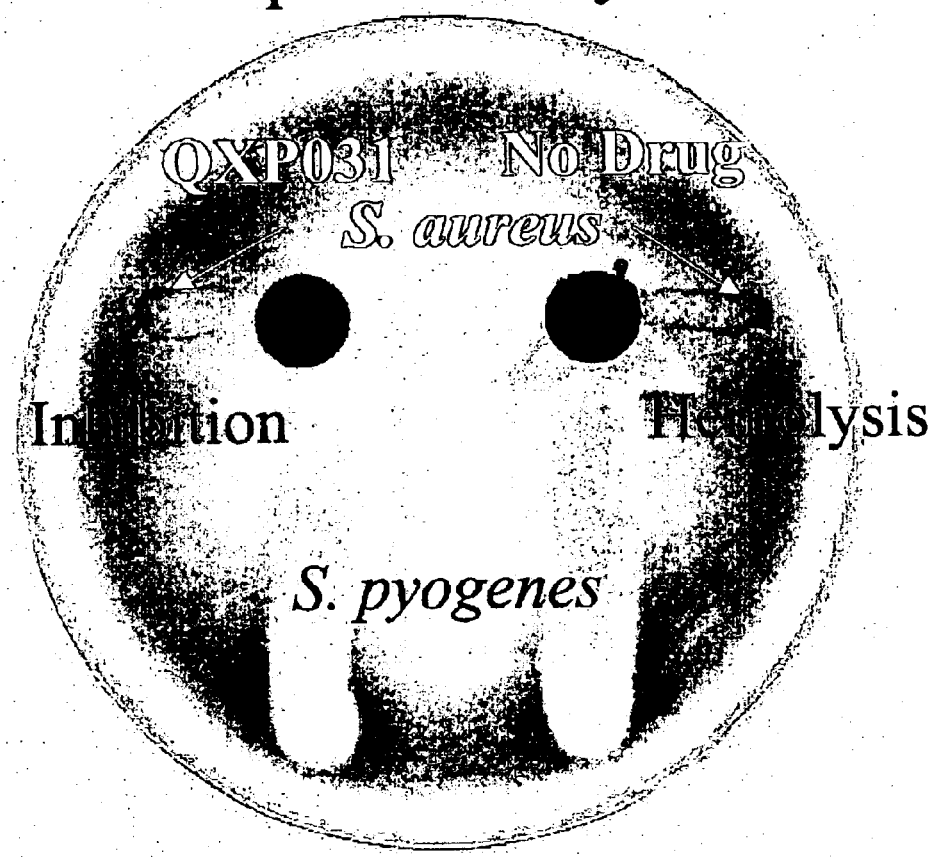
FIG. 22 shows a CAMP assay indicating inhibition of CAMP expression by compound QXP031. The horizontal streak is *S. aureus* 25923 and the vertical streaks are *S. pyogenes* 19615. Filter disks containing either DMSO no drug control or compound QXP031 were applied to plates and incubated anaerobically overnight at 37° C. No compound control results in a positive CAMP score as indicated by the arrow shaped region of complete beta-hemolysis. Application of QXP031 results in a complete inhibition of hemolysis.

In addition, the effect of a compound of the invention on the expression of a virulence factor was measured in a CAMP assay. Many streptococci produce a diffusible extracellular protein (CAMP) that acts synergistically with staphylococcal beta lysin to lyse erythrocytes on trypticase soy agar plates containing sheep blood. Hemolysis of erythrocytes is an important component of the virulence response in many pathogenic bacteria. A single straight streak of a beta lysin producing *S. aureus* strain is made. Steptococci to be tested are streaked perpendicular to the *S. aureus* streak. After overnight incubation a positive test is characterized by an arrowhead-shaped zone of complete hemolysis in the area into which both staphylococcal beta lysin and streptococcal CAMP factor have diffused. Compound QXP031 was tested in a CAMP assay employing *S. aureus* and *S. pyogenes* pathogenic bacteria Application of QXP031 resulted in a negative CAMP score as shown in FIG. 22.

Figure 23:
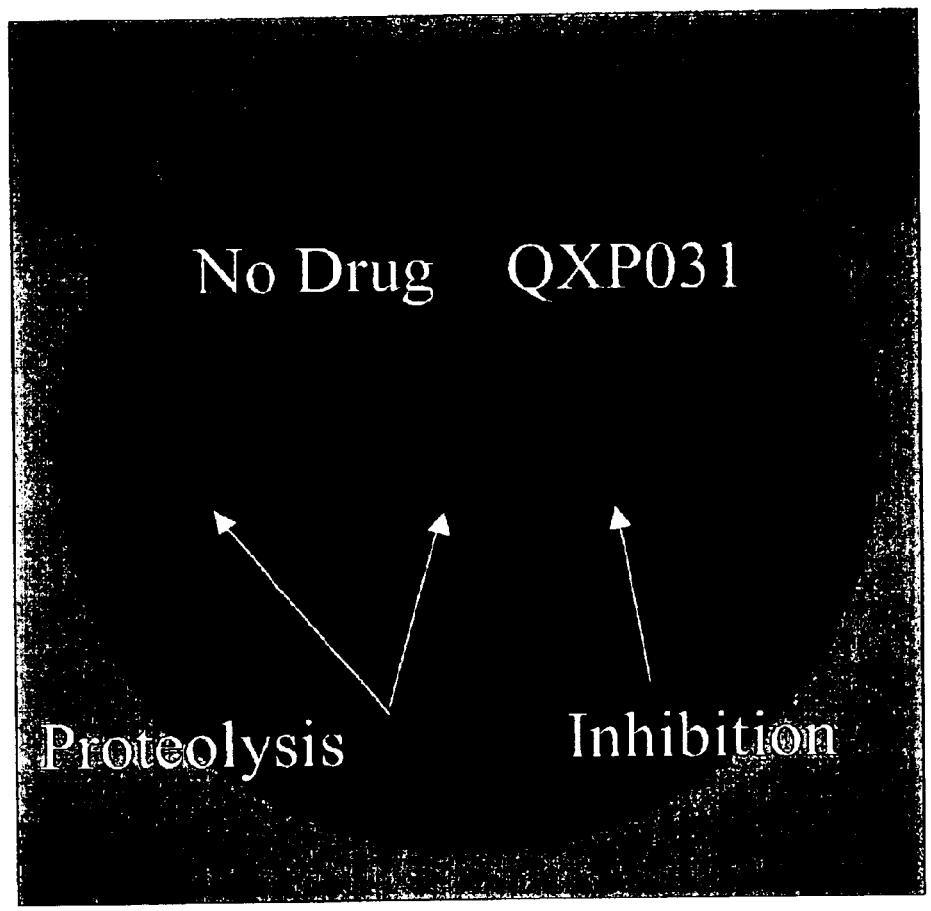
FIG. 23 shows inhibition proteolysis of milk protein by compound QXP031 ((R)-4-acetoxy-cyclopent-2-eneone). Skim milk containing plates were overlaid with top agar containing *S. pyogenes* 19615. Filter disks containing either DMSO no compound control or compound QXP031 were applied to plates and incubated anaerobically overnight at 37° C.
Figure 24:
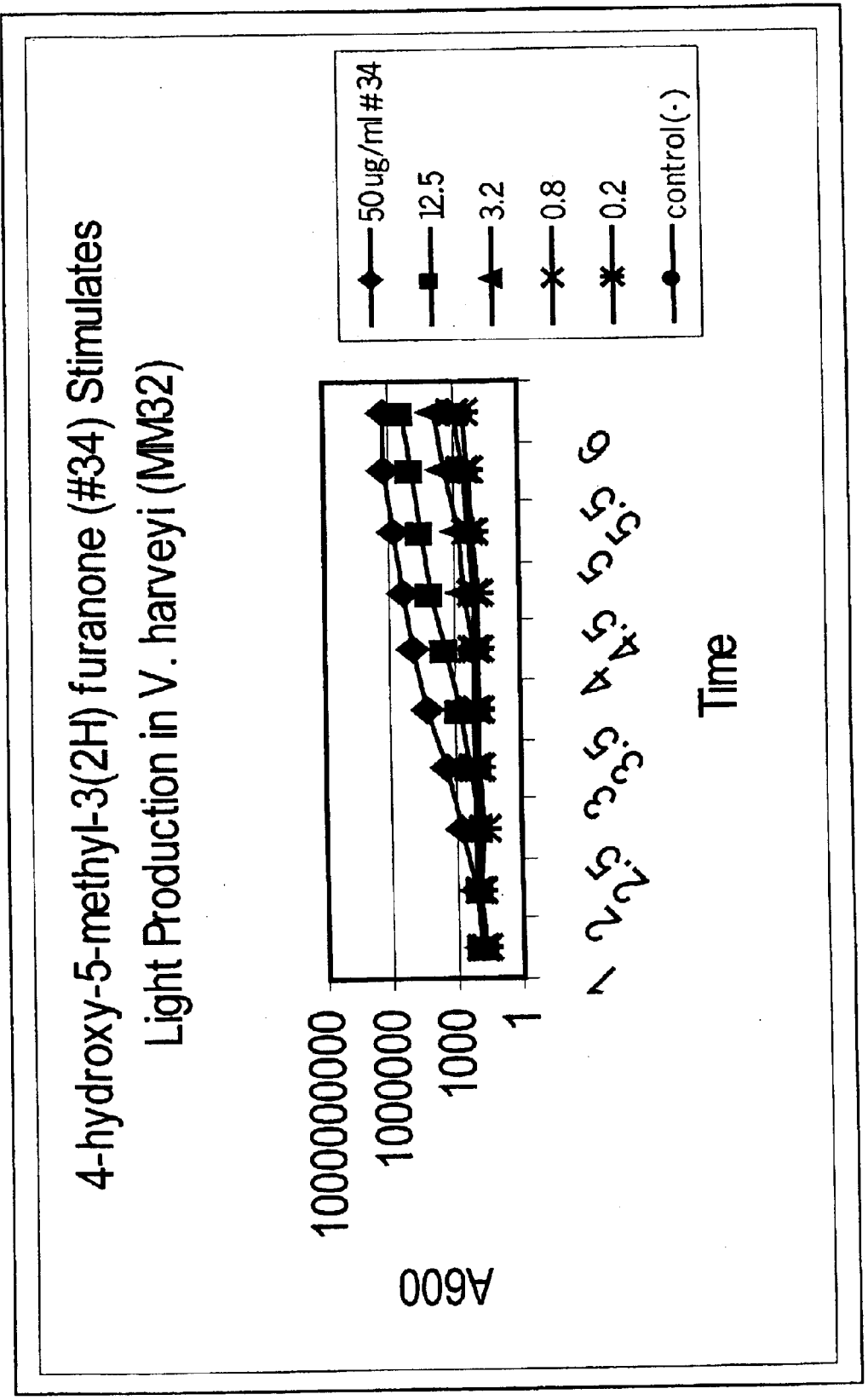
FIG. 24 shows induction of bioluminescence by synthetic 4-hydroxy-5-methyl-2h-furan-3-one. The MM32 indicator strain (LuxS-, LuxN-) of *V. harveyi* was incubated with various doses of AI-2 and the bioluminescence signal measured at various time points during a 6-hour incubation.
Figure 25A:
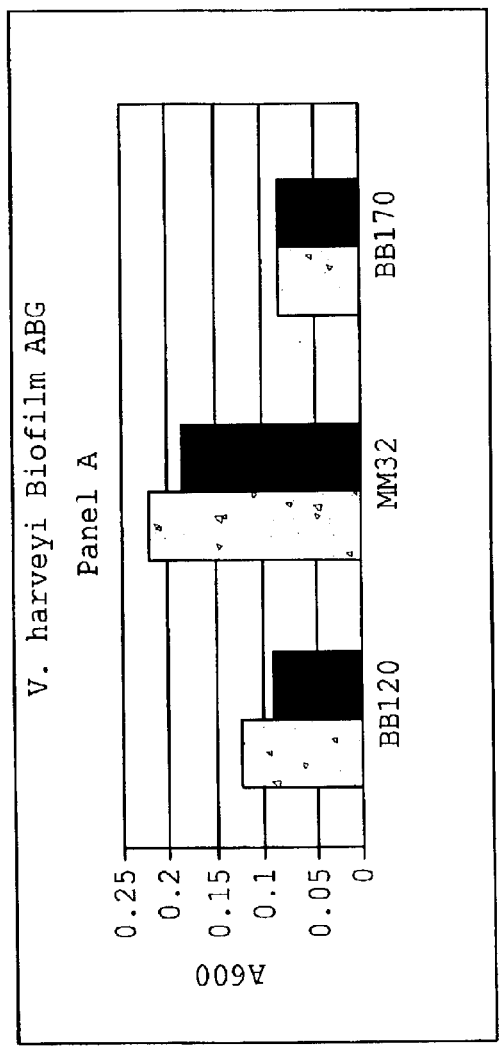
FIG. 25 shows biofilm formation for wild-type *V. harveyi* (strain BB120), strain MM32 (LuxN–, LuxS–) and *V. harveyi* indicator strain BB170 (LuxN–). The strains were tested for biofilm formation using either AB media with supplemented with glucose (ABG; Panel A) or LB media supplemented with glucose (LBG; Panel B). Absorbance reading at 600 nm (A600) were used to measure the amounts of crystal violet adhered to the biofilm.
Figure 25B:
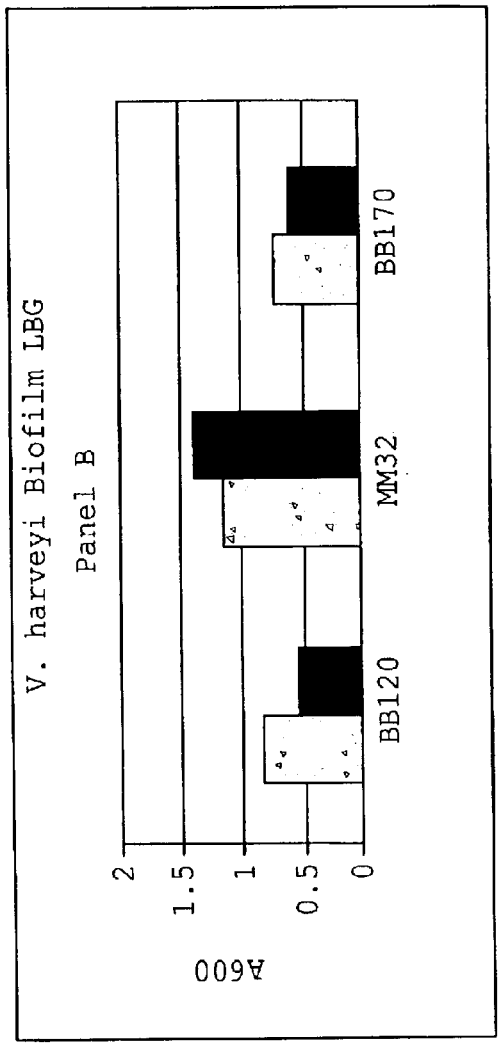

Proteinase activity is an important component of the virulence response in many pathogenic bacteria Skim milk containing agar plates can be used to score for proteinase activity in a variety of bacteria. Proteolytic activity is scored as a clearing zone surrounding a test inoculum. The clearing zone is the result of the proteolytic breakdown of the milk proteins suspended in the agar plates. Regions where milk protein is not broken retain a milky opaque appearance. FIG. 23 shows the inhibition of *S. pyogenes* proteolytic activity by QXP031.

Thus, the present invention to provide compounds and methods for regulating the effect of AI-2 on such targets. Provided herein are compounds of structure I, II, III or IV and pharmaceutical compositions comprising such compounds and methods of using the compounds and compositions of the invention to regulate bacterial growth and virulence by regulating the activity of AI-2 and proteins that interact with AI-2. Thus, the invention provides a mechanism for the control of bacterial growth, such as by inhibition of bacterial growth, utilizing the compounds of the invention. The invention further provides a mechanism to not only control bacterial growth but also to control those pathways involved in expression of phenotypes associated with bacterial virulence and pathogenicity such as siderophore production and rugose polysaccharide production.

Example 12

Biofilm Inhibition

Biofilm formation was measured using a microtiter-based assay. Free-swimming (planktonic) bacteria were cultured in AB or LB media supplemented with glucose in 96 well microtiter dishes. Biofilms typically formed along the walls of the wells at the interface of the liquid and air phase. At the end of the incubation, aliquots of a crystal violet solution (stock 0.1%) were added to the wells to stain both the adherent and the non-adherent cells. The wells were then washed with deionized water to remove non-adherent cells, and the bound crystal violet solubilized with 200 microliters of water. Absorbance reading at 600 nm (A600) were used to quantitate the amount of crystal violet dye that had adhered to the biofilms. When indicated, synthetic AI-2 was added to the wells at the beginning of the cultures.

Figure 26:
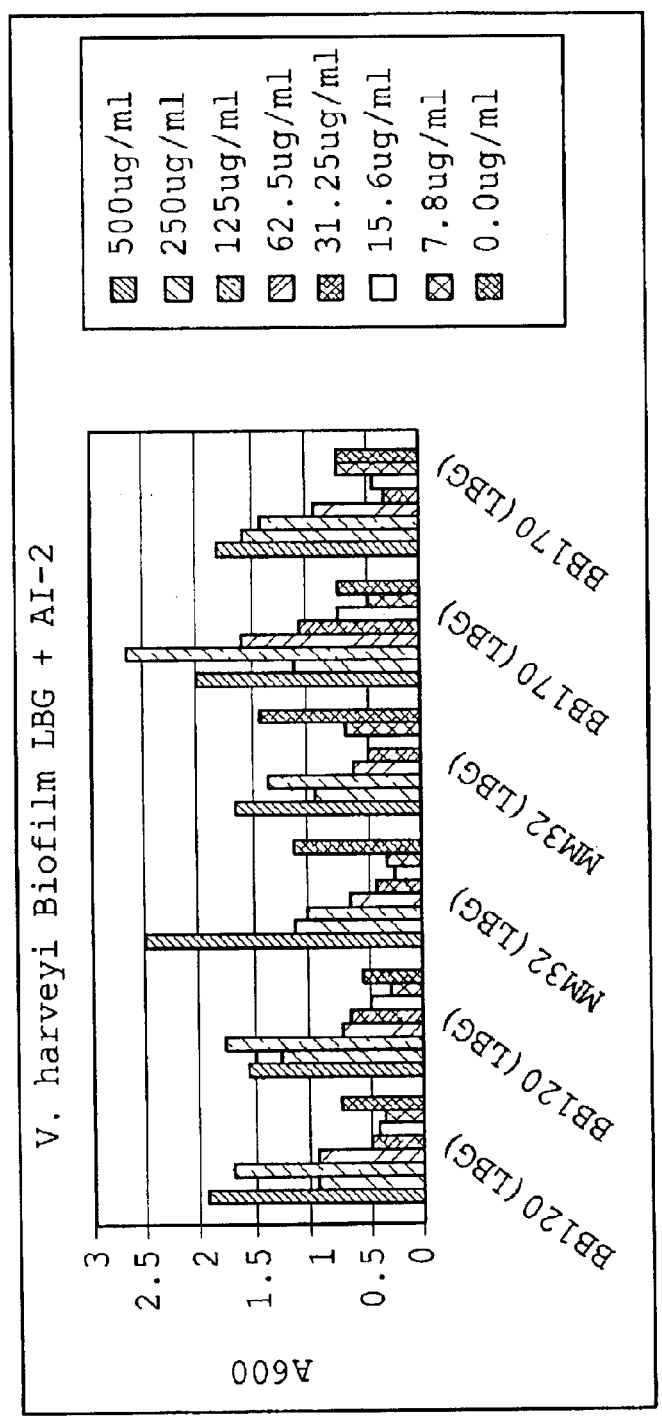
FIG. 26 shows *V. harveyi* biofilm formation in response to increasing amounts of 4-hydroxy-5-methyl-2h-furan-3-one. The final concentration of AI-2 in each assay is indicated.

Various genotypes of *V. harveyi* were tested for biofilm formation in the absence of any exogenous AI-2 (FIG. 26). The MM32 strain (LuxN−, LuxS−) formed more biofilm that either the wild-type *V harveyi* (strain BB120) or *V. harveyi* indicator strain BB170 which contains an inactivating mutation in LuxN. The results were the same regardless of the whether AB media with glucose (Panel A) or LB media supplemented with glucose (Panel B) was used. These observations suggest that more biofilm is produced by *V. harveyi* when the endogenous synthesis of AI-2 is eliminated.

As shown in FIG. 26, strains of *V. harvey* were used to test the effects of exogenous 4-hydroxy-5-methyl-2h-furan-3-one on biofilm formation. Various amounts of synthetic AI-2 were added to the initial free-swimming bacterial cultures in LB media supplemented with glucose, and biofilm formation measured at the end of the incubation. The results indicate that AI-2 affects biofilm formation in all *V. harveyi* strains, and that the results are reproducible for each genotype. In the MM32 strain, low doses of AI-2 block biofilm formation. In contrast, addition of the same low doses of AI-2 to wild-type *V harveyi* (strain BB120) or *V harveyi* indicator strain BB170 increases the extent of biofilm that forms. Higher concentrations of AI-2 stimulated biofilm formation in all *V. harveyi* strains tested.

Figure 27:
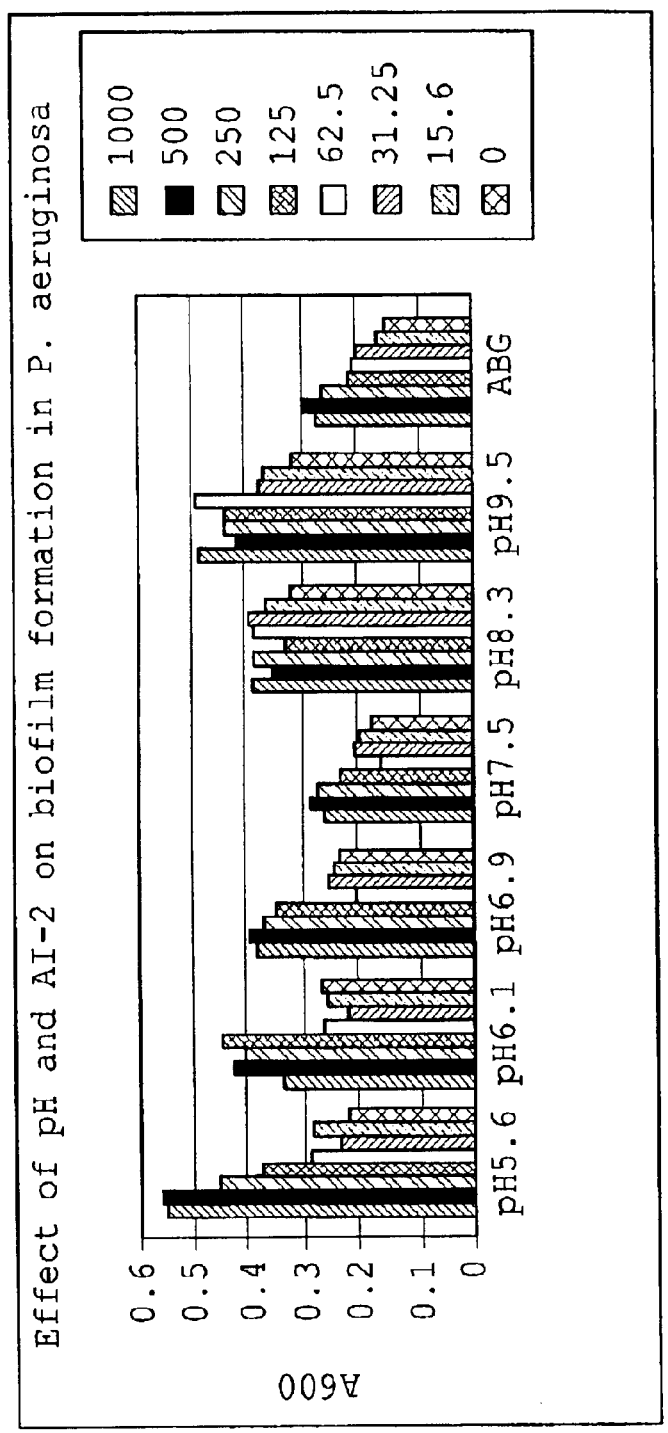
FIG. 27 shows *Pseudomonas aeruginosa* biofilm formation in response to AI-2. *Pseudomonas aeruginosa* (ATCC 27853) were tested for biofilm formation using AB media supplemented with glucose (LBG). Absorbance reading at 600 nm (A600) were used to measure the amounts of crystal violet adhered to the biofilm. Doses in the legend refer to the final concentration of AI-2 in the assay.
Figure 28:
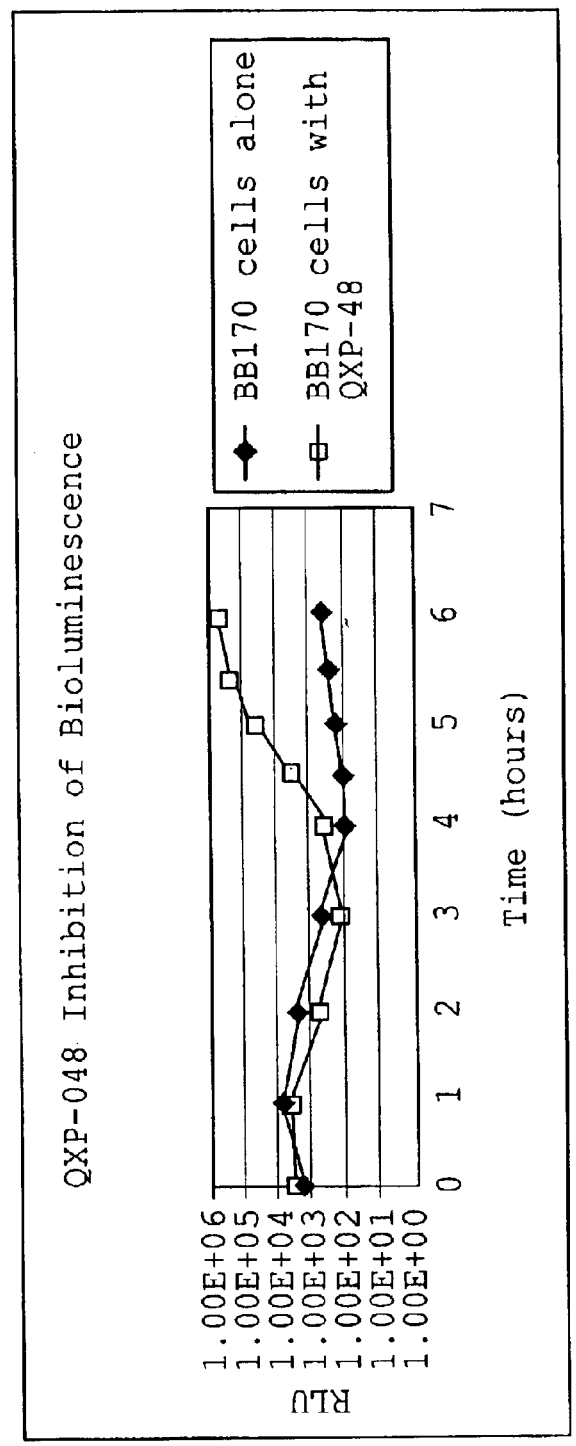
FIG. 28 shows a BB170 assay measuring the effect of QXP-048 (2-methoxy-2,4-diphenyl-3(2H)furanone) on the bioluminescence signal emanating from endogenously produced autoinducer-2. QXP-048 was added at the outset of the assay at a final concentration of 25 µg/ml.
Figure 29:
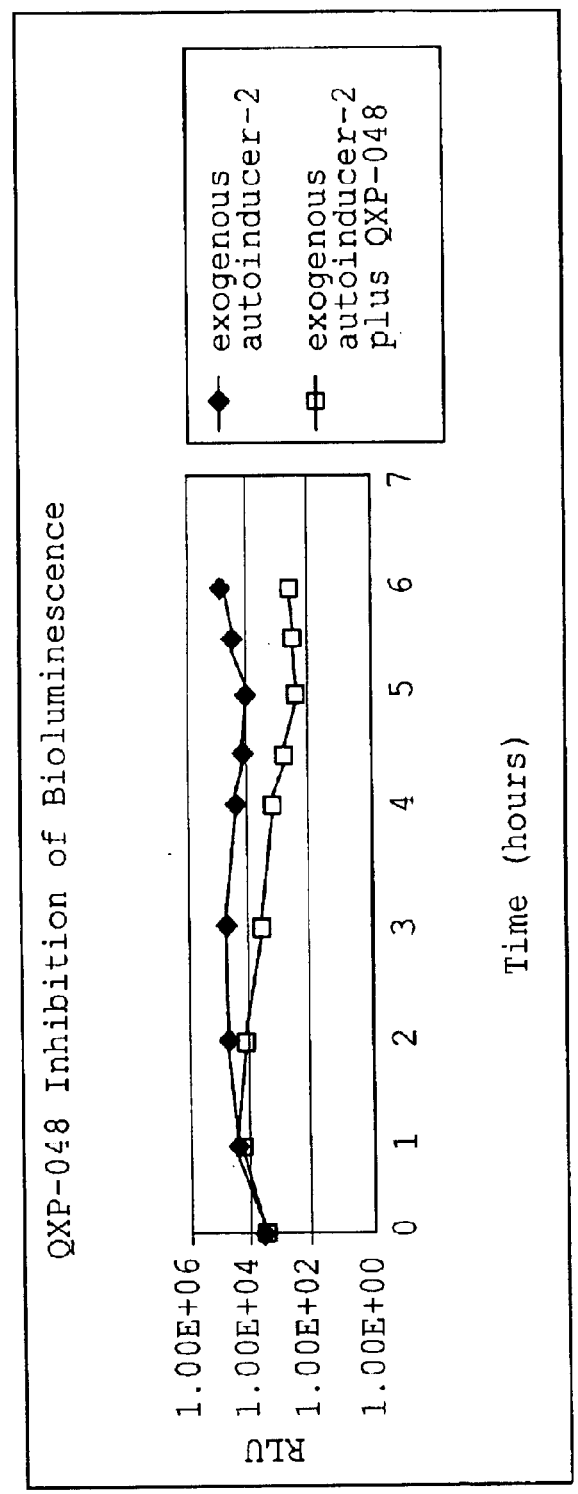
FIG. 29 shows a BB170 Assay measuring the effect of QXP-048 on signal from an exogenous autoinducer-2 signal. Exogenous synthetic autoinducer-2 was added at the outset of the assay at a final concentration of 25 µg/ml. QXP-048 was added at the outset of the assay at a final concentration of 25 µg/ml.
Figure 30:
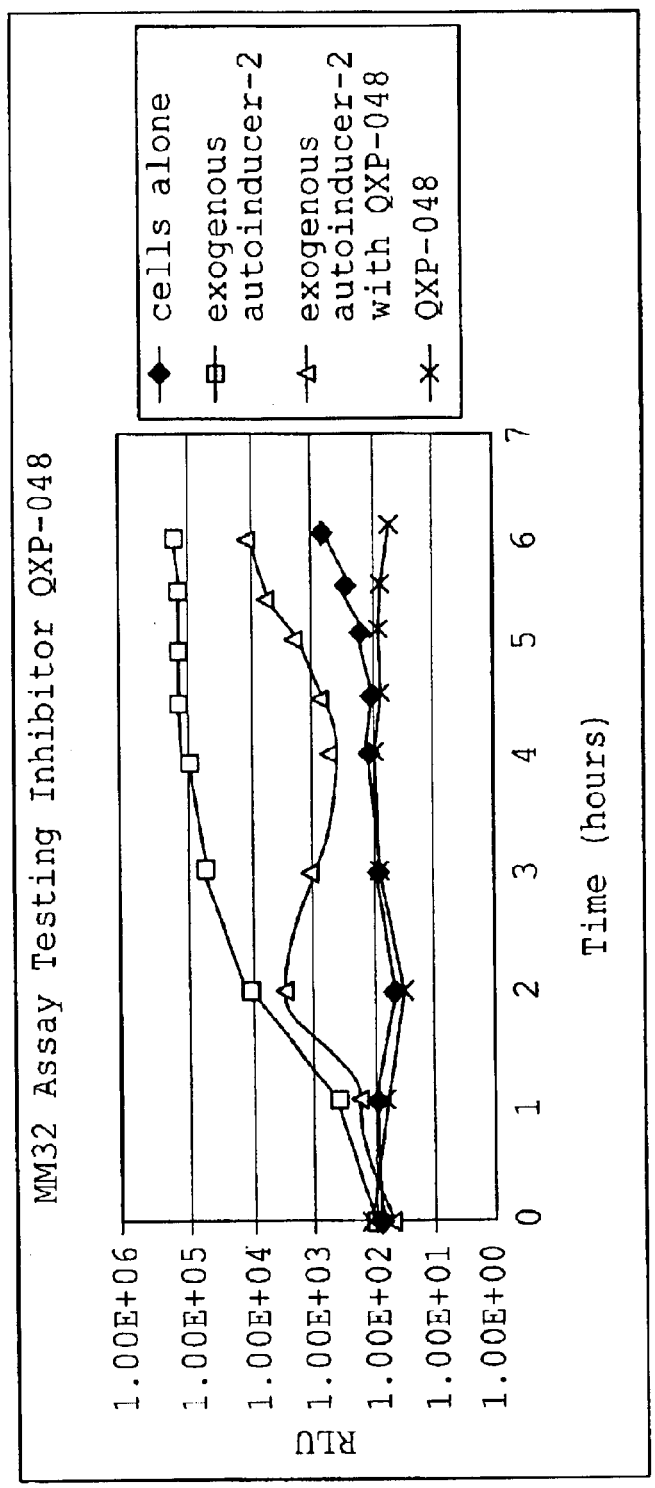
FIG. 30 shows an MM32 assay further identifying the inhibitory capability of compound QXP-048. Exogeneous synthetic autoinducer-2 was added at the outset of the assay to a final concentration of 25 µg/ml. QXP-048 was added at the outset of the assay at a final concentration of 25 µg/ml.
Figure 31:
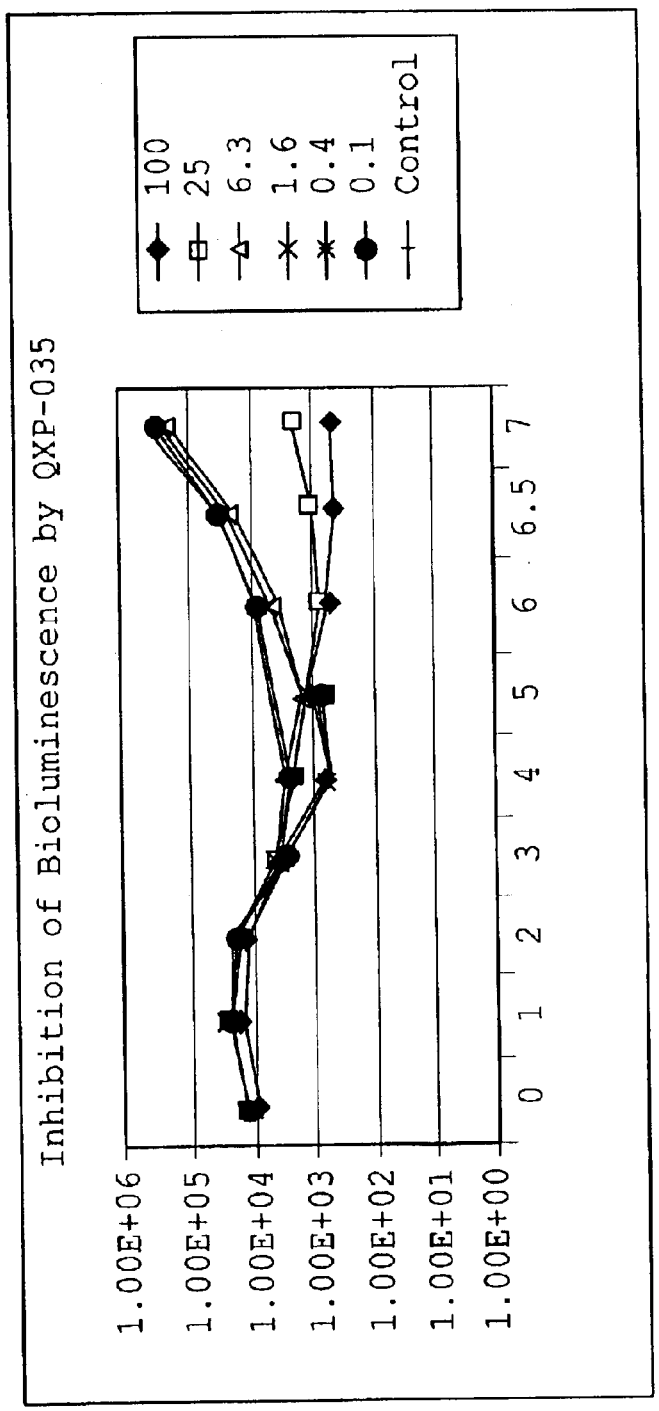
FIG. 31 shows inhibition of bioluminescence by compound QXP-035. Various amounts of QXP-035 were used in BB170-based AI-2-dependent bioluminescence assay (indicated in micrograms/milliliter in the figure legend) and the effects on bioluminescence monitored over time.

The effects of AI-2 on biofilm formation were also evaluated in *Pseudomonas aeruginosa* (ATCC 27853) (FIG. 27). Biofilm formation by this organism is of particular interest because of the association of *Pseudomonas aeruginosa* biofilms with decreased lung capacity in subjects with cystic fibrosis. Using AB media with glucose as the media, addition of exogenous synthetic AI-2 caused a dose-dependent increase in the level of biofilm formation by *P. aeruginosa*. The magnitude and dose-response to AI-2 was found to be pH-dependent in this system.

Materials and Methods

Strains and Media. The bacterial strains used and their genotypes and phenotypes are listed in Table 5.

TABLE 5

Bacterial Strains; Their Genotypes and Relevant Phenotypes

| Strain | Genotype | Relevant phenotype |
| --- | --- | --- |
| *S. typhimurium* LT2 | | Wild type |
| *E. coli* O157 | | Wild type |
| *E. coli* MG1655 | F−, ilvG, rfb-50 | Wild type |
| *E. coli* MC4100 | (lac)U169, araD139, rpsL, thi | LacZ− |
| *E. coli* DH5α | supE44, hsdR17, recA1, endA1, gyrA96, thi-1, reLA1 | AI-2 |
| *V. harvey* BB170 | luxN::Tn5 | Sensor 1−, Sensor 2+ |
| *V. harveyi* BB152 | luxL::Tn5 | AI-1−, AI-2+ |
| *V. harveyi* JAF305 | luxN::Cm5 | Sensor 1−, Sensor 2+ |

Luria broth (LB) contained 10 g Bacto Tryptone (Difco), 5 g Yeast Extract (Difco) and 10 g NaCl per liter (Sambrook et al., 1989). The recipe for Autoinducer Bioassay (AB) medium has been reported previously (Greenberg et al., Arch. Microbiol. 120: 87–91, 1979). LM medium (L-Marine) contains 20 g NaCl, 10 g Bacto Tryptone, 5 g Bacto Yeast Extract and 15 g Agar per liter (Bassler et al., 1994, supra). Regulation of AI-2 production similar to that reported here was also observed with the ATCC strain *Salmonella enterica* Serovar Typhimurium 14028, an independent clinical isolate of *Salmonella enterica* Serovar Typhimurium, and nine other *Salmonella enterica* serovars (other than Typhimurium).

Growth Conditions for *S. typhimurium* LT2 and Preparation of Cell-free Culture Fluids. *S. typhimurium* LT2 was grown overnight in LB broth with shaking at 30° C. The next day, 30 $\mu$l of the overnight culture was used to inoculate 3 ml of fresh LB broth. In cultures containing additional carbon sources, at the time of inoculation, 20% sterile stock solutions were added to give the specified final concentrations. Following subculturing of the cells, the tubes were shaken at 200 rpm at 30 C for the time periods indicated in the text. Cell-free culture fluids were prepared by removal of the cells from the culture medium by centrifugation for 5 min at 15,000 rpm in a microcentrifuge. The cleared supernatants were passed through 0.2 $\mu$m cellulose acetate Spin X filters (CoStar, Cambridge, Mass.) by centrifugation for 1 min at 8000×g. Samples were stored at −2° C. Similar results to those reported here were obtained when we grew the *S. typhimurium* at 37° C. The preparation of cell-free culture fluids from *V. harveyi* strains has already been reported (Bassler et al., 1993, supra; Bassler et al., 1997, supra).

Density-dependent Bioluminescence Assay. The *V. harveyi* reporter strain BB170 (Sensor 1$^-$, Sensor 2$^+$) (Bassler et al., 1993, supra) was grown for 12 h at 30° C. in AB medium, and diluted 1:5000 into fresh AB medium. Luminescence was measured as a function of cell density by quantitating light production at different times during growth with a Wallac Model 1409 liquid scintillation counter (Wallac Inc., Gaithersburg, Md.). The cell density was measured by diluting the same aliquots of cells used for measuring luminescence, spreading the dilutions onto solid LM medium, incubating the plates overnight at 30° C., and counting the resulting colonies the following day. Relative Light Units are (counts min$^{-1}$ m$^{-1}$×10$^3$)/(colony forming units ml$^{-1}$). Cell-free culture supernatants from *V. harveyi* or *S. typhimurium* strains were added to a final concentration of 10% (v/v) at the time of the first measurement. In control experiments, 10% (v/v) of AB medium, LB medium or LB medium containing 0.5% glucose was added instead of cell-free culture fluids.

*S. typhinumrim* Autoinducer Activity Assay. The quorum-sensing signaling activity released by *S. typhimurium* LT2 was assayed following growth under various conditions. 10 $\mu$l of cell-free culture fluids from *S. typhimurium* LT2 grown and harvested as described above were added to 96-well microtiter dishes. The *V. harveyi* reporter strain BB170 was grown overnight and diluted as described above. Ninety microliters of the diluted *V. harveyi* cells were added to the wells containing the *S. typhimurium* cell-free culture fluids. Positive control wells contained 10 $\mu$l of cell-free culture fluid from *V. harveyi* BB152 (AI-1$^-$, AI-2$^+$) (Bassler et al., 1993, supra). The microtiter dishes were shaken in a rotary shaker at 200 rpm at 30° C. Light production was measured hourly using a Wallac Model 1450 Microbeta Plus liquid scintillation counter designed for microtiter dishes (Wallac Inc., Gaithersburg, Md.). In these experiments, the cell density was not measured at each time point. Rather, to ensure that increased light production was due to a signaling activity and not a growth medium component, the luminescence production by *V. harveyi* in wells containing cell-free culture fluids was compared to that produced by *V. harveyi* in wells containing 10 $\mu$l of the identical growth medium alone. Data are reported as fold-stimulation over that obtained for growth medium alone.

Factors Controlling Signal Production in *S. typhimurium*. *S. typhimurium* LT2 was grown for 6 h in LB containing 0.5% glucose as described above. The mid-exponential phase culture was divided into several identical aliquots. One aliquot of cells was grown to stationary phase (24 h at 30° C. with shaking). In the remaining aliquots, the cells were removed from the LB-glucose growth medium by centrifugation for 5 min at 15,000 rpm in a microcentrifuge. The resulting cell pellets were resuspended at an OD$_{600}$ of 2.0 in either LB, LB+0.5% glucose, LB at pH 5.0, or in 0.1M NaCl, or 0.4M NaCl (in water). The resuspended cells were shaken at 30° C. or 43° C. for 2 h. Cell-free fluids were prepared from the stationary phase culture, and from the cells that had been resuspended and incubated in the various media or the osmotic shock solutions. The cell-free fluids were tested for signaling activity in the *S. typhimurium* activity assay as described above.

Effects of Growth Phase, pH, Glucose Concentration and Osmolarity on Autoinducer Production by *S. typhimurium*. *S. typhimurium* LT2 was grown at 30° C. for various times in LB containing limiting (0.1%) and non-limiting (1.0%) glucose concentrations. At the times specified in the text, the cell number was determined by plating dilutions of the *S. typhimurium* cultures onto LB medium and counting colonies the following day. The pH of the two cultures was measured, and the percent glucose remaining in each culture was determined using the Trinder assay as described in Example 1. Cell-free culture fluids were prepared from the LB-glucose cultures as described above. The same cells from which the cell-free culture fluids were prepared were resuspended in 0.4M NaCl osmotic shock solution and shaken at 200 rpm, 30° C. for 2 h. We determined that this timing was optimal for production of autoinducer. The cells were removed from the osmotic shock solution by centrifugation at 15,000 rpm for 5 min in a microcentrifuge. Cell-free osmotic shock fluids were prepared from the resuspended cells exactly as described for cell-free culture fluids. Signaling activity in both the cell-free culture fluids and the cell-free osmotic shock fluids was assayed as described above. In experiments in which the pH was maintained at 7.2, the cells were grown in LB+0.5% glucose containing 50 mM MOPS at pH 7.2. The pH was adjusted every 15–30 min using 1 M MOPS pH 7.2. In experiments performed at pH 5.0, LB broth was maintained between pH 5.0 and 5.2 with 1M NaOH.

Requirement for Protein Synthesis in Signal Production, Release and Degradation by *S. typhimurium* LT2. *S. typhimurium* LT2 was pre-grown in LB containing 0.5% glucose at 30° C. to an OD$_{600}$ of 2.5 (approximately 6–8 h). The culture was divided into four identical aliquots. Two aliquots were treated with 100 $\mu$g/ml Cm for 5 min at room temperature after which the cells were harvested by centrifugation at 15,000 rpm for 5 min. One Cm-treated cell pellet was resuspended in 0.1M NaCl containing 30 $\mu$g/ml Cm, and the second pellet was resuspended in 0.4M NaCl containing 30 g/ml Cm. Each of these pellets was resuspended to a final OD$_{600}$ of 2.0. The remaining two culture aliquots were not treated with Cm. Instead, the cells in these two aliquots were harvested by centrifugation and resuspended in 0.1M and 0.4M NaCl exactly as described for the Cm-treated cells. The cell suspensions were incubated at 30° C. with shaking.

At the times indicated in the text, 1.5 ml aliquots were removed from the cell suspensions and cell-free osmotic shock fluids were prepared by the procedure described above.

Analysis of the Effect of Autoinducer on SdiA Regulated Gene Expression. A sequence that includes the ftsQ1p and ftsQ2p promoters (Wang et al., 1991, supra) was amplified from *E. coli* MG1655 chromosomal DNA using the following primers: ftsQ1p, 5'-CGGAGATCTGCGCTTTCAA TGGATAAACTACG-3'; fisQ2p, 5'-CGCGGATCCTCTTC TTCGCTGTTTCGCGTG-3'. The amplified product contained both the ftsQ promoters and the first 14 codons of the ftsQ gene flanked by BamHI and BglII sites. The ftsQ1p2p PCR product was cloned into the BamHI site of vector pMLB1034 (Silhavy et al., Experiments with Gene Fusions, Cold Spring Harbor Press, 1984) to generate a lacZ fusion that contained the promoters, ribosome-binding site, and initiation codon of ftsQ. A correctly oriented clone, pMS207, and a clone containing the ftsQ1p2p insert in the opposite orientation, pMS209, were chosen for further analysis. Both inserts were sequenced to ensure that no errors were introduced during the PCR reaction.

For ftsQ regulation in *E. coli*, the plasmids pMS207 and pMS209 were transformed into *E. coli* strain MC4100 (Silhavy et al., 1984, supra), and the transformants were grown overnight in LB containing 100 mg/L ampicillin at 30° C. with aeration. For rck regulation, *S. typhimurium* strains BA1105 (rck::MudJ) and BA1305 (rck::MudJ sdiA) were grown overnight in LB containing 100 mg/L kanamycin at 30° C. with aeration. The overnight cultures were diluted 20-fold into fresh medium and grown for an additional 4.5 h. At this time, each culture was divided into five identical aliquots and 10% (v/v) of one of the following was added to each aliquot: LB, 0.4M NaCl, 0.4M osmotic shock fluids from *S. typhimurium* LT2, *E. coli* O157 or *E. coli* strain DH5α (negative control). The osmotic shock fluids were prepared as described above, following pre-growth of the *S. typhimurium* LT2 and *E. coli* in LB containing 0.5% glucose for 6 h. The cell suspensions were incubated at 30° C. for 2 h, after which standard-galactosidase reactions were performed on the samples (Miller, A Short Course in Bacterial Genetics, Cold Spring Harbor Laboratory Press, 1992).

Preparation of Cell free Culture Fluids. *E. coli* strains AB1157 and DH5α and *S. typhimurium* strain LT2 were grown at 30° C. overnight with aeration in LB broth containing glucose at the concentrations specified in the text. The following morning, fresh LB medium containing the same concentration of glucose used for the overnight growth was inoculated at a 1:100 dilution with the overnight grown cultures. The fresh cultures were grown for various times at 30° C. with aeration. Cell-free culture fluids were prepared by removing the cells from the growth medium by centrifugation at 15,000 rpm for 5 min in a microcentrifuge. The cleared culture fluids were passed through 0.2 µm HT Tuffryn filters (Gelman) and stored at −20° C. Cell-free culture fluids containing *V. harveyi* Autoinducer-2 were prepared from *V. harveyi* strain BB152 (Autoinducer 1−, Autoinducer 2+). *V. harveyi* BB120 (Autoinducer 1+, Autoinducer 2+) was used to prepare culture fluids containing Autoinducer-1. In both cases, the *V. harveyi* strains were grown overnight at 30° C. with aeration in AB (Autoinducer Bioassay) (Bassler et al., 1993, supra) medium. Cell-free culture fluids from *V. harveyi* were prepared from the overnight culture exactly as described above for *E. coli* and *S. typhimurium*.

Assay for Production of Signaling Molecules. Cell-free culture fluids from *E. coli*, *S. typhimurium* and *V. harveyi* strains were tested for the presence of signaling substances that could induce luminescence in the *V. harveyi* reporter strain BB170 or BB886. In the assays, 10 µl of cell-free culture fluids from *E. coli* ABI 157, *E. coli* DH5α, and *S. typhimurium* LT2 strains grown and harvested as described above were added to 96-well microtiter dishes. The *V. harveyi* reporter strain BB170 or BB886 was grown for 16 h at 30° C. with aeration in AB medium, diluted 1:5000 into fresh AB medium, and 90 µl of the diluted cells were added to the wells containing the *E. coli* and *S. typhimurium* cell-free culture fluids. Positive control wells contained 10 µl of cell-free culture fluid from strain *V. harveyi* BB152 (Autoinducer-1−, Autoinducer-2+) or *V. harveyi* BB120 (Autoinducer-1+, Autoinducer-2+). Negative control wells contained 10 µl of sterile growth medium. The microtiter dishes were shaken in a rotary shaker at 175 rpm at 30° C. Every hour, light production was measured using a Wallac Model 1450 Microbeta Plus liquid scintillation counter in the chemiluminescence mode. The *V. harveyi* cell density was measured by diluting the same aliquots of cells used for measuring luminescence, spreading the dilutions onto solid LM medium (Bassler et al., 1993, supra, incubating the plates overnight at 30° C., and counting the resulting colonies the following day.

Preparation of *E. coli* and *S. typhimurium* Viable and UV-killed Cells for the Activity Assay. *E. coli* ABI 157, *E. coli* DH5α and *S. typhimurium* LT2 cultures were grown for 8 h in LB containing 0.5% glucose at 30° C. with aeration. The cultures were subjected to centrifugation for 5 min at 15,000 rpm in a microcentrifuge and the growth medium was removed from the cell pellets by aspiration. The cell pellets were resuspended in AB medium and washed by vigorous mixing. The cells were again subjected to centrifugation for 5 min at 15,000 rpm. The AB wash medium was removed and discarded and the cells were resuspended in fresh AB medium. Each cell suspension was diluted to give $1 \times 10^6$ cells/10 µl, and multiple 10 µl aliquots were added to wells of microtiter dishes. Half of the cell aliquots were treated with short wavelength ultraviolet light for 15 min at a distance of 10 cm. This treatment was sufficient to kill all of the cells as judged by plating and incubating the UV-treated cells, and ensuring that no growth occurred by the next day. 90 µl of the diluted *V. harveyi* reporter strain BB170 was next added to the wells containing either the viable or dead *E. coli* and *S. typhimurium* cells, and the activity assay was carried out exactly as described in the previous section.

Analysis of Glucose in *S. typhimurium* LT2 Culture Fluids. Glucose concentrations were determined in cell-free culture fluids prepared from *S. typhimurium* using a Trinder assay (Diagnostic Chemicals Ltd.) according to the recommendations of the manufacturer, except that the glucose standards were prepared in LB medium. The assay was sensitive to less than 0.002% glucose. No interfering substances were present in LB medium or spent LB culture fluids.

Bacterial Strains, Media and Recombinant DNA Techniques. *V. harveyi* BB120 is the wild type strain (Bassler et al., 1997, supra). *S. typhimurium* strain LT2 was obtained from Dr. K Hughes (University of Washington), *S. typhimurium* 14028 is ATCC strain 14028 Organism: *Salmonella choleraesuis*. *E. coli* O157:H7 is a clinical isolate supplied by Dr. Paddy Gibb (University of Calgary). Luria broth (LB) contained 10 g Bacto Tryptone (Difco), 5 g Yeast Extract (Difco) and 10 g NaCl per liter. The recipe for Autoinducer Bioassay (AB) medium has been reported previously (Greenberg, E. P., Hastings, J. W., and Ulitzur, S. (1979) Arch. Microbiol. 120, 87–91). Where specified, glucose was added from a sterile 20% stock to a final concentration of 0.5%. Antibiotics were used at the following concentrations (mg/L): Ampicillin (Amp) 100, Chloramphenicol (Cm) 10, Gentamycin (Gn) 100, Kanamycin (Kn) 100, and Tetracycline (Tet) 10. DNA isolation, restriction analysis and transformation of E. coli was performed as described by Sambrook et al. Probes for Southern Blot analysis were labeled using the Multiprime DNA labeling system of Amersham. Sequencing was carried out using an Applied Biosystems sequencing apparatus. The V. harveyi BB120 genomic library was constructed in the cosmid pLAFR2 as described (Bassler et al., 1993, supra). The method for Tn5 mutagenesis of cloned V. harveyi genes, and the allelic replacement technique for inserting Tn5 mutated genes into the V. harveyi chromosome have been reported (Bassler et al., 1993, supra).

Bioluminescence Assay. The AI-2 bioassay using the V. harveyi reporter strain BB170 (Sensor 1⁻, Sensor 2⁺) has been discussed in the previous examples. Cell-free culture fluids from V. harveyi, E. coli, or S. typhimurium strains to be tested for AI-2 activity were prepared as described above, and assayed at 10% (v/v). AI-2 activity is reported as the fold-induction of the reporter strain over background, or as the percent of the activity obtained from V. harveyi BB120 (wild type) cell-free culture fluid.

Mutagenesis and Analysis of the AI-2 Production Gene In S. typhimurium LT2. MudJ insertion mutants of S. typhimurium LT2 were generated using a phage P22 delivery system as described (Maloy, S. R., Stewart, V. J., and Taylor, R. K. (1996) Genetic analysis of pathogenic bacteria: a laboratory manual. Cold Spring Harbor Laboratory Press, Cold Spring Harbor, N.Y.). Following growth to mid-exponential phase in LB containing 0.5% glucose, the S. typhimurium insertion mutants were tested for AI-2 production using the V. harveyi BB170 bioassay. The site of the MudJ insertion that inactivated the AI-2 production function in S. typhimurium was identified by PCR amplification and sequencing of the chromosomal DNA at the insertion junction. A two-step amplification procedure was used (Caetano-Annoles, G. (1993) Meth. Appl. 3, 85–92). In the first PCR reaction, the arbitrary primer 5'-GGCCACGCGTCGACTAGTACNN NNNNNNNACGCCC-3', and the MudJ specific primer 5'-GCACTACAGGCTTGCAAGCCC-3' were used. Next, 1 μl of this PCR reaction was used as the template in a second PCR amplification employing a second arbitrary primer (5'-GGCCACGCGTCGACTAGTCA-3') and another MudJ specific primer (5'-TCTAATCCCATCAGATCCCG-3'). The PCR product from the second reaction was purified and sequenced.

Cloning and Sequencing of the E. coli MG1655, E. coli O157:H7, and E. coli DH5α AI-2 Production Genes. The DNA sequence obtained from the S. typhimurium LT2 MudJ screen was used to search the E. coli MG1655 genome sequence to identify the corresponding E. coli region (Blattner et al., Science 277, 1453–1462, 1997). The gene identified from the sequencing project had the designation ygaG. Primers that flanked the ygaG gene and incorporated restriction sites were designed and used to amplify the E. coli MG1655, E. coli O157:H7 and E. coli DH5α ygaG genes. The primers used are: 5'-GTGAAGCTT GTTTACTGACTAGATC-3' and 5'-GTGTCTAGAAAAAC ACGCCTGACAG-3'. The PCR products were purified, digested, and cloned into pUC19. In each case, the PCR products from three independent reactions were cloned and sequenced.

The present invention is not limited to the embodiments described and exemplified above, but is capable of variation and modification within the scope of the appended claims.

What is claimed is:

1. A method for introducing autoinducer-2 comprising contacting S-adenosylhomocysteine (SAH with a LuxS protein whereby S-adenosylhomocysteine undergoes conversion to autoinducer-2.

2. The method of claim 1, wherein the production of autoinducer-2 is in vitro.

3. The method of claim 1, wherein the production of autoinducer-2 is in vivo.

4. The method of claim 1, further comprising a 5'-methylthioadenosine/S-adenosylhomocysteine nucleosidase protein (pfs).

5. The method of claim 1, wherein the autoinducer-2 is 4-hydroxy-5-methyl-2H-furan-3-one.

6. A method for producing autoinducer-2 comprising contacting S-ribosylhomocysteine (SRH) with a LuxS polypeptide whereby S-ribosylhomocysteine undergoes conversion to autoinducer-2.

7. The method of claim 6, wherein the autoinducer-2 is 4-hydroxy-5-methyl-2H-furan-3-one.

8. Isolated autoinducer-2 prepared in accordance with the method of claim 6.

* * * * *